US010669301B2

(12) United States Patent
Guzaev et al.

(10) Patent No.: US 10,669,301 B2
(45) Date of Patent: *Jun. 2, 2020

(54) PHOSPHORAMIDITE BUILDING BLOCKS FOR SUGAR-CONJUGATED OLIGONUCLEOTIDES

(71) Applicant: AM CHEMICALS LLC, Oceanside, CA (US)

(72) Inventors: Andrei Pavel Guzaev, Escondido, CA (US); Vladimir Y. Vvedenskiy, San Diego, CA (US)

(73) Assignee: AM CHEMICALS LLC, Oceanside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/118,341

(22) Filed: Aug. 30, 2018

(65) Prior Publication Data

US 2018/0362572 A1    Dec. 20, 2018

Related U.S. Application Data

(63) Continuation of application No. 14/960,197, filed on Dec. 4, 2015, now Pat. No. 10,087,208, which is a continuation of application No. PCT/US2014/041133, filed on Jun. 5, 2014.

(60) Provisional application No. 61/831,521, filed on Jun. 5, 2013.

(51) Int. Cl.
*C07H 19/16* (2006.01)
*C07H 19/06* (2006.01)
*C07H 21/00* (2006.01)

(52) U.S. Cl.
CPC ............. *C07H 19/16* (2013.01); *C07H 19/06* (2013.01); *C07H 21/00* (2013.01); *Y02P 20/55* (2015.11)

(58) Field of Classification Search
CPC ........ C07H 19/06; C07H 19/16; C07H 21/00; Y02P 20/55
See application file for complete search history.

(56) References Cited

U.S. PATENT DOCUMENTS

| | | | |
|---|---|---|---|
| 4,415,732 A | 11/1983 | Caruthers et al. | |
| 4,458,066 A | 7/1984 | Caruthers et al. | |
| 4,500,707 A | 2/1985 | Caruthers et al. | |
| 4,668,777 A | 5/1987 | Caruthers et al. | |
| 5,132,418 A | 7/1992 | Caruthers et al. | |
| 5,597,699 A | 1/1997 | Lanzara | |
| 5,700,919 A | 12/1997 | Seliger et al. | |
| 5,955,599 A | 9/1999 | Iyer et al. | |
| 6,121,437 A | 9/2000 | Guzaev et al. | |
| 6,593,094 B2 | 7/2003 | Lanzara | |
| 6,610,837 B1 | 8/2003 | Guzaev et al. | |
| 6,610,842 B1 | 8/2003 | Ravikumar et al. | |
| 6,673,558 B1 | 1/2004 | Lanzara | |
| 6,919,437 B1 | 7/2005 | Manoharan et al. | |
| 7,339,052 B2 | 3/2008 | Reddy | |
| 7,723,528 B2 | 5/2010 | Guzaev | |
| 7,723,852 B1 | 5/2010 | Kim et al. | |
| 8,691,971 B2 | 4/2014 | Petersen | |
| 9,809,824 B2 * | 11/2017 | Verthelyi | C07H 21/00 |
| 10,087,208 B2 * | 10/2018 | Guzaev | C07H 19/06 |
| 2001/0004529 A1 | 6/2001 | Lanzara et al. | |
| 2002/0147331 A1 | 10/2002 | Guzaev et al. | |
| 2003/0229218 A1 | 12/2003 | Sinha et al. | |
| 2006/0178509 A1 | 8/2006 | Reddy | |
| 2009/0263405 A1 | 10/2009 | Verthelyi et al. | |
| 2016/0083414 A1 | 3/2016 | Guzaev et al. | |

FOREIGN PATENT DOCUMENTS

| | | |
|---|---|---|
| EP | 3004131 | 4/2016 |
| WO | 2003/048179 | 5/2003 |
| WO | 2006/065751 | 12/2006 |
| WO | 2010/039543 | 4/2010 |
| WO | 2014/031575 | 2/2014 |
| WO | 2014197714 | 12/2014 |

OTHER PUBLICATIONS

U.S. Appl. No. 14/960,197, "Advisory Action", dated May 4, 2018, 5 pages.
U.S. Appl. No. 14/960,197, "Final Office Action", dated Feb. 9, 2018, 7 pages.
U.S. Appl. No. 14/960,197, "Non-Final Office Action", dated Oct. 3, 2017, 7 pages.
U.S. Appl. No. 14/960,197, "Notice of Allowance", dated Jun. 13, 2018, 7 pages.
Beaucage et al., "Advances in the Synthesis of Oligonucleotides by the Phosphoramidite Approach", Tetrahedron, vol. 48, 1992, pp. 2223-2311.
Beaucage, "The Synthesis of Modified Oligonucleotides by the Phosphoramidite Approach and Their Applications", Tetrahedron, 1993, pp. 6123-6194.
EP14808105.2, "Extended European Search Report", dated Sep. 9, 2016, 6 pages.
EP14808105.2, "Office Action", dated May 31, 2017, 4 pages.
Fukase et al., "Synthesis and Biological Activities of Lipid A Analogs Possessing β-Glycosidic Linkage at 1-Position", Bull. Chem. Soc. Japan, 2003, pp. 485-500.
IL242802, "Office Action", dated Feb. 1, 2018, 4 pages.
Karjala et al., "Synthesis of Glycol Glucosides", J. Amer. Chem. Oc., 1940, pp. 917-922.
Lesser et al., "Stereoselective Interaction with Chiral Phosphorothioates at the Central DNA Kink of the EcoRI Endonuclease—GAATTC Complex", Biol. Chem., 1992, pp. 24810-24018.

(Continued)

*Primary Examiner* — Lawrence E Crane
(74) *Attorney, Agent, or Firm* — Kilpatrick Townsend & Stockton LLP

(57) ABSTRACT

Methods of preparing synthetic oligonucleotides containing at least one phosphotriester linkage conjugated to a monosaccharide are disclosed, where the synthetic oligonucleotides are prepared from nucleosidic phosphoramidite building blocks, preferably followed by removal of protecting groups to provide monosaccharide-conjugated oligonucleotides.

27 Claims, 10 Drawing Sheets

Specification includes a Sequence Listing.

(56) References Cited

OTHER PUBLICATIONS

Matta et al., Carbohydrate Res., 1973, pp. 215-218.
Miller et al., "Alkyl phosphotriesters of dinucleotides and oligonucleotides. 4. Synthesis of oligodeoxyribonucleotide ethyl phosphotriesters and their specific complex formation with transfer ribonucleic acid", Biochemistry, 1974, pp. 4887-4896.
PCT/US2014/041133, "International Preliminary Report on Patentability", dated Dec. 17, 2015, 10 pages.
Pless, "Duplex formation of a nonionic oligo(deoxythymidylate) analogue (heptadeoxythymidylyl-(3'-5)-deoxythymidine heptaethyl ester (d-(Tp(Et))7T)) with poly(deoxyadenylate). Evaluation of the electrostatic interaction.", Biochemistry, 1977, pp. 1239-1250.
Sekine et al., "Essential Factors for Stabilization of the Predominant C3'-endo Conformation in Dinucleoside Phosphotriester Derivatives with Cyclonucleotide Bridge Structures at the Downstream 3'-Position", Eur. J. Org. Chem, 2001, pp. 1989-1999.
Sekine et al., "Synthesis and Properties of Oligonucleotides Having a Phosphorus Chiral Center by Incorporation of Conformationally Rigid 5'-Cyclouridylic Acid Derivatives", J. Org. Chem., 2000, pp. 6515-6524.
Sobkowski et al., "Studies on reactions of nucleoside H-phosphonate diesters with bifunctional reagents. Part 4. Chemoselectivity during oxidative coupling of nucleoside H-phosphonate diesters with amino alcohols controlled by protonation of the amino function", Tetrahedron Lett., 1995, pp. 2295-2298.
Song et al., "Use of silyl ethers as fluoride scavengers in RNA synthesis", Tetrahedron Lett., 1999, pp. 4653-4654.
Stawinski et al., "Stereospecific oxidation and oxidative coupling of H-phosphonate and H-phosphonothioate diesters", Tetrahedron Lett., 1992, pp. 3185-3188.

\* cited by examiner

PHOSPHORAMIDITE BUILDING BLOCKS FOR SUGAR-CONJUGATED OLIGONUCLEOTIDES

CROSS-REFERENCE TO RELATED APPLICATIONS

This application is a continuation of U.S. application Ser. No. 14/960,197, which is a continuation of international patent application number PCT/US2014/041133, which claims priority from U.S. application No. 61/831,521 filed on Jun. 5, 2013, each of which are hereby incorporated by reference in its entirety.

REFERENCE TO A "SEQUENCE LISTING," A TABLE, OR A COMPUTER PROGRAM LISTING APPENDIX SUBMITTED AS AN ASCII FILE

The instant application contains a Sequence Listing which has been submitted via EFS-Web and is hereby incorporated by reference herein in its entirety. Said ASCII copy, created on Aug. 3, 2018, is named "095111-1099045_ST25.txt" and is 23,775 bytes in size.

BACKGROUND OF THE INVENTION

1. Field of the Invention

In one aspect, this invention is directed to methods for the preparation of oligonucleotides conjugated to at least one sugar moiety. In the other aspect, the invention provides methods for preparation of protected forms of oligonucleotides wherein at least one of the internucleosidic phosphate moieties is converted to its phosphate triester analog and to compounds useful in preparation of such protected oligonucleotides. Oligonucleotides prepared by the methods of the invention are useful for therapeutic and diagnostic applications and as research reagents.

2. Summary of the Related Art

It is well known, however, that oligonucleotides and their phosphorothioate analogues are of limited stability in blood and tissues. Also, since such compounds are negatively charged they lack the ability to efficiently permeate biological membranes. Thus, both their oral bioavailability and cellular uptake are usually low. To overcome this problem, several types of modified oligonucleotides have been introduced. Among such oligonucleotides, backbone modified neutral oligonucleotides, phosphate triester analogs, have gained wide recognition.

To date, the art recognizes simple alkyl triester analogs, methyl phosphotriester analogs disclosed in U.S. Pat. No. 5,955,599, and ethyl phosphotriester analogs disclosed in Pless, R. C.; Ts'o, P. O. P. *Biochemistry* 1977, 16 (6), 1239-1250; Miller, P. S.; Barrett, J. C.; Ts'o, P. O. P. *Biochemistry* 1974, 13 (24), 4887-96; Lesser, D. R.; et al. *J Biol. Chem.* 1992, 267 (34), 24810-18; and Stawinski, J.; et al. *Tetrahedron Lett.* 1992, 33 (22), 3185-8. More complex, O-acyloxyaryl triester analogs have been disclosed in Iyer, R. P.; et al. *Bioorg. Med. Chem. Lett.* 1997, 7 (7), 871-876. Further development was presented by acylaminoethyl analogs disclosed in U.S. Pat. Nos. 6,121,437, 6,610,837, US 2001/0044529, WO 2003/048179, and WO 2006/065751. (Pivaloylthio)ethyl triester analogs have been disclosed in U.S. Pat. No. 6,919,437. The latter modification has been even further developed with the introduction of extended side chains to replace the ethyl fragment as disclosed in WO2010/039543 and in WO2014/031575. Several other, less developed, embodiments of triester analogs have been reported in Sekine, M.; et al. *Eur. J. Org. Chem.* 2001, (10), 1989-1999; Sekine, M.; et al. *J. Org. Chem.* 2000, 65 (20), 6515-6524; Sobkowski, M.; et al. *Tetrahedron Lett.* 1995, 36 (13), 2295-8; Ayukawa, H.; et al. *Chemistry Lett.* 1995, (1), 81.

The common feature of the analogs disclosed in the prior art was that the elimination of negative charge from the backbone of modified oligonucleotides led to the loss of solubility of said oligonucleotides in aqueous media, which is highly desirable for their successful use in biological applications.

SUMMARY OF THE INVENTION

Those skilled in the art will appreciate the fact that natural carbohydrates, particularly mono- and oligosaccharides, are characterized by a high degree of solubility in aqueous media. Should mono- or oligosaccharides be artificially conjugated to compounds of low solubility, this property may be used for the benefit of dissolution of the compounds in aqueous systems.

Several processes for the solid phase synthesis of oligonucleotide compounds are known to those skilled in the art and may be employed with the present invention. Exemplary processes are disclosed in U.S. Pat. No. 4,458,066 issued on Jul. 3, 1984, U.S. Pat. No. 4,500,707 issued on Feb. 19, 1985, and U.S. Pat. No. 5,132,418 issued on Nov. 27, 1990.

A process for the preparation of phosphoramidite building blocks is disclosed in U.S. Pat. No. 4,415,732 issued on Nov. 15, 1983. Certain nucleoside phosphoramidite compounds are disclosed in U.S. Pat. No. 4,668,777 issued on May 26, 1987.

It is an object of this invention to provide novel compounds which may serve as building blocks for the preparation of oligomeric compounds, phosphotriester analogs of natural oligonucleotides, wherein a carbohydrate moiety is linked to the internucleosidic phosphate residue.

It is a further object of the present invention to provide novel oligomeric compounds, phosphotriester analogs of natural oligonucleotides with improved physico-chemical properties, wherein a carbohydrate moiety is linked to the internucleosidic phosphate residue.

It is a further object of this invention to provide methods for synthetic preparation of said oligomeric compounds.

Other objects of this invention will be apparent to those skilled in the art.

These objects are satisfied by the present invention which provides novel nucleoside phosphoramidite reagents useful in preparation of oligomeric compounds and methods for making such oligomeric compounds.

Abbreviations

As used herein:
Ac is Acetyl;
Bz is benzoyl;
DCM is dichloromethane;
dmf is N,N-dimethylformamidino;
iPrPac is (4-isopropylphenoxy)acetyl;
MeCN is acetonitrile;
Pac is phenoxyacetyl;
TEA is triethylamine;
NMI is N-methylimidazol;
HPLC is high-performance liquid chromatography; and
ES-MS is mass-spectrometry with electron-spray ionization.

DETAILED DESCRIPTION OF THE INVENTION

Figure 1:
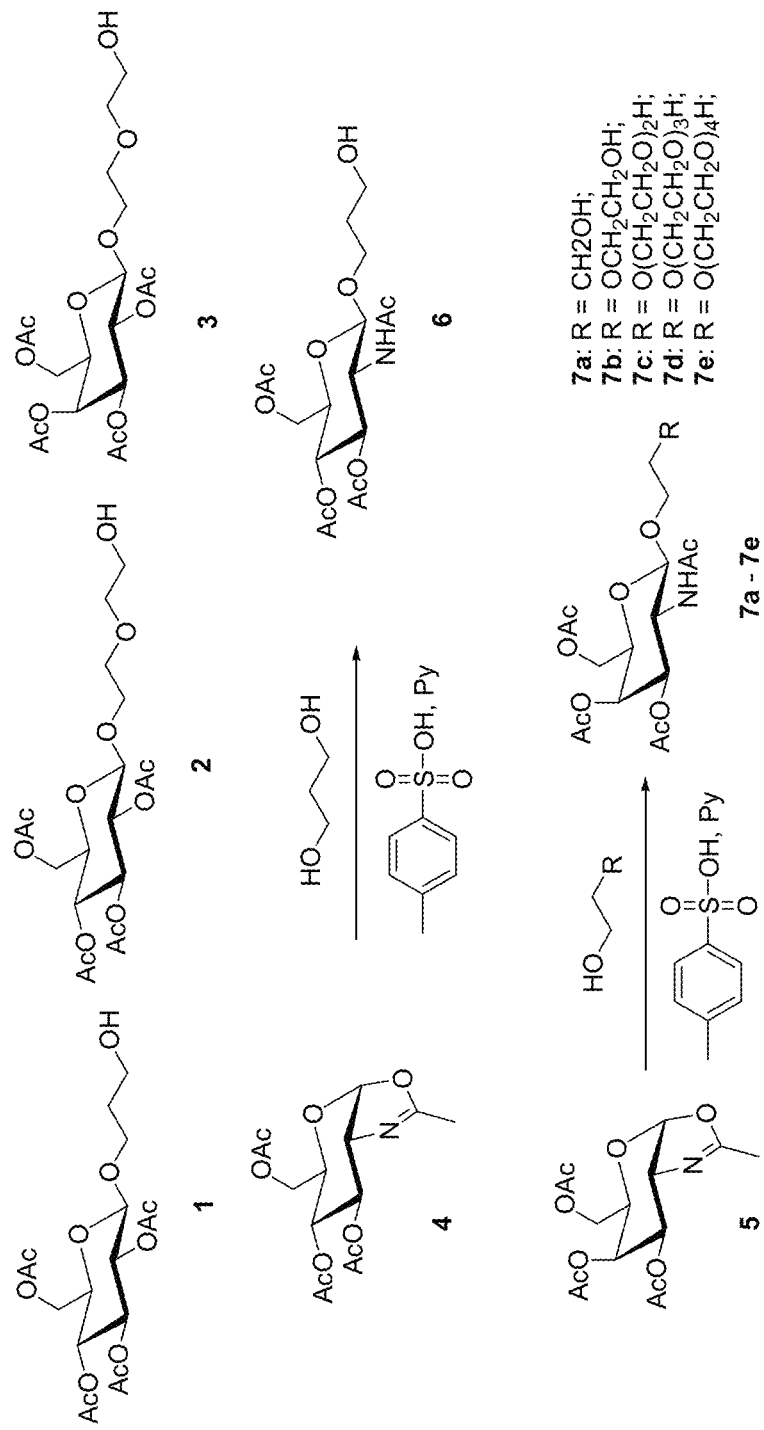
FIG. 1 shows structures of compounds 1, 2, and 3 and a synthetic scheme for the preparation of compounds 7a-7e.

In a first aspect, the invention provides novel compounds which may serve as building blocks for preparation of oligomeric compounds, phosphotriester analogs of natural oligonucleotides, wherein a carbohydrate moiety is linked to the internucleosidic phosphate residue according to Formula I:

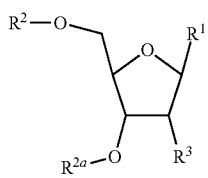

Formula I wherein:
R$^1$ is an optionally protected nucleic base selected from adenine, cytosine, guanine, thymine, uracil, 2-aminoadenine, N6-methyladenine, 7-deazaadenine, 7-deaza-8-azaadenine, 8-aminoadenine, 5-methylcytosine, N4-ethylcytosine, 7-deazaguanine, 7-deaza-8-azaguanine, 8-aminoguanine, 7-deazaxanthyne, or hypoxanthine;

one of R$^2$ and R$^{2a}$ is a protecting group of trityl type including but not limited to (4-methoxyphenyl)diphenylmethyl, bis-(4-methoxyphenyl)phenylmethyl, tris-(methoxyphenyl)methyl, 9-phenylxanthen-9-yl, or 9-(p-methoxyphenyl)xanthen-9-yl, and the other is a phosphoramidite moiety:

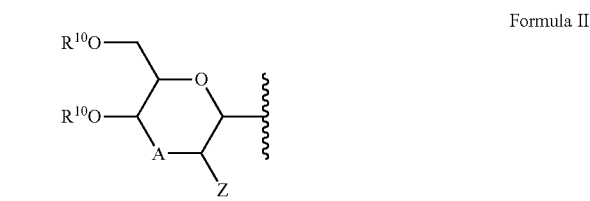

wherein:
each R$^4$ and R$^5$ is, independently, C$_1$ to C$_6$ alkyl, or R$^4$ and R$^5$ together with the nitrogen atom they are attached form a cycle wherein R$^4$+R$^5$=(CH$_2$)$_n$X(CH$_2$)$_m$,
wherein:
X is an atom of oxygen or CH$_2$ group;
each n and m is, independently, an integer from 2 to about 5;
L is a linking moiety —[(CH$_2$)$_p$Y(CH$_2$)$_q$]$_r$—,
wherein:
each p, q, and r is, independently, an integer from 1 to 18;
Y is a chemical bond, oxygen atom, sulfur atom, NQ$^1$, —N(Q$^1$)C(=O)N(Q$^2$)—, —C(=O)N(Q$^1$)—, or —N(Q$^1$)C(=O)—,
wherein:
each Q$^1$ and Q$^2$ is independently hydrogen atom, methyl group, ethyl group, propyl group, isopropyl group, acetyl group, trifluoroacetyl group, phenoxyacetyl group, benzoyl group, or 9-fluorenylmethyloxycarbonyl group;
R$^6$ is a substituted monosaccharide residue of general Formula II Formula II ![Formula II structure]

wherein:
each R$^{10}$ is, independently, an acyl protecting group including but not limited to acetyl, propionyl, butyryl, isobutyryl, pivaloyl, benzoyl, or 4-methylbenzoyl groups, a trityl-type protecting group including but not limited to (4-methoxyphenyl)diphenylmethyl, bis-(4-methoxyphenyl)phenylmethyl, tris-(methoxyphenyl)methyl, 9-phenylxanthen-9-yl, or 9-(p-methoxyphenyl)xanthen-9-yl, a silyl protecting group including but not limited to triisopropylsilyl, t-butyldimethylsilyl, t-butyldiphenylsilyl, triphenylsilyl, or diphenylmethylsilyl, an alkyl group containing from 1 to 18 atoms of carbon, a benzyl group, a 4-methoxybenzyl group, a propargyl group, or another substituted monosacharide residue of Formula II;

A is a chemical bond or CHOR$^{10}$;
Z is a hydrogen, OR$^{10}$, or N(Q$^2$)Q$^3$ wherein:
each Q$^2$ and Q$^3$ is, independently, hydrogen atom, methyl group, ethyl group, propyl group, isopropyl group, acetyl group, trifluoroacetyl group, phenoxyacetyl group, benzoyl group, or 9-fluorenylmethyloxycarbonyl group;
R$^3$ is hydrogen atom, fluorine atom, substituted hydroxy group OR$^7$, or substituted amino group NR$^8$R$^9$, wherein:

R⁷ is a $C_1$ to $C_6$ alkyl, 2-alkoxyethyl group, or N-methylcarboxamidomethyl group; and each $R^8$ and $R^9$ is, independently, hydrogen atom, methyl group, ethyl group, propyl group, isopropyl group, acetyl group, trifluoroacetyl group, phenoxyacetyl group, benzoyl group, or 9-fluorenylmethyloxycarbonyl group.

In an embodiment of the present invention, $R^1$ of Formula I is a nucleic base selected from $N^6$-benzoyladenine, $N^6$-phenoxyacetyladenine, $N^6$-(4-isopropylphenoxy)acetyladenine, adenine, $N^4$-benzoylcytosine, $N^4$-acetylcytosine, $N^4$-phenoxyacetylcytosine, $N^4$-(4-isopropylphenoxy)acetylcytosine, $N^4$-benzoyl-4-methylcytosine, $N^4$-acetyl-4-methylcytosine, cytosine, $N^4$-phenoxyacetyl-4-methylcytosine, $N^4$-(4-isopropylphenoxy)acetyl-4-methylcytosine, 4-methylcytosine, $N^2$-isobutyrylguanine, $N^2$-phenoxyacetylguanine, $N^2$-(4-isopropylphenoxy)acetylguanine, $N^2$—(N,N-dimethylformamidino)guanine, guanine, thymine, or uracil.

In another embodiment, $R^2$ of Formula I is 4,4'-dimethoxytrityl group and $R^{2a}$ is

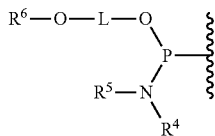

In yet another embodiment, $R^{2a}$ of Formula I is 4,4'-dimethoxytrityl group and $R^2$ is

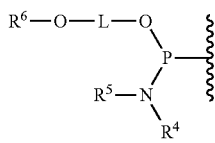

In yet another embodiment of the present invention, $R^3$ of Formula I is hydrogen.

In yet another embodiment of the present invention, $R^3$ of Formula I is $OCH_3$.

In yet another embodiment of the present invention, $R^3$ of Formula I is fluorine.

In yet another embodiment of the present invention, each $R^4$ and $R^5$ of Formula I is isopropyl group.

In yet another embodiment of the present invention, L of Formula I is —$(CH_2)_3$—.

In yet another embodiment of the present invention, L of Formula I is —$(CH_2)_4$—.

In yet another embodiment of the present invention, L-O of Formula I is —$[(CH_2)_2—O]_2$—.

In yet another embodiment of the present invention, L-O of Formula I is —$[(CH_2)_2—O]_3$—.

In yet another embodiment of the present invention, L-O of Formula I is —$[(CH_2)_2—O]_4$—.

In yet another embodiment of the present invention, L-O of Formula I is —$[(CH_2)_2—O]_5$—.

In yet another embodiment of the present invention, $R^6$ of Formula I is a protected β-D-glucopyranoside.

In yet another embodiment of the present invention, $R^6$ of Formula I is a protected β-D-galactopyranoside.

In yet another embodiment of the present invention, $R^6$ of Formula I is a protected 2-amino-2-deoxy-β-D-glucopyranoside.

In still another embodiment of the present invention, $R^6$ of Formula I is a protected 2-amino-2-deoxy-β-D-glucopyranoside wherein one of $Q^2$ and $Q^3$ is hydrogen, and the other is an acetyl group.

In a further embodiment of the present invention, $R^6$ of Formula I is a protected 2-amino-2-deoxy-β-D-galactopyranoside.

In a still further embodiment of the present invention, $R^6$ of Formula I is a protected 2-amino-2-deoxy-β-D-galactopyranoside wherein one of $Q^2$ and $Q^3$ is hydrogen, and the other is an acetyl group.

In yet another embodiment of the present invention, each $R^{10}$ of Formula II is an acetyl group.

In yet another embodiment of the present invention, each $R^{10}$ of Formula II is a benzoyl group.

In yet another embodiment of the present invention, each $R^{10}$ of Formula II is a butyryl group.

In yet another embodiment of the present invention, each $R^{10}$ of Formula II is an isobutyryl group.

In yet another embodiment of the present invention, each $R^{10}$ of Formula II is a propionyl group.

In yet another embodiment of the present invention, each $R^{10}$ of Formula II is a 4-methylbenzoyl group.

In yet another preferred embodiment of the present invention, one of $R^{10}$ of Formula II is another protected monosaccharide residue of Formula II, and each of the other $R^{10}$ is an acetyl group.

In a second aspect, the present invention provides novel oligomeric compounds, phosphotriester analogs of natural oligonucleotides, having the structure according to Formula III wherein a carbohydrate moiety is linked to the internucleosidic phosphate residue:

Formula III

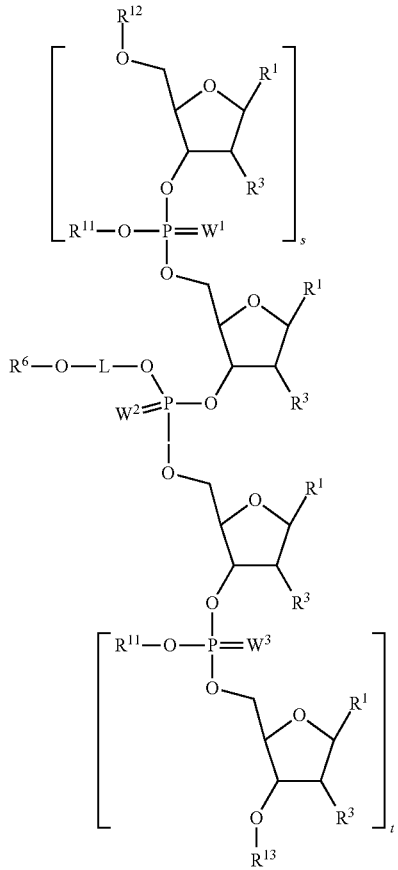

wherein:
each $R^1$ is independently an optionally protected nucleic base selected from adenine, cytosine, guanine, thymine, uracil, 2-aminoadenine, N6-methyladenine, 7-deazaadenine, 7-deaza-8-azaadenine, 8-aminoadenine, 5-methylcytosine, N4-ethylcytosine, 7-deazaguanine, 7-deaza-8-azaguanine, 8-aminoguanine, 7-deazaxanthyne, or hypoxanthine;
each $R^3$ is, independently, hydrogen atom, fluorine atom, substituted hydroxy group $OR^7$, or substituted amino group $NR^8R^9$,
wherein:
each $R^7$ is, independently, a $C_1$ to $C_6$ alkyl, 2-alkoxyethyl group, or N-methylcarboxamidomethyl group;
each $R^8$ and $R^9$ is, independently, hydrogen atom, methyl group, ethyl group, propyl group, isopropyl group, acetyl group, trifluoroacetyl group, phenoxyacetyl group, benzoyl group, or 9-fluorenylmethyloxycarbonyl group;
L is a linking moiety $-[(CH_2)_pY(CH_2)_q]_r-$,
wherein:
each p, q, and r is, independently, an integer from 1 to 18;
Y is a chemical bond, oxygen atom, sulfur atom, $NQ^1$, $-N(Q^1)C(=O)N(Q^2)-$, $-C(=O)N(Q^1)-$, or $-N(Q^1)C(=O)-$,
wherein:
each $Q^1$ and $Q^2$ is independently hydrogen atom, methyl group, ethyl group, propyl group, isopropyl group, acetyl group, trifluoroacetyl group, phenoxyacetyl group, benzoyl group, or 9-fluorenylmethyloxycarbonyl group;
each $R^6$ is, independently, a substituted monosaccharide residue of general Formula II,
wherein:
each $R^{10}$ is, independently, an acyl protecting group including but not limited to acetyl, propionyl, butyryl, isobutyryl, pivaloyl, benzoyl, and 4-methylbenzoyl groups, a trityl-type protecting group including but not limited to (4-methoxyphenyl)diphenylmethyl, bis-(4-methoxyphenyl)phenylmethyl, tris-(methoxyphenyl)methyl, 9-phenylxanthen-9-yl, and 9-(p-methoxyphenyl)xanthen-9-yl, a silyl protecting group including but not limited to triisopropylsilyl, t-butyldimethylsilyl, t-butyldiphenylsilyl, triphenylsilyl, and diphenylmethylsilyl, an alkyl group containing from 1 to 18 atoms of carbon, a benzyl group, a 4-methoxybenzyl group, a propargyl group, or another substituted monosacharide residue of Formula II;
A is a chemical bond or $CHOR^{10}$;
Z is a hydrogen, $OR^{10}$, or $N(Q^2)Q^3$ wherein:
each $Q^2$ and $Q^3$ is, independently, hydrogen atom, methyl group, ethyl group, propyl group, isopropyl group, acetyl group, trifluoroacetyl group, phenoxyacetyl group, benzoyl group, or 9-fluorenylmethyloxycarbonyl group;
each $R^{11}$ is independently a negative charge compensated by a cation, a phosphate protecting group, or $R^6O-L-$;
each $R^{12}$ and $R^{13}$ is, independently, hydrogen atom, a protecting group selected from (4-methoxyphenyl)diphenylmethyl, bis-(4-methoxyphenyl)phenylmethyl, tris-(methoxyphenyl)methyl, 9-phenylxanthen-9-yl, or 9-(p-methoxyphenyl)xanthen-9-yl; or a point of attachment to solid phase material with the proviso that $R^{12}$ and $R^{13}$ are not both simultaneously a linker connected to a solid support;

each $W^1$, $W^2$, and $W^3$ is independently oxygen or sulfur; and
each s and t is, independently, an integer from 0 to about 100.

In a third aspect, the present invention provides methods for synthetic preparation of oligomeric compounds according to Formula III, said method comprising:
reacting a compound of Formula I with a compound of Formula IV containing at least one reactive hydroxy group wherein the compound of Formula IV has the structure:

FORMULA IV

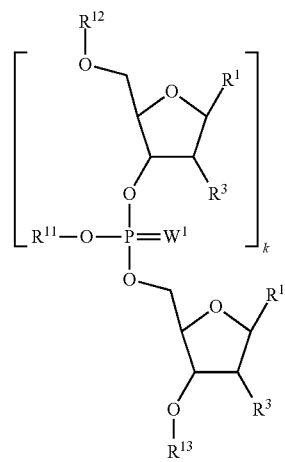

wherein:
one of $R^{12}$ and $R^{13}$ is a hydrogen atom, and the other is a protecting group or a linker connected to a solid support; and
k is an integer selected from 0 to about 100.

In an embodiment, the method further comprises treating the oligomeric compound with a reagent under conditions of time, temperature, and pressure effective to oxidize or sulfurize the oligomeric compound.

In an embodiment, the method further comprises treating the oligomeric compound with a reagent under conditions of time, temperature, and pressure effective to deprotect the oligomeric compound.

In an embodiment, wherein $R^{13}$ is a linker connected to a solid support, the method further comprises treating the oligomeric compound with a reagent under conditions of time, temperature, and pressure effective to remove the oligomeric compound from the solid support.

Certain of the starting materials used in the practice of the present invention are protected nucleosides 8, 9a-9c, 10a-10d, and 1a-11d, which are readily available from commercial sources (such as, for example, ChemGenes, Inc., Waltham, Mass.; Rasayan, Inc., Encinitas, Calif.).

Certain other starting materials used in the practice of the present invention are readily prepared following methods and procedures familiar to those skilled in the art and disclosed in the chemical literature. Compounds 1, 2, and 3 (FIG. 1) were prepared as disclosed in Karjala, S. and Link, K. P., *J. Amer. Chem. Soc.*, 1940, 62, 917-922. Compound 4 (FIG. 1) was prepared as disclosed in Fukase, K; et al. *Bull. Chem. Soc. Japan* 2003, 76, 485-500, and compound 5 (FIG. 1) was prepared as disclosed in Matta, K. L.; et al. *Carbohydrate Res.* 1973, 26, 215-218.

Compounds 6b and 7a-7e were prepared as disclosed in FIG. 1 from compounds 4 and 5 and ethyleneglycol, di- tri- tetra- and pentaethyleneglycols.

Figure 2:
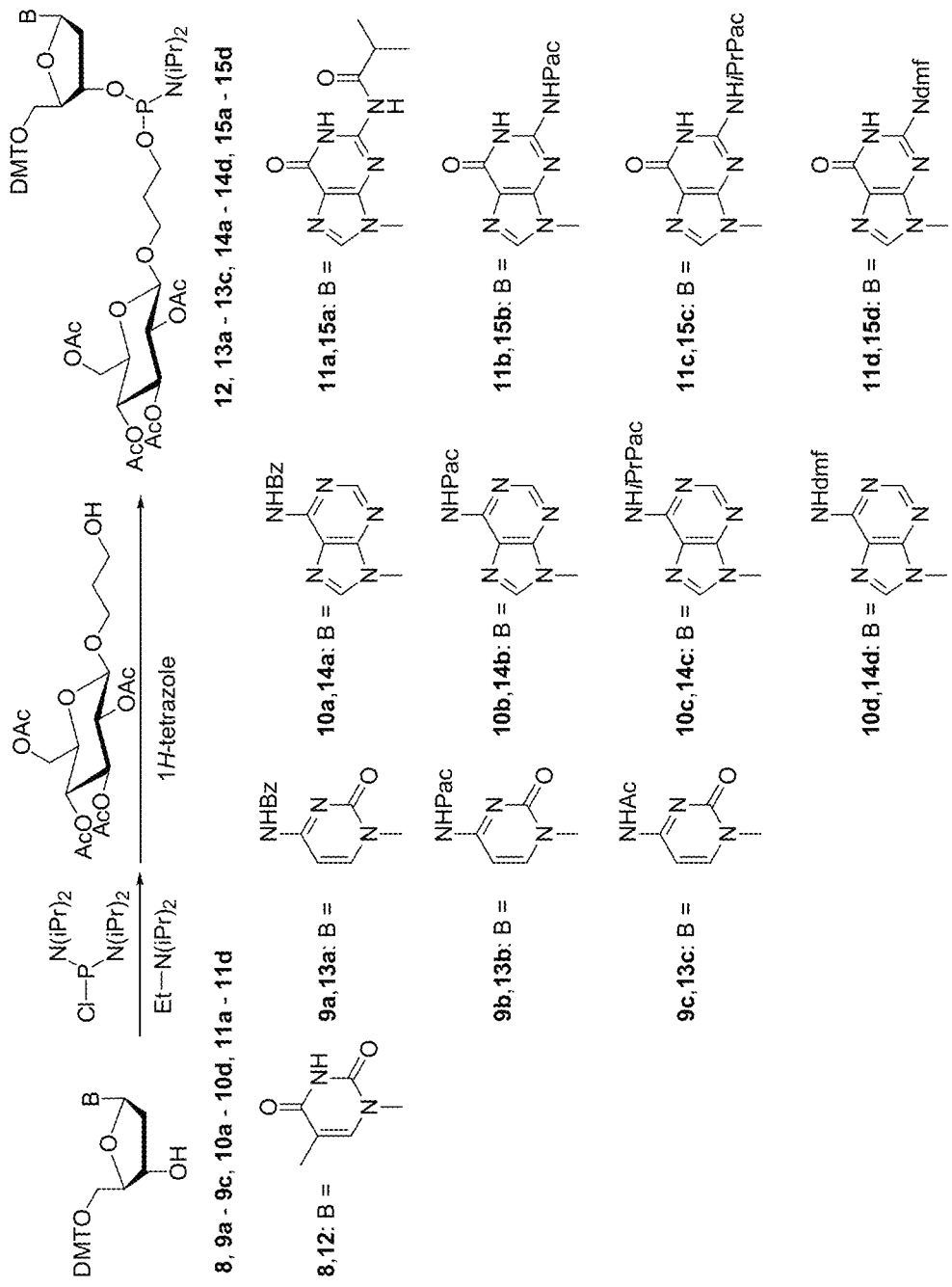
FIG. 2 shows a synthetic scheme for the preparation of compounds 12, 13a-13c, 14a-14d, and 15a-15d.

As illustrated in FIG. 2, exemplary phosphoramidite building blocks 12, 13a-13c, 14a-14d, 15a-15d comprising a protected β-D-glucopyranose moiety attached to the phosphite function via a $C_3$-spacer arm may be readily synthesized from protected 2'-deoxynucleosides 8, 9a-9c, 10a-10d, and 11a-11d and 3-hydroxypropyl 2,3,4,6-tetra-O-acetyl-β-D-glucopyranoside 1.

To synthesize compounds 12, 13a-13c, 14a-14d, 15a-15d, the respective protected 2'-deoxynucleoside 8, 9a-9c, 10a-10d, and 11a-11d was first treated with bis(N,N-diisopropylamino) chlorophosphite (R. I. Chemical, Orange, Calif.) in the presence of excess N-ethyl-N,N-diisopropylamine (Alfa Aesar, Ward Hill, Mass.) in MeCN at −20° C. followed by stirring at room temperature for 1 to 2 h. The obtained solution of protected nucleoside-3'-O-bis(N,N-diisopropylamino) phosphite was further treated with compound 1 and 1H-tetrazole (Glen Research, Sterling, Va.) for 14 h at room temperature. Quenching with 5% aqueous $NaHCO_3$ followed by the standard work-up and purification by chromatography on a silica gel column afforded the desired phosphoramidite building blocks 12, 13a-13c, 14a-14d, 15a-15d.

Among these compounds, phosphoramidite building blocks 13a, 14a, and 15a feature the standard protecting scheme for exocyclic amino groups of nucleic bases.

Figure 3:
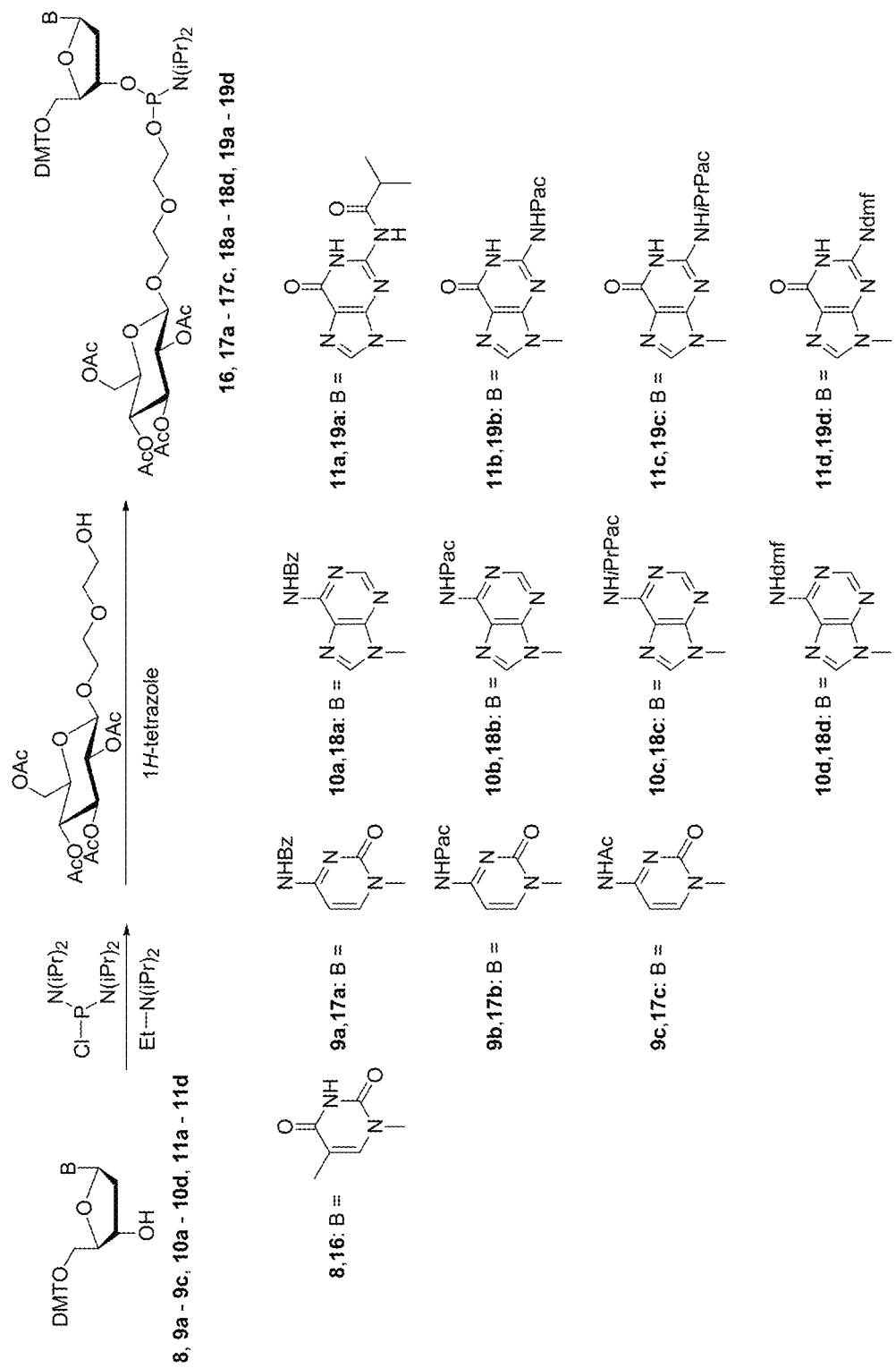
FIG. 3 shows a synthetic scheme for the preparation of compounds 16, 17a-17c, 18a-18d, and 19a-19d.

The method described above is also applicable to a peracetylated β-D-glucopyranoside-bearing ethyleneglycol spacer arm. FIG. 3 illustrates a reaction of protected nucleosides 8, 9a-9c, 10a-10d, and 11a-11d with 2-[(2-hydroxyethyl)oxy]ethyl 2,3,4,6-tetra-O-acetyl-β-D-glucopyranoside 2. Following the procedure described above gave the phosphoramidite building blocks 16, 17a-17c, 18a-18d, 19a-19d featuring a diethyleneglycol spacer arm.

Figure 4:
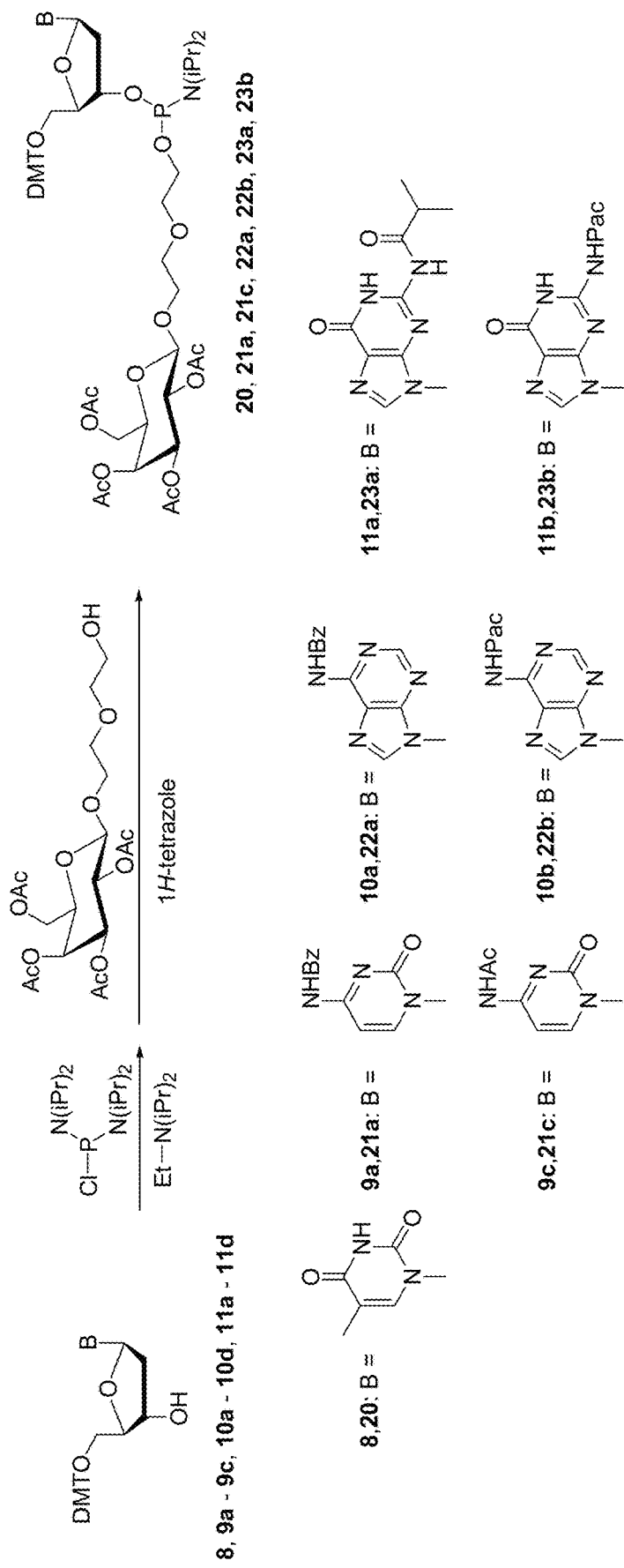
FIG. 4 shows a synthetic scheme for the preparation of compounds 20, 21a, 21c, 22a, 22b, 23a, and 23b.

In certain embodiments, it is desirable to introduce monosaccharide residues other than glucose into oligonucleotides. By following the general synthetic method described above, the preparation of phosphoramidite building blocks 20, 21a, 21c, 22a, 22b, 23a, and 23b derivatized with a peracetylated β-D-galactospyranoside residue and ethyleneglycol spacer arm was accomplished by reacting protected nucleosides 8, 9a-9c, 10a-10d, 11a-11d with compound 3 (see FIG. 4).

Figure 5:
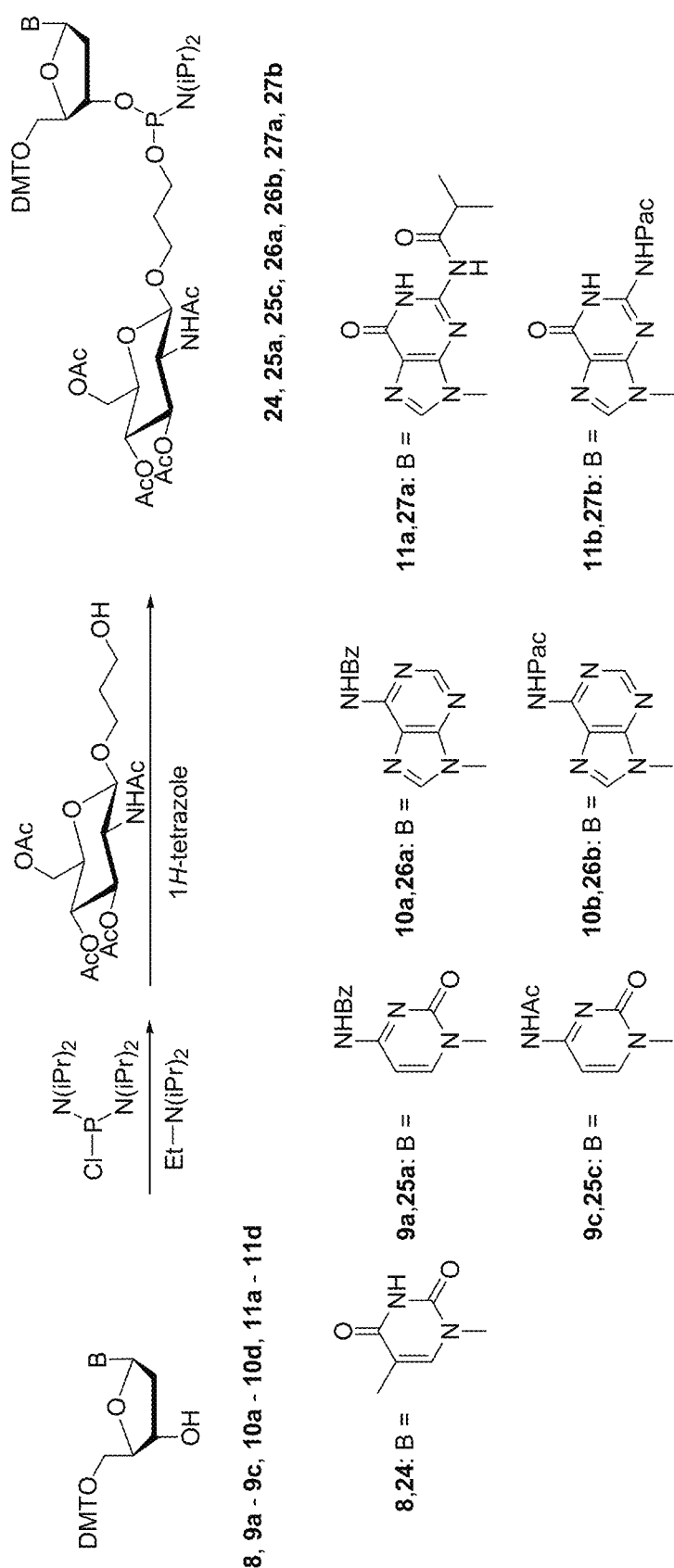
FIG. 5 shows a synthetic scheme for the preparation of compounds 24, 25a, 25c, 26a, 26b, 27a, and 27b.

By following the general synthetic method described above, the preparation of phosphoramidite building blocks 24, 25a, 25c, 26a, 26b, 27a, and 27b derivatized with a protected N-acetyl-D-glucosamine residue and C3 spacer arm was accomplished by reacting protected nucleosides 8, 9a-9c, 10a-10d, 1a-1d with compound 6 (see FIG. 5).

Figure 6:
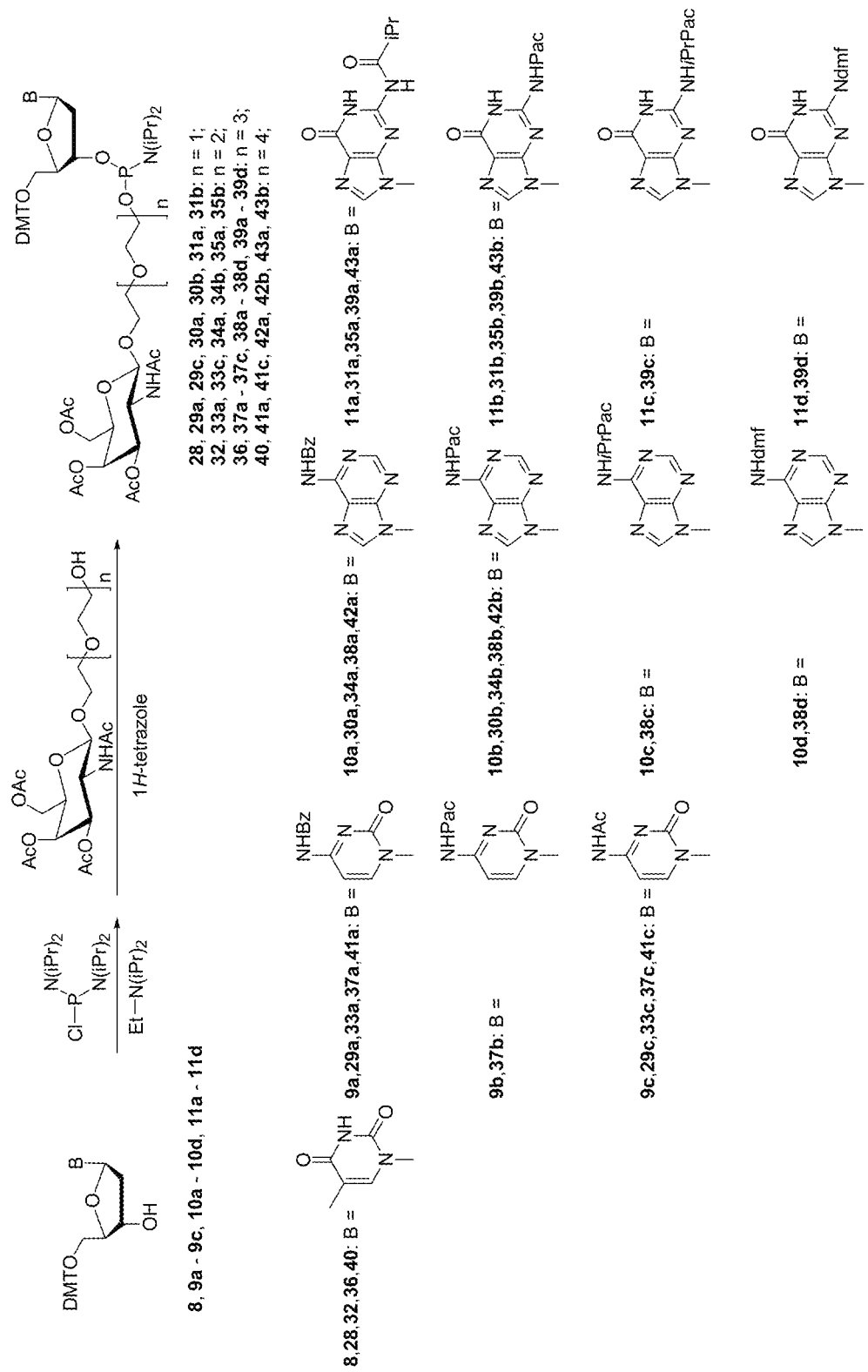
FIG. 6 shows a synthetic scheme for the preparation of compounds 28, 29a, 29c, 30a, 30b, 31a, 31b, 32, 33a, 33c, 34a, 34b, 35a, 35b, 36, 37a-37c, 38a-38d, 39a-39d, 40, 41a, 41c, 42a, 42b, 43a, and 43b.

Analogously, the preparation of phosphoramidite building blocks 28, 29a, 29c, 30a, 30b, 31a, 31b, 32, 33a, 33c, 34a, 34b, 35a, 35b, 36, 37a-37c, 38a-38d, 39a-39d, 40, 41a, 41c, 42a, 42b, 43a, and 43b derivatized with protected N-acetyl-D-galactosamine residues starting from protected nucleosides 8, 9a-9c, 10a-10d, and 11a-11d and compounds 7a-7e is described in FIG. 6. The phosphoramidite reagents of this series feature oligoethyleneglycol linkers of various lengths to allow the placement of the monosaccharide residue at different distances from polyphosphate backbone of oligonucleotides.

Figure 7:
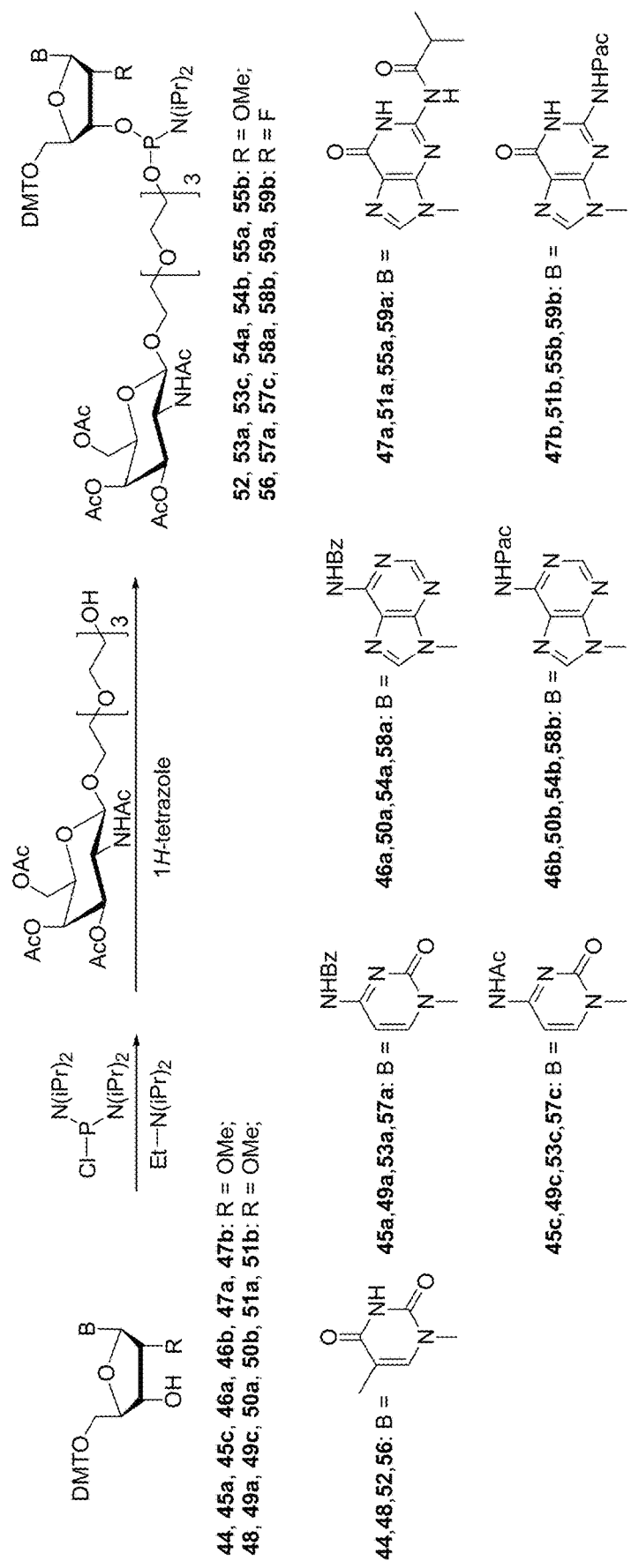
FIG. 7 shows a synthetic scheme for the preparation of compounds 52, 53a, 53c, 54a, 54b, 55a, 55b, 56, 57a, 57c, 58a, 58b, 59a, and 59b.

In certain embodiments of the invention, synthetic oligonucleotides bearing nucleotide residues derivatized at the 2'-position of the ribose ring are desirable due to their enhanced base-pairing properties. Those skilled in the art recognize that 2'-OMe and 2'-fluoro substitution at the ribose ring results in the enhancement of hybridization affinity of derivatized oligonucleotides to the complementary strands of oligonucleotides or nucleic acids. FIG. 7 describes the preparation of exemplary phosphoramidite building blocks 52, 53a, 53c, 54a, 54b, 55a, and 55b derived from 2'-O-methylnucleosides 44, 45a, 45c, 46a, 46b, 47a, 47b and phosphoramidite building blocks 56, 57a, 57c, 58a, 58b, 59a, and 59b derived from 2'deoxy-2'-fluoronucleosides 48, 49a, 49c, 50a, 50b, 51a, and 51b. All compounds 52-59 comprise a peracetylated D-galactosamine residue and tetraethyleneglycol spacer arm.

It is well known in the art that the standard conditions of oligonucleotide deprotection comprise treating a solid support-bound, protected oligonucleotide with 28-33% aqueous ammonium hydroxide for 8 h at 55° C. In certain embodiments of the present invention, compounds 13a, 14a, 15a, 17a, 18a, 19a, 21a, 22a, 23a, 25a, 26a, 27a, 29a, 30a, 31a, 33a, 34a, 35a, 41a, 42a, 43a, 53a, 54a, 55a, 57a, 58a, and 59a, are designed to be used within the standard deprotection strategy. However, certain oligonucleotides comprising unnatural nucleosidic residues may demonstrate a rather low stability under the standard conditions.

Various protecting schemes have been developed in order to remove the protecting groups under milder conditions. These works have been expertly reviewed in Beaucage, S. L. and Iyer, R. P. *Tetrahedron* 1992, 48, 2223-2311 and Beaucage, S. L. and Iyer, R. P. *Tetrahedron* 1993, 49, 6123-6194 and references referred to therein, all of which are herein incorporated by reference. In order to satisfy the requirements of alternative deprotection schemes, the building blocks bearing $C^{Ac}$, $A^{dmf}$, and $G^{dmf}$ protected bases as, for instance, in compounds 13c, 14d, and 15d, are compatible with mild deprotecting strategies of oligonucleotide synthesis. The building blocks bearing $C^{Pac}$, $A^{Pac}$, $A^{iPrPac}$, $G^{Pac}$, and $G^{iPrPac}$ protected bases as, for instance, in compounds 13b, 14b, 14c, 15b, and 15c were prepared to be compatible with ultra-mild deprotecting strategies.

Figure 8:
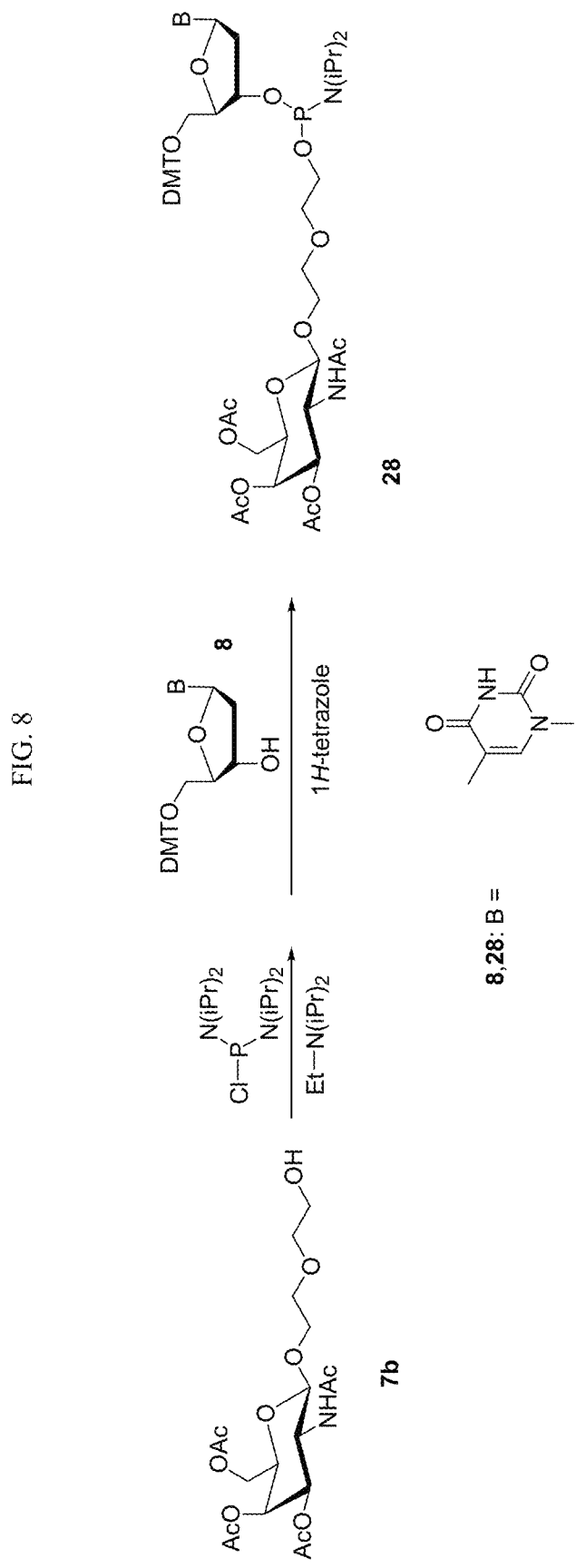
FIG. 8 shows an alternative synthetic scheme for the preparation of compound 28.

The present disclosure is not limited by the methods described in FIGS. 1-7. For example, an alternative method is exemplified in FIG. 8 by the preparation of phosphoramidite building block 28. Treatment of compound 7b with bis(N,N-diisopropylamino) chlorophosphite in the presence of N-ethyl-N,N-diisopropylamine gave a phosphorodiamidite compound. After purification on a silica gel column, the resulting compound was reacted with protected nucleoside 8 to give the desired phosphoramidite building block 28.

Most phosphoramidite building blocks described herein were isolated as solid foams or, in the case of compounds comprising tetraethyleneglycol and pentaethyleneglycol spacer, arms, as colorless oils sufficiently stable to be stored for several months at −18° C.

The hydrolysis of phosphoramidite building blocks 12 and 16 in 95% aqueous MeCN at 25° C. was followed by reverse-phase HPLC. It was determined that, under the conditions used, the half-life of compounds 12 and 16 was 48 and 33 h, respectively. This demonstrates that solutions of phosphoramidite reagents according to the present invention can be safely stored on an oligonucleotide synthesizer for 2-3 days, which is sufficient for most applications.

The use of novel phosphoramidite building blocks described herein in solid phase synthesis of oligonucleotides is illustrated with respect to compound 12:

d(Tp Tp Tp Tp TT TTT T)

wherein internucleosidic phosphate linkages p are phosphotriester linkages with 1-[2-[[2-(β-D-glucopyranosyloxy) ethyl]oxy]ethyl] modification (SEQ ID NO:6).

Oligonucleotides 61-64 were synthesized by the phosphoramidite method. Briefly, a commercial solid support, DMT-T CPG1000 (1.0 µmol) was placed in a synthetic column and installed on ABI394 synthesizer. The standard synthetic cycle useful in assemblying oligonucleotides with phosphate backbone comprised the following steps:
  (a) detritylation of the solid phase-bound material with 3% dichloroacetic acid in dichloromethane followed by washing with acetonitrile;
  (b) coupling of nucleoside phosphoramidite building block (0.1 M in acetonitrile) required by the sequence to the solid support-bound material in the presence of 1H-tetrazole (0.45 M in acetonitrile);
  (c) capping of unreacted solid support-bound hydroxy groups with a mixture of acetic anhydride and N-methyl imidazole and
  (d) oxidation of the solid support-bound phosphite triester groups with iodine (0.05 M in a mixture of pyridine, tetrahydrofurane, water).

Preparation of oligonucleotide phosphorothioates was conducted as disclosed in U.S. Pat. No. 7,723,528. Accordingly, steps (a) and (b) remained as disclosed above. The iodine solution was replaced with a solution of N'-(3-thioxo-3H-1,2,4-dithiazol-5-yl)-N,N-dimethylmethanimidamide (0.025 M in pyridine). Upon completion of coupling step (b) and washing the solid phase with acetonitrile, the sulfurization step was conducted. The capping step followed the sulfurization. The cycle appropriate for the assembly of the desired oligonucleotide was repeated as required by the sequence in preparation.

The synthetic cycle for incorporation of the phosphoramidite building blocks described herein was different from those disclosed above in that the coupling time for the incorporation of all novel phosphoramidite building blocks was extended to 1 min.

Following the general procedures disclosed above, the parent, unmodified oligonucleotide 60, plus oligonucleotides 61-64 wherein Tp denotes the residues of thymidine-3'-[[(β-D-glucopyranosyl)oxy]propyl]phosphate 65, were assembled:

```
                                          (SEQ ID NO: 1)
60: TTT TTT TTT T, parent natural oligonucleotide, (SEQ ID NO: 2)
61: Tp TTT TTT TTT, (SEQ ID NO: 3)
62: (Tp)2 TTT TTT TT, (SEQ ID NO: 4)
63: (Tp)3 TTT TTT T,
and (SEQ ID NO: 5)
64: (Tp)4 TTT TTT.
```

To determine the optimal deprotection conditions, solid support-bound oligonucleotides 61-64 thus obtained were treated under the following conditions suitable for removing all phosphate- and base-protecting groups from synthetic oligonucleotides:
  A. Concentrated ammonium hydroxide, room temperature, 18 h;
  B. Concentrated aqueous ammonium hydroxide, 65° C., 8 h;
  C. 0.05 M $K_2CO_3$ in anhydrous MeOH, room temperature, 4 h;
  D. 0.5 M Piperidine in anhydrous acetonitrile, room temperature, 15 min, followed by a mixture of 1,2-diaminoethane and toluene (50:50 v/v), room temperature, 4 h;
  E. 25% Aqueous t-butylamine, 65° C., 4 h;
  F. Mixture of concentrated aqueous ammonium hydroxide and 40% aqueous methylamine (50:50 v/v), room temperature, 120 min.

Upon completion of the deprotection under the conditions A, B, E, and F, the liquid phase was collected and evaporated in vacuo to dryness. The residue was dissolved in water (1 mL) and analyzed by reverse-phase HPLC and by ES MS.

Upon completion of the deprotection under the condition C, the reaction mixtures were neutralized by addition of 0.25 M aqueous $NaH_2PO_4$ (250 µL per 1 mL of deprotection solution). The solid phase was spun down; the liquid phase was collected and analyzed as described above.

Upon completion of the deprotection under the condition D, the solid phase was spun down, and the liquid phase was discarded. The solid phase was washed with toluene (2×1 mL) and with acetonitrile (2×1 mL). The solid phase was suspended in water (1 mL) and the suspension was centrifugated. The liquid phase was collected and analyzed as described above.

The results of HPLC and LC-ES MS analysis showed that deprotection under conditions A, C, D, and F resulted in products containing over 95% of the desired oligonucleotides. In contrast, the use of the conditions B and E led to the formation of the parent oligonucleotide 60 (SEQ ID NO: 1) where the (glucopyranosyloxy)propyl modifier was removed from the phosphotriester moiety. A more detailed analysis of the crude oligonucleotide products showed that conditions A and C were the most appropriate for deprotection of phosphotriester-derivatized oligonucleotides.

In the next round of experiments, oligonucleotides 67-72 were assembled and deprotected under conditions A and C as described above:
  67: Tp Tp Tp Tp TT TTT T (SEQ ID NO: 6) wherein nucleoside phosphate moieties Tp are phosphotriester moieties 75 (FIG. 9) with 1-[2-[[2-(β-D-glucopyranosyloxy)ethyl]oxy]ethyl] modification;
  68: Tp Tp Tp Tp T Tp Tp Tp Tp T (SEQ ID NO: 7) wherein nucleoside phosphate moieties Tp are phosphotriester moieties 65 (FIG. 9) with 1-[3-(β-D-glucopyranosyloxy)propyl]modification;
  69: Tp Tp Tp Tp Tp Tp Tp Tp Tp T (SEQ ID NO: 8) wherein all nucleoside phosphate moieties Tp are phosphotriester moieties 65 (FIG. 9) with 1-[3-(β-D-glucopyranosyloxy)propyl] modification;
  70: Tp Tp Tp Tp Tp Tp Tp Tp Tp T (SEQ ID NO: 9) wherein all nucleoside phosphate moieties Tp are phosphotriester moieties 75 (FIG. 9) with 1-[2-[[2-(β-D-glucopyranosyloxy)ethyl]oxy]ethyl] modification;
  71: Tp Tp Tp Tp TT TTT T (SEQ ID NO: 10) wherein nucleoside phosphate moieties Tp are phosphotriester moieties 79 (FIG. 9) with 1-[2-[[2-(N-acetyl-2-deoxy-2-amino-β-D-galactopyranosyloxy) ethyl]oxy]ethyl] modification; and
  72: Tp Tp Tp Tp T Tp Tp Tp Tp T (SEQ ID NO: 11) wherein nucleoside phosphate moieties Tp are phosphotriester moieties 79 (FIG. 9) with 1-[2-[[2-(N-acetyl-2-deoxy-2-amino-β-D-galactopyranosyloxy) ethyl]oxy]ethyl] modification.

Analysis of crude oligonucleotide products by reverse-phase HPLC and LC-ES MS confirmed that both deprotection conditions A and C were appropriate for preparation of highly-modified 10-mer oligonucleotides 68, 69, 70, and 71 comprising 8 to 9 phosphotriester moieties, thus confirming the stability of the novel modification of internucleosidic phosphate groups disclosed in the present invention. Further comparison of HPLC profiles obtained for oligonucleotides 64, 67, and 71 revealed no appreciable difference in hydrolytic stability between nucleoside phosphate residues 65, 75, and 79 under the basic deprotection conditions.

Figure 9:
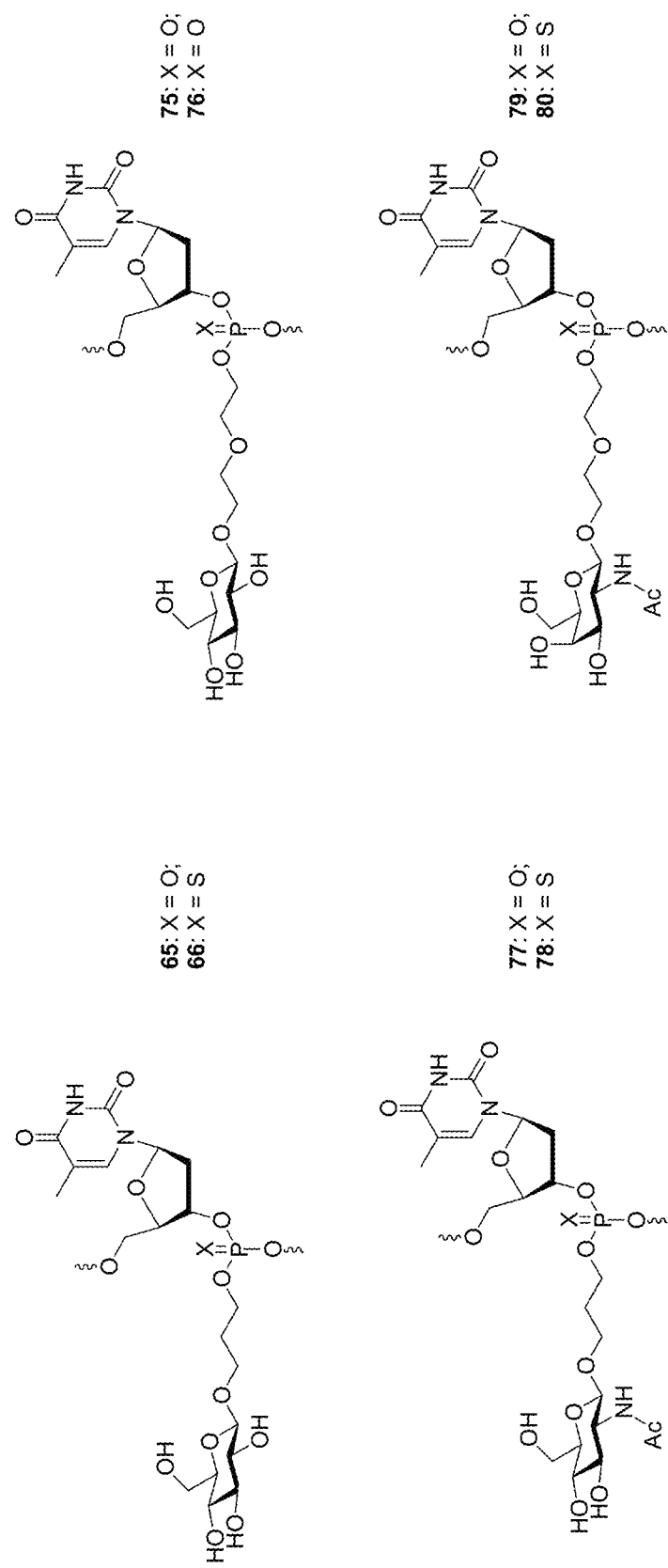
FIG. 9 shows phosphotriester nucleoside residues 65, 66, 75, 76, 77, 78, 79, and 80 incorporated into synthetic oligonucleotides.

Finally, full-length oligonucleotide phosphorothioates 81-84 were synthesized and deprotected under the condition A:

81: d(TGT GAG TAC CAC TGA TTC) (SEQ ID NO: 12) phosphorothioate wherein all internucleoside moieties are phosphorothioate triester moieties with 1-[3-(β-D-glucopyranosyloxy)propyl] modification as exemplified for the triester of thymidine-3'-monophosphorothioate by structure 66 (FIG. 9);

82: d(TpGpTp GAG TAC CAC TGAp TpTpA) (SEQ ID NO: 13) phosphorothioate wherein all internucleoside moieties are phosphorothioate moieties and Tp and Ap are phosphorothioate triester moieties with 1-[3-(N-acetyl-2-deoxy-2-amino-β-D-glucopyranosyloxy)propyl] modification as exemplified for the triester of thymidine-3'-monophosphorothioate by structure 78 (FIG. 9);

83: d(TpGpTp GAG TAC CAC TGAp TpTpA) phosphorothioate (SEQ ID NO: 14) wherein all internucleoside moieties are phosphorothioate moieties and Tp and Ap are phosphorothioate triester moieties with 1-[2-[[2-(N-acetyl-2-deoxy-2-amino-β-D-galactopyranosyloxy)ethyl]oxy]ethyl] modification as exemplified for the triester of thymidine-3'-monophosphorothioate by structure 80 (FIG. 9);

84: dTp dGp dTp GAG UAC CAC UG dAp dTp dTp dA phosphorothioate (SEQ ID NO: 15) wherein all internucleoside moieties are phosphorothioate moieties and Tp and Ap are phosphorothioate triester moieties with 1-[2-[[2-(N-acetyl-2-deoxy-2-amino-β-D-galactopyranosyloxy)ethyl]oxy]ethyl] modification as exemplified for the triester of thymidine-3'-monophosphorothioate by structure 80 (FIG. 9).

Oligonucleotide 81 was characterized by reverse-phase HPLC, and oligonucleotides 82-84 were characterized by reverse-phase HPLC, ion exchange HPLC, and LC-MS with electron-spray ionization. Importantly, oligonucleotides 68 and 72 bearing only one negative charge and 69, 70, and 81 wherein all negatively charged internucleosidic phosphates were replaced by neutral phosphotriested moieties were readily soluble in aqueous media.

Accordingly, the efficient preparation of monosaccharide-derivatized phosphotriester analogs of oligonucleotides and their phosphorothioate analogs using the novel phosphoramidite building blocks described herein has been demonstrated. Said phosphoramidite building blocks can be readily synthesized by artisans possessing ordinary skills. Conveniently, phosphotriester oligonucleotide analogs synthesized using said phosphoramidite building blocks are stable under the basic deprotection conditions as opposed to methyl triester analogs (U.S. Pat. No. 5,955,599), O-acyloxyaryl triester analogs (Iyer, R. P.; et al. Bioorg. Med. Chem. Lett. 1997, 7 (7), 871-876), acylaminoethyl analogs (U.S. Pat. Nos. 6,121,437, 6,610,837, US 2001/0044529, WO 2003/048179, and WO 2006/065751), (pivaloylthio)ethyl triester and similar analogs (U.S. Pat. No. 6,919,437, WO2010/039543 and in WO2014/031575).

EXAMPLES

The following examples are intended to further illustrate certain preferred embodiments of the invention and are not intended to be limiting in their nature.

General Information

Protected 2'-deoxynucleoside 2-cyanoethyl phosphoramidites, protected ribonucleoside 2-cyanoethyl phosphoramidites, and all ancillary reagents for oligonucleotide synthesis were purchased from Glen Research (Sterling, Va.). Sulfurizing reagent, N'-(3-thioxo-3H-1,2,4-dithiazol-5-yl)-N,N-dimethylmethanimidamide was prepared as disclosed in U.S. Pat. No. 7,723,582. Anhydrous MeCN was purchased from Honeywell Burdick & Jackson (Muskegon, Mich.). Protected 2'-deoxynucleosides, 2'-O-methylribonucleosides, and 2'-fluoro-2'-deoxyribonucleosides were purchased from Rasayan, Inc. (Encinitas, Calif.). Tri-tetra- and pentaethyleneglycols were purchased from Sigma-Aldrich (Milwaukee, Wis.). All other chemicals were purchased from TCI America (Portland, Oreg.).

Example 1

5'-O-(4,4'-Dimethoxytrityl)-3'-O—[(N,N-diisopropylamino)[3-[(2,3,4,6-tetra-O-acetyl-β-D-glucopyranosyl)oxy]propyl]phosphino]thymidine (12)

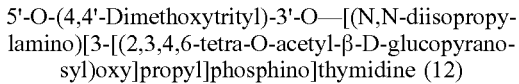

Solution of bis(N,N-diisopropylamino) chlorophosphite (2.94 g, 11 mmol) in anhydrous dichloromethane (10 mL) was added dropwise to a stirred solution of 5'-O-(4,4'-dimethoxytrityl)thymidine, 1, (5.88 g, 10.8 mmol) and N-ethyl-N,N-diisopropylamine (1.44 g, 11.1 mmol) in anhydrous dichloromethane (25 mL) at −20° C. The solution was allowed to stir at room temperature for 2 h. To the obtained mixture, 3-hydroxypropyl 2,3,4,6-tetra-O-acetyl-β-D-glucopyranoside (4.47 g, 11 mmol, prepared as disclosed in Karjala, S. and Link, K. P., J. Amer. Chem. Soc., 1940, 62, 917-922) and 1H-tetrazole (0.45 M in MeCN, 7.8 mL) were added followed by stirring at room temperature for 14 h. The reaction mixture was quenched by addition of excess 5% aqueous NaHCO$_3$. The emulsion was diluted with 5% aqueous NaHCO$_3$ (200 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient of ethyl acetate (from 20 to 80%) plus triethylamine (5%) in hexane. Collected fractions were evaporated to give the title compound as a mixture of S$_p$ and R$_p$ diastereomers (8.11 g, 69.5%). $^{31}$P NMR (CD$_3$CN): δ 147.94, 147.74. $^1$H NMR (CD$_3$CN): δ 8.941 (1H, br. s); 7.467-7.431 (3H, m); 7.331-7.291 (6H, m); 7.28-7.20 (1H, m); 6.886-6.855 (4H, m) 6.250-6.211 (1H, m); 5.247-5.171 (1H, m); 5.016-4.977 (1H, m); 4.866-4.822 (1H, m); 4.600-4.526 (1H, m); 4.203-4.168 (1H, m); 4.054-4.038 (2H, m); 3.90-3.83 (0.5H, m); 3.83-3.70 (2.5H, m); 3.765 (3H, s); 3.761 (3H, s); 3.68-3.45 (5H, m); 3.329-3.273 (2H, m); 2.45-2.38 (0.5H, m); 2.37-2.28 (1.5H, m); 2.015-1.929 (12H, m); 1.82-1.74 (1H, m); 1.72-1.64 (1H, m); 1.498 (1.5H, d, J=1.0 Hz); 1.476 (1.5H, d, J=1.0 Hz); 1.155-1.117 (9H, m); 1.033 (3H, d, J=6.8 Hz).

Example 2

N$^4$-Acetyl-5'-O-(4,4'-dimethoxytrityl)-3'-O—[(N,N-diisopropylamino)[3-[(2,3,4,6-tetra-O-acetyl-β-D-glucopyranosyl)oxy]propyl]phosphino]-2'-deoxycytidine (13a)

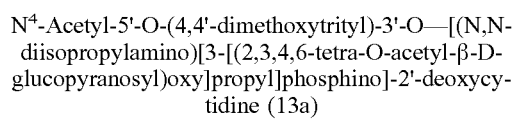

Solution of bis(N,N-diisopropylamino) chlorophosphite (5.27 g, 19.75 mmol) in anhydrous dichloromethane (20 mL) was added dropwise to a stirred solution of N$^4$-benzoyl-5'-O-(4,4'-dimethoxytrityl)-2'-deoxycytidine, 9a, (10.01 g, 15.8 mmol, Rasayan, Inc., Encinitas, Calif.) and N-ethyl-N,N-diisopropylamine (3.83 g, 29.6 mmol) in anhydrous dichloromethane (30 mL) at −20° C. The solution was allowed to stir at room temperature for 2 h. To the obtained mixture, 3-hydroxypropyl 2,3,4,6-tetra-O-acetyl-β-D-glucopyranoside, 1, (7.06 g, 17.38 mmol) and 1H-tetrazole (0.45 M in MeCN, 10.0 mL, 4.5 mmol) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (10:3:87) to ethyl acetate—TEA (94:6). Collected fractions were evaporated to give the title compound (13.30 g, 72.0%). $^{31}$P NMR (mixture of diastereomers, CD$_3$CN): δ 147.86, 147.53.

Example 3

N$^4$-Phenoxyacetyl-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxycytidine (13b)

Solution of bis(N,N-diisopropylamino) chlorophosphite (4.75 g, 17.81 mmol) in anhydrous dichloromethane (20 mL) was added dropwise to a stirred solution of N$^4$-phenoxyacetyl-5'-O-(4,4'-dimethoxytrityl)-2'-deoxycytidine, 9b, (9.46 g, 14.25 mmol, Rasayan, Inc., Encinitas, Calif.) and N-ethyl-N,N-diisopropylamine (3.45 g, 26.7 mmol) in anhydrous dichloromethane (30 mL) at −20° C. The solution was allowed to stir at room temperature for 2 h. To the obtained mixture, 3-hydroxypropyl 2,3,4,6-tetra-O-acetyl-β-D-glucopyranoside, 1, (6.37 g, 15.68 mmol) and 1H-tetrazole (0.45 M in MeCN, 12.7 mL) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (10:2:87) to TEA—ethyl acetate (10:90). Collected fractions were evaporated to give the title compound (11.60 g, 67.9%). $^{31}$P NMR (mixture of diastereomers, CD$_3$CN): δ 148.12, 147.77.

Example 4

N$^4$-Acetyl-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxycytidine (13c)

Solution of bis(N,N-diisopropylamino) chlorophosphite (4.62 g, 17.32 mmol) in anhydrous dichloromethane (15 mL) was added dropwise to a stirred solution of N$^4$-acetyl-5'-O-(4,4'-dimethoxytrityl)-2'-deoxycytidine, 9c, (7.83 g, 13.69 mmol, Rasayan, Inc., Encinitas, Calif.) and N-ethyl-N,N-diisopropylamine (2.12 g, 16.42 mmol) in anhydrous dichloromethane (30 mL) at −20° C. The solution was allowed to stir at room temperature for 2 h. To the obtained mixture, 3-hydroxypropyl 2,3,4,6-tetra-O-acetyl-β-D-glucopyranoside, 1, (6.40 g, 15.75 mmol) and 1H-tetrazole (0.45 M in MeCN, 10.0 mL, 4.5 mmol) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (10:2:87) to TEA—ethyl acetate (6:94). Collected fractions were evaporated to give the title compound (6.78 g, 44.7%). $^{31}$P NMR (mixture of diastereomers, CD$_3$CN): δ 147.97, 147.63. $^1$H NMR (fast diastereomer, CD$_3$CN): δ 8.805 (1H, br. s); 8.172 (1H, d, J=7.5 Hz); 7.429-7.412 (2H, m); 7.322-7.280 (6H, m); 7.257-7.228 (1H, m); 7.040 (1H, d, J=7.5 Hz); 6.878-6.848 (4H, m); 6.087 (1H, dd, J=6.5 Hz, 4.8 Hz); 5.323 (1H, t, J=9.6 Hz); 4.997 (1H, t, J=9.8 Hz); 4.838 (1H, dd, J=9.8, 8.0 Hz); 4.627 (1H, d, J=8.1 Hz); 4.50-4.48 (1H, m); 4.230 (1H, dd, J=12.3, 5.0 Hz); 4.103 (1H, m); 4.042 (1H, dd, J=12.3, 2.4 Hz); 3.885-3.849 (2H, m); 3.768 (6H, s); 3.625-3.510 (5H, m); 3.41-3.32 (2H, m); 2.573 (1H, d, J=13.7 Hz, t, J=6.7 Hz); 2.261 (1H, d, J=13.7 Hz, d, J=6.5 Hz, d, J=4.8 Hz); 2.116 (3H, s); 2.018 (3H, s); 1.975 (3H, s); 1.956-1.784 (6H, m); 1.772 (2H, tt, J=6.2 Hz); 1.123 (3H, d, J=6.8 Hz); 1.046 (3H, d, J=6.8 Hz).

Example 5

N$^6$-Benzoyl-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxyadenosine (14a)

Solution of bis(N,N-diisopropylamino) chlorophosphite (4.12 g, 15.44 mmol) in anhydrous dichloromethane (15 mL) was added dropwise to a stirred solution of N$^6$-benzoyl-5'-O-(4,4'-dimethoxytrityl)-2'-deoxyadenosine, 10a, (8.12 g, 12.35 mmol, Rasayan, Inc., Encinitas, Calif.) and N-ethyl-N,N-diisopropylamine (1.99 g, 15.44 mmol) in anhydrous dichloromethane (30 mL) at −20° C. The solution was allowed to stir at room temperature for 2 h. To the obtained mixture, 3-hydroxypropyl 2,3,4,6-tetra-O-acetyl-β-D-glucopyranoside, 1, (6.07 g, 14.94 mmol) and 1H-tetrazole (0.45 M in MeCN, 8.2 mL) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (10:2:87) to TEA—ethyl acetate (5:95). Collected fractions were evaporated to give the title compound (11.49 g, 78.0%). $^{31}$P NMR (mixture of diastereomers, CD$_3$CN): δ 147.87, 147.58. $^1$H NMR (mixture of diastereomers, CD$_3$CN): δ 9.318 (1H, br. s); 8.591 (1H, br. d, J=3.3 Hz); 8.263 (1H, s); 8.997 (1H, br d, J=7.2 Hz); 7.646 (1H, t, J=7.3 Hz); 7.551 (2H, t, J=7.7 Hz); 7.39-7.34 (2H, m); 7.25-7.16 (7H, m); 6.80-6.74 (4H, m); 6.48-6.42 (1H, m); 5.24-5.16 (1H, m); 5.05-4.96 (1H, m); 4.90-4.78 (2H, m); 4.556 (1H, dd, J=8.0, 5.1 Hz); 4.26-4.17 (2H, m); 4.08-3.98 (1.5H, m); 3.91-3.78 (1.5H, m); 3.740, 3.736, 3.733, 3.728 (total 6H, singlets); 3.78-3.69 (1H, m); 3.64-3.50 (5H, m); 3.48-3.24 (2H, m); 3.060 (1H, sept, J=6.4 Hz); 2.68-2.52 (1H, m); 2.00-1.90

(12H, m); 1.795 (1H, pent., J=6.1 Hz); 1.711 (1H, pent., J=6.1 Hz); 1.20-1.12 (9H, m); 1.080 (3H, d, J=6.8 Hz).

Example 6

N$^6$-Phenoxyacetyl-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxyadenosine (14b)

Solution of bis(N,N-diisopropylamino) chlorophosphite (3.50 g, 13.13 mmol) in anhydrous dichloromethane (15 mL) was added dropwise to a stirred solution of N$^6$-phenoxyacetyl-5'-O-(4,4'-dimethoxytrityl)-2'-deoxyadenosine, 10b, (7.22 g, 10.50 mmol, Rasayan, Inc., Encinitas, Calif.) and N-ethyl-N,N-diisopropylamine (2.55 g, 19.74 mmol) in anhydrous dichloromethane (30 mL) at −20° C. The solution was allowed to stir at room temperature for 2 h. To the obtained mixture, 3-hydroxypropyl 2,3,4,6-tetra-O-acetyl-β-D-glucopyranoside, 1, (4.69 g, 11.55 mmol) and 1H-tetrazole (0.45 M in MeCN, 9.3 mL) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (10:2:87) to TEA—ethyl acetate (10:90). Collected fractions were evaporated to give the title compound (9.05 g, 70.5%). $^{31}$P NMR (mixture of diastereomers, CD$_3$CN): δ 148.54, 148.01.

Example 7

N$^6$-(4-i-Propylphenoxy)acetyl-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxyadenosine (14c)

Solution of bis(N,N-diisopropylamino) chlorophosphite (3.94 g, 14.75 mmol) in anhydrous dichloromethane (15 mL) was added dropwise to a stirred solution of N$^6$-(4-i-propylphenoxy) acetyl-5'-O-(4,4'-dimethoxytrityl)-2'-deoxyadenosine, 10c, (8.61 g, 11.80 mmol, Rasayan, Inc., Encinitas, Calif.) and N-ethyl-N,N-diisopropylamine (2.87 g, 22.18 mmol) in anhydrous dichloromethane (30 mL) at −20° C. The solution was allowed to stir at room temperature for 2 h. To the obtained mixture, 3-hydroxypropyl 2,3,4,6-tetra-O-acetyl-β-D-glucopyranoside, 1, (5.27 g, 12.98 mmol) and 1H-tetrazole (0.45 M in MeCN, 10.5 mL) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (10:2:87) to TEA—ethyl acetate (10:90). Collected fractions were evaporated to give the title compound (10.44 g, 69.9%). $^{31}$P NMR (mixture of diastereomers, CD$_3$CN): δ 148.22, 147.72.

Example 8

N$^6$—(N,N-Dimethylformamidino)-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxyadenosine (14d)

Solution of bis(N,N-diisopropylamino) chlorophosphite (4.67 g, 17.5 mmol) in anhydrous dichloromethane (15 mL) was added dropwise to a stirred solution of N$^6$—(N,N-dimethylformamidino)-5'-O-(4,4'-dimethoxytrityl)-2'-deoxyadenosine, 10d, (8.52 g, 14.0 mmol, Rasayan, Inc., Encinitas, Calif.) and N-ethyl-N,N-diisopropylamine (3.40 g, 26.32 mmol) in anhydrous dichloromethane (30 mL) at −20° C. The solution was allowed to stir at room temperature for 2 h. To the obtained mixture, 3-hydroxypropyl 2,3,4,6-tetra-O-acetyl-β-D-glucopyranoside, 1, (6.25 g, 15.4 mmol) and 1H-tetrazole (0.45 M in MeCN, 12.44 mL) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (10:2:87) to TEA—ethyl acetate (10:90). Collected fractions were evaporated to give the title compound (12.56 g, 78.4%). $^{31}$P NMR (mixture of diastereomers, CD$_3$CN): δ 148.65, 148.12.

Example 9

N$^2$-Isobutyryl-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxyguanosine (15a)

Solution of bis(N,N-diisopropylamino) chlorophosphite (4.27 g, 16.0 mmol) in anhydrous dichloromethane (15 mL) was added dropwise to a stirred solution of N$^2$-isobutyryl-5'-O-(4,4'-dimethoxytrityl)-2'-deoxyguanosine, 11a, (8.53 g, 13.33 mmol, Rasayan, Inc., Encinitas, Calif.) and N-ethyl-N,N-diisopropylamine (2.15 g, 16.66 mmol) in anhydrous dichloromethane (30 mL) at −20° C. The solution was allowed to stir at room temperature for 2 h. To the obtained mixture, 3-hydroxypropyl 2,3,4,6-tetra-O-acetyl-β-D-glucopyranoside, 1, (6.50 g, 16.0 mmol) and 1H-tetrazole (0.45 M in MeCN, 10.0 mL, 4.5 mmol) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (20:5:75) to TEA—ethyl acetate (5:95). Collected fractions were evaporated to give the title compound as an off-white foam (8.54 g, 54.5%). $^{31}$P NMR (mixture of diastereomers, CD$_3$CN): δ 147.96, 147.62. $^1$H NMR (mixture of diastereomers, CD$_3$CN): δ 7.817, 7.812 (total 1H, s, s); 7.43-7.36 (2H, m); 7.29-7.18 (7H, m); 6.83-6.72 (4H, m); 6.249-6.214 (1H, m); 5.24-5.14 (1H, m); 5.03-4.94 (1H, m); 4.89-4.81

(1H, m); 4.64-4.52 (2H, m); 4.22-4.12 (2H, m); 4.07-3.98 (1H, m); 3.90-3.88 (1H, m); 3.748, 3.744, 3.740 (total 6H, s, s, s); 3.77-3.69 (1H, m); 3.68-3.49 (5H, m); 3.37-3.28 (1H, m); 3.27-3.19 (1H, m); 2.94-2.83 (1H, m); 2.601 (1H, sept., J=6.8 Hz); 2.58-2.43 (1H, m); 1.99-1.93 (12H, m); 1.777 (1.5H, pent., J=6.2 Hz); 1.698 (0.5H, m); 1.186-1.131 (12H, m); 1.063 (3H, d, J=6.8 Hz).

Example 10

$N^2$-Phenoxyacetyl-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxyguanosine (15b)

Solution of bis(N,N-diisopropylamino) chlorophosphite (2.83 g, 10.6 mmol) in anhydrous dichloromethane (10 mL) was added dropwise to a stirred solution of $N^2$-phenoxyacetyl-5'-O-(4,4'-dimethoxytrityl)-2'-deoxyguanosine, 11b, (5.98 g, 8.5 mmol, Rasayan, Inc., Encinitas, Calif.) and N-ethyl-N,N-diisopropylamine (2.06 g, 16.0 mmol) in anhydrous dichloromethane (25 mL) at −20° C. The solution was allowed to stir at room temperature for 2 h. To the obtained mixture, 3-hydroxypropyl 2,3,4,6-tetra-O-acetyl-β-D-glucopyranoside, 1, (3.97 g, 9.78 mmol) and 1H-tetrazole (0.45 M in MeCN, 7.6 mL) were added followed by stirring at room temperature for 14 h. The reaction mixture was quenched by addition of excess 5% aqueous $NaHCO_3$. The emulsion was diluted with 5% aqueous $NaHCO_3$ (100 mL), and the product was extracted with ethyl acetate (3×100 mL). Extracts were washed with brine, dried over anhydrous $Na_2SO_4$, and evaporated to oil. The product was isolated chromatographically on a silica gel column eluted with a step gradient from ethyl acetate—TEA—hexane (20:5:75) to TEA—ethyl acetate (10:90). Collected fractions were evaporated to give the title compound as an off-white foam (6.54 g, 62.1%). $^{31}P$ NMR (mixture of diastereomers, $CD_3CN$): δ 148.90, 148.48.

Example 11

$N^2$-(4-i-Propylphenoxy)acetyl-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxyguanosine (15c)

Solution of bis(N,N-diisopropylamino) chlorophosphite (3.33 g, 12.5 mmol) in anhydrous dichloromethane (10 mL) was added dropwise to a stirred solution of $N^2$-(4-i-propylphenoxy)acetyl-5'-O-(4,4'-dimethoxytrityl)-2'-deoxyguanosine, 11c, (7.46 g, 10.0 mmol, Rasayan, Inc., Encinitas, Calif.) and N-ethyl-N,N-diisopropylamine (2.43 g, 18.8 mmol) in anhydrous dichloromethane (25 mL) at −20° C. The solution was allowed to stir at room temperature for 2 h. To the obtained mixture, 3-hydroxypropyl 2,3,4,6-tetra-O-acetyl-β-D-glucopyranoside, 1, (4.67 g, 11.5 mmol) and 1H-tetrazole (0.45 M in MeCN, 8.9 mL) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×100 mL). Extracts were washed with brine, dried over anhydrous $Na_2SO_4$, and evaporated to oil. The product was isolated chromatographically on a silica gel column eluted with a step gradient from ethyl acetate—TEA—hexane (20:5:75) to TEA—ethyl acetate (10:90). Collected fractions were evaporated to give the title compound as an off-white foam (8.10 g, 63.3%). $^{31}P$ NMR (mixture of diastereomers, $CD_3CN$): δ 148.88, 148.32.

Example 12

$N^2$—(N,N-Dimethylformamidino)-5'-O-(4,4'-dimethoxytrityl)-3'-O—[(N,N-diisopropylamino)[3-[(2,3,4,6-tetra-O-acetyl-β-D-glucopyranosyl)oxy]propoxy]phosphinyl]-2'-deoxyguanosine (15d)

Solution of bis(N,N-diisopropylamino) chlorophosphite (3.67 g, 13.75 mmol) in anhydrous dichloromethane (10 mL) was added dropwise to a stirred solution of $N^2$—(N,N-dimethylformamidino)-5'-O-(4,4'-dimethoxytrityl)-2'-deoxyguanosine, 11d, (6.87 g, 11.0 mmol, Rasayan, Inc., Encinitas, Calif.) and N-ethyl-N,N-diisopropylamine (2.67 g, 20.7 mmol) in anhydrous dichloromethane (25 mL) at −20° C. The solution was allowed to stir at room temperature for 2 h. To the obtained mixture, 3-hydroxypropyl 2,3,4,6-tetra-O-acetyl-β-D-glucopyranoside, 1, (2.92 g, 6.7 mmol) and 1H-tetrazole (0.45 M in MeCN, 9.8 mL) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×100 mL). Extracts were washed with brine, dried over anhydrous $Na_2SO_4$, and evaporated to oil. The product was isolated chromatographically on a silica gel column eluted with a step gradient from ethyl acetate—TEA—hexane (20:5:75) to TEA—ethyl acetate (10:90). Collected fractions were evaporated to give the title compound as an off-white foam (8.10 g, 63.3%). $^{31}P$ NMR (mixture of diastereomers, $CD_3CN$): δ 148.88, 148.32.

Example 13

5'-O-(4,4'-Dimethoxytrityl)-3'-O—[(N,N-diisopropylamino)[2-[[2-[(2,3,4,6-tetra-O-acetyl-β-D-glucopyranosyl)oxy]ethyl]oxy]ethoxy]phosphinyl]thymidine (16)

Solution of bis(N,N-diisopropylamino) chlorophosphite (1.86 g, 6.98 mmol) in anhydrous dichloromethane (5 mL) was added dropwise to a stirred solution of 5'-O-(4,4'-dimethoxytrityl)thymidine, 8, (3.17 g, 5.82 mmol) and N-ethyl-N,N-diisopropylamine (0.99 g, 7.68 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (2.92 g, 6.69 mmol, prepared as disclosed in Karjala, S. and Link, K. P., *J. Amer. Chem. Soc.*, 1940, 62, 917-922) and 1H-tetrazole (0.45 M in MeCN, 3.9 mL, 1.76 mmol) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×100 mL). Extracts were washed with brine, dried over anhydrous $Na_2SO_4$, and evaporated to oil. The product was isolated chromatographically on a silica gel column eluted with a step gradient from ethyl acetate—TEA—hexane (20:2:77) to TEA—ethyl acetate (6:94). Collected fractions were evaporated to give the title compound (4.87 g, 75.4%). $^{31}P$ NMR (mixture of diastereomers, $CD_3CN$): δ 148.23, 148.12. $^1H$ NMR (mixture of diastereomers, $CD_3CN$): δ 8.910 (1H, br. s); 7.48-7.40 (3H, m); 7.37-7.28 (6H, m); 7.28-7.20 (1H, m); 6.90-6.82 (4H, m); 6.28-6.20 (1H, m);

5.26-5.18 (1H, m); 5.05-4.97 (1H, m); 4.89-4.82 (1H, m); 4.68-4.53 (2H, m); 4.26-4.18 (1H, m); 4.12-4.01 (2H, m); 3.87-3.68 (8H, m, s, s); 3.68-3.41 (9H, m); 3.38-3.23 (2H, m); 2.45-2.29 (2H, m); 2.02-1.92 (12H, m); 1.495 (1.5H, d, J=1.2 Hz); 1.471 (1.5H, d, J=1.2 Hz); 1.17-1.11 (9H, m); 1.040 (3H, d, J=6.8 Hz).

Example 14

$N^4$-Benzoyl-5'-O-(4,4'-dimethoxytrityl)-3'-O—[(N,N-diisopropylamino)[2-[[2-[(2,3,4,6-tetra-O-acetyl-β-D-glucopyranosyl)oxy]ethyl]oxy]ethoxy]phosphinyl]-2'-deoxycytidine (17a)

Solution of bis(N,N-diisopropylamino) chlorophosphite (2.00 g, 7.5 mmol) in anhydrous dichloromethane (5 mL) was added dropwise to a stirred solution of $N^4$-benzoyl-5'-O-(4,4'-dimethoxytrityl)-2'-deoxycytidine, 9a, (3.80 g, 6.0 mmol) and N-ethyl-N,N-diisopropylamine (1.47 g, 11.4 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (3.01 g, 6.9 mmol) and 1H-tetrazole (0.45 M in MeCN, 5.3 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (20:2:77) to TEA—ethyl acetate (5:95). Collected fractions were evaporated to give the title compound (5.14 g, 71.4%). $^{31}$P NMR (mixture of diastereomers, CD$_3$CN): δ 148.76, 148.39.

Example 15

$N^4$-Phenoxyacetyl-5'-O-(4,4'-dimethoxytrityl)-3'-O—[(N,N-diisopropylamino)[2-[[2-[(2,3,4,6-tetra-O-acetyl-β-D-glucopyranosyl)oxy]ethyl]oxy]ethoxy]phosphinyl]-2'-deoxycytidine (17b)

Solution of bis(N,N-diisopropylamino) chlorophosphite (2.00 g, 7.5 mmol) in anhydrous dichloromethane (5 mL) was added dropwise to a stirred solution of $N^4$-phenoxyacetyl-5'-O-(4,4'-dimethoxytrityl)-2'-deoxycytidine, 9b, (3.98 g, 6.0 mmol) and N-ethyl-N,N-diisopropylamine (1.47 g, 11.4 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (3.01 g, 6.9 mmol) and 1H-tetrazole (0.45 M in MeCN, 5.3 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (20:2:77) to TEA—ethyl acetate (5:95). Collected fractions were evaporated to give the title compound (4.86 g, 65.9%). $^{31}$P NMR (mixture of diastereomers, CD$_3$CN): δ 148.05, 147.66.

Example 16

$N^4$-Acetyl-5'-O-(4,4'-dimethoxytrityl)-3'-O—[(N,N-diisopropylamino)[2-[[2-[(2,3,4,6-tetra-O-acetyl-β-D-glucopyranosyl)oxy]ethyl]oxy]ethoxy]phosphinyl]-2'-deoxycytidine (17c)

Solution of bis(N,N-diisopropylamino) chlorophosphite (2.00 g, 7.5 mmol) in anhydrous dichloromethane (5 mL) was added dropwise to a stirred solution of $N^4$-acetyl-5'-O-(4,4'-dimethoxytrityl)-2'-deoxycytidine, 9c, (3.43 g, 6.0 mmol) and N-ethyl-N,N-diisopropylamine (1.47 g, 11.4 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (3.01 g, 6.9 mmol) and 1H-tetrazole (0.45 M in MeCN, 5.3 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (20:2:77) to TEA—ethyl acetate (5:95). Collected fractions were evaporated to give the title compound (5.00 g, 73.3%). $^{31}$P NMR (mixture of diastereomers, CD$_3$CN): δ 148.58, 148.14.

Example 17

$N^6$-Benzoyl-5'-O-(4,4'-dimethoxytrityl)-3'-O—[(N,N-diisopropylamino)[2-[[2-[(2,3,4,6-tetra-O-acetyl-β-D-glucopyranosyl)oxy]ethyl]oxy]ethoxy]phosphinyl]-2'-deoxyadenosine (18a)

Solution of bis(N,N-diisopropylamino) chlorophosphite (1.67 g, 6.25 mmol) in anhydrous dichloromethane (5 mL) was added dropwise to a stirred solution of $N^6$-benzoyl-5'-O-(4,4'-dimethoxytrityl)-2'-deoxyadenosine, 10a, (3.29 g, 5.0 mmol) and N-ethyl-N,N-diisopropylamine (1.23 g, 9.5 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (2.51 g, 5.75 mmol) and 1H-tetrazole (0.45 M in MeCN, 4.4 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (20:2:77) to TEA—ethyl acetate (5:95). Collected fractions were evaporated to give the title compound (4.33 g, 70.8%). $^{31}$P NMR (mixture of diastereomers, CD$_3$CN): δ 148.32, 147.78.

Example 18

$N^6$-Phenoxyacetyl-5'-O-(4,4'-dimethoxytrityl)-3'-O—[(N,N-diisopropylamino)[2-[[2-[(2,3,4,6-tetra-O-acetyl-β-D-glucopyranosyl)oxy]ethyl]oxy]ethoxy]phosphinyl]-2'-deoxyadenosine (18b)

Solution of bis(N,N-diisopropylamino) chlorophosphite (1.67 g, 6.25 mmol) in anhydrous dichloromethane (5 mL)

was added dropwise to a stirred solution of $N^6$-phenoxyacetyl-5'-O-(4,4'-dimethoxytrityl)-2'-deoxyadenosine, 10b, (3.44 g, 5.0 mmol) and N-ethyl-N,N-diisopropylamine (1.23 g, 9.5 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (2.51 g, 5.75 mmol) and 1H-tetrazole (0.45 M in MeCN, 4.4 mL) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×100 mL). Extracts were washed with brine, dried over anhydrous $Na_2SO_4$, and evaporated to oil. The product was isolated chromatographically on a silica gel column eluted with a step gradient from ethyl acetate—TEA—hexane (20:2:77) to TEA—ethyl acetate (5:95). Collected fractions were evaporated to give the title compound (3.98 g, 63.5%). $^{31}$P NMR (mixture of diastereomers, $CD_3CN$): δ 148.44, 147.63.

Example 19

$N^6$-(4-i-Propylphenoxy)acetyl-5'-O-(4,4'-dimethoxytrityl)-3'-O—[(N,N-diisopropylamino)[2-[[2-[(2,3,4,6-tetra-O-acetyl-β-D-glucopyranosyl)oxy]ethyl]oxy]ethoxy]phosphinyl]-2'-deoxyadenosine (18c)

Solution of bis(N,N-diisopropylamino) chlorophosphite (1.67 g, 6.25 mmol) in anhydrous dichloromethane (5 mL) was added dropwise to a stirred solution of $N^6$-(4-i-propylphenoxy) acetyl-5'-O-(4,4'-dimethoxytrityl)-2'-deoxyadenosine, 10c, (3.65 g, 5.0 mmol) and N-ethyl-N,N-diisopropylamine (1.23 g, 9.5 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (2.51 g, 5.75 mmol) and 1H-tetrazole (0.45 M in MeCN, 4.4 mL) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×100 mL). Extracts were washed with brine, dried over anhydrous $Na_2SO_4$, and evaporated to oil. The product was isolated chromatographically on a silica gel column eluted with a step gradient from ethyl acetate—TEA—hexane (20:2:77) to TEA—ethyl acetate (5:95). Collected fractions were evaporated to give the title compound (4.22 g, 65.1%). $^{31}$P NMR (mixture of diastereomers, $CD_3CN$): δ 148.20, 147.69.

Example 20

$N^6$—(N,N-Dimethylformamidino)-5'-O-(4,4'-dimethoxytrityl)-3'-O—[(N,N-diisopropylamino)[2-[[2-[(2,3,4,6-tetra-O-acetyl-β-D-glucopyranosyl)oxy]ethyl]oxy]ethoxy]phosphinyl]-2'-deoxyadenosine (18d)

Solution of bis(N,N-diisopropylamino) chlorophosphite (1.67 g, 6.25 mmol) in anhydrous dichloromethane (5 mL) was added dropwise to a stirred solution of $N^6$—(N,N-dimethylformamidino)-5'-O-(4,4'-dimethoxytrityl)-2'-deoxyadenosine, 10d, (3.04 g, 5.0 mmol) and N-ethyl-N,N-diisopropylamine (1.23 g, 9.5 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (2.51 g, 5.75 mmol) and 1H-tetrazole (0.45 M in MeCN, 4.4 mL) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×100 mL). Extracts were washed with brine, dried over anhydrous $Na_2SO_4$, and evaporated to oil. The product was isolated chromatographically on a silica gel column eluted with a step gradient from ethyl acetate—TEA—hexane (20:2:77) to TEA—ethyl acetate (5:95). Collected fractions were evaporated to give the title compound (4.56 g, 77.7%). $^{31}$P NMR (mixture of diastereomers, $CD_3CN$): δ 148.88, 148.27.

Example 21

$N^2$-Isobutyryl-5'-O-(4,4'-dimethoxytrityl)-3'-O—[(N,N-diisopropylamino) [2-[[2-[(2,3,4,6-tetra-O-acetyl-β-D-glucopyranosyl)oxy]ethyl]oxy]ethoxy]phosphinyl]-2'-deoxyguanosine (19a)

Solution of bis(N,N-diisopropylamino) chlorophosphite (2.23 g, 8.4 mmol) in anhydrous dichloromethane (15 mL) was added dropwise to a stirred solution of $N^2$-isobutyryl-5'-O-(4,4'-dimethoxytrityl)-2'-deoxyguanosine, 11a, (4.29 g, 6.7 mmol, Rasayan, Inc., Encinitas, Calif.) and N-ethyl-N,N-diisopropylamine (1.64 g, 12.7 mmol) in anhydrous dichloromethane (30 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (3.36 g, 7.7 mmol) and 1H-tetrazole (0.45 M in MeCN, 10.0 mL, 6.0 mmol) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×100 mL). Extracts were washed with brine, dried over anhydrous $Na_2SO_4$, and evaporated to oil. The product was isolated chromatographically on a silica gel column eluted with a step gradient from ethyl acetate—TEA—hexane (20:5:75) to TEA—ethyl acetate (5:95). Collected fractions were evaporated to give the title compound as an off-white foam (5.75 g, 71.2%). $^{31}$P NMR (mixture of diastereomers, $CD_3CN$): δ 148.91, 148.38.

Example 22

$N^2$-Phenoxyacetyl-5'-O-(4,4'-dimethoxytrityl)-3'-O—[(N,N-diisopropylamino) [2-[[2-[(2,3,4,6-tetra-O-acetyl-β-D-glucopyranosyl)oxy]ethyl]oxy]ethoxy]phosphinyl]-2'-deoxyguanosine (19b)

Solution of bis(N,N-diisopropylamino) chlorophosphite (1.80 g, 6.75 mmol) in anhydrous dichloromethane (10 mL) was added dropwise to a stirred solution of $N^2$-phenoxyacetyl-5'-O-(4,4'-dimethoxytrityl)-2'-deoxyguanosine, 11b, (3.80 g, 5.4 mmol, Rasayan, Inc., Encinitas, Calif.) and N-ethyl-N,N-diisopropylamine (1.33 g, 10.3 mmol) in anhydrous dichloromethane (20 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (2.71 g, 6.2 mmol) and 1H-tetrazole (0.45 M in MeCN, 4.8 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (20:5:75) to TEA—ethyl acetate (5:95). Collected fractions were evaporated to give the title compound as an off-white foam (4.58 g, 66.8%). $^{31}$P NMR (mixture of diastereomers, CD$_3$CN): δ 149.04, 148.60.

Example 23

N$^2$-(4-i-Propylphenoxy)acetyl-5'-O-(4,4'-dimethoxytrityl)-3'-O—[(N,N-diisopropylamino) [2-[[2-[(2,3,4,6-tetra-O-acetyl-β-D-glucopyranosyl)oxy]ethyl]oxy]ethoxy]phosphinyl]-2'-deoxyguanosine (19c)

Solution of bis(N,N-diisopropylamino) chlorophosphite (1.97 g, 7.38 mmol) in anhydrous dichloromethane (10 mL) was added dropwise to a stirred solution of N$^2$-(4-i-propylphenoxy) acetyl-5'-O-(4,4'-dimethoxytrityl)-2'-deoxyguanosine, 11c, (4.40 g, 5.9 mmol, Rasayan, Inc., Encinitas, Calif.) and N-ethyl-N,N-diisopropylamine (1.45 g, 11.2 mmol) in anhydrous dichloromethane (20 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (2.96 g, 6.8 mmol) and 1H-tetrazole (0.45 M in MeCN, 5.3 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (20:5:75) to TEA—ethyl acetate (5:95). Collected fractions were evaporated to give the title compound as an off-white foam (4.84 g, 62.6%). $^{31}$P NMR (mixture of diastereomers, CD$_3$CN): δ 148.75, 148.19.

Example 24

N$^2$—(N,N-dimethylformamidino)-5'-O-(4,4'-dimethoxytrityl)-3'-O—[(N,N-diisopropylamino) [2-[[2-[(2,3,4,6-tetra-O-acetyl-13-D-glucopyranosyl)oxy]ethyl]oxy]ethoxy]phosphinyl]-2'-deoxyguanosine (19d)

Solution of bis(N,N-diisopropylamino) chlorophosphite (1.73 g, 6.50 mmol) in anhydrous dichloromethane (10 mL) was added dropwise to a stirred solution of N$^2$—(N,N-dimethylformamidino)-5'-O-(4,4'-dimethoxytrityl)-2'-deoxyguanosine, 11d, (3.25 g, 5.20 mmol, Rasayan, Inc., Encinitas, Calif.) and N-ethyl-N,N-diisopropylamine (1.28 g, 9.88 mmol) in anhydrous dichloromethane (20 mL) at −20° C. The solution was allowed to stir at room temperature for 2 h. To the obtained mixture, 2-[(2-hydroxyethyl)oxy]ethyl 2,3,4,6-tetra-O-acetyl-β-D-glucopyranoside, 2, (2.61 g, 5.98 mmol) and 1H-tetrazole (0.45 M in MeCN, 4.6 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column eluted with a step gradient from ethyl acetate—TEA—hexane (20:5:75) to TEA—ethyl acetate (5:95). Collected fractions were evaporated to give the title compound as an off-white foam (4.34 g, 70.1%). $^{31}$P NMR (mixture of diastereomers, CD$_3$CN): δ 148.63, 148.08.

Example 25

5'-O-(4,4'-Dimethoxytrityl)-3'-O—[(N,N-diisopropylamino)[2-[[2-[(2,3,4,6-tetra-O-acetyl-β-D-galactopyranosyl)oxy]ethyl]oxy]ethoxy]phosphinyl]thymidine (20)

Solution of bis(N,N-diisopropylamino) chlorophosphite (1.28 g, 4.79 mmol) in anhydrous dichloromethane (5 mL) was added dropwise to a stirred solution of 5'-O-(4,4'-dimethoxytrityl)thymidine, 8, (2.08 g, 3.83 mmol) and N-ethyl-N,N-diisopropylamine (0.94 g, 7.28 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-galactopyranoside, 3, (1.92 g, 4.40 mmol, prepared as disclosed in Karjala, S. and Link, K. P., J. Amer. Chem. Soc., 1940, 62, 917-922) and 1H-tetrazole (0.45 M in MeCN, 3.4 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column as described above for the respective β-D-glucopyranoside analog 16 to give the title compound (3.60 g, 84.8%). $^{31}$P NMR (mixture of diastereomers, CD$_3$CN): δ 148.66, 148.09.

Example 26

N$^4$-Benzoyl-5'-O-(4,4'-dimethoxytrityl)-3'-O—[(N,N-diisopropylamino)[2-[[2-[(2,3,4,6-tetra-O-acetyl-β-D-galactopyranosyl)oxy]ethyl]oxy]ethoxy]phosphinyl]-2'-deoxycytidine (21a)

Solution of bis(N,N-diisopropylamino) chlorophosphite (1.28 g, 4.79 mmol) in anhydrous dichloromethane (5 mL) was added dropwise to a stirred solution of N$^4$-benzoyl-5'-O-(4,4'-dimethoxytrityl)-2'-deoxycytidine, 9a, (2.08 g, 3.73 mmol) and N-ethyl-N,N-diisopropylamine (1.01 g, 7.83 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-galactopyranoside, 3, (2.07 g, 4.74 mmol) and 1H-tetrazole (0.45 M in MeCN, 3.7 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column as described above for the respective β-D-glucopyranoside analog 17a give the title compound (3.97 g, 80.3%). $^{31}$P NMR (mixture of diastereomers, CD$_3$CN): δ 148.69, 148.33.

Example 27

N$^4$-Acetyl-5'-O-(4,4'-dimethoxytrityl)-3'-O—[(N,N-diisopropylamino)[2-[[2-[(2,3,4,6-tetra-O-acetyl-β-D-galactopyranosyl)oxy]ethyl]oxy]ethoxy]phosphinyl]-2'-deoxycytidine (21c)

Solution of bis(N,N-diisopropylamino) chlorophosphite (1.48 g, 5.35 mmol) in anhydrous dichloromethane (5 mL) was added dropwise to a stirred solution of N$^4$-acetyl-5'-O-(4,4'-dimethoxytrityl)-2'-deoxycytidine, 9c, (2.45 g, 4.28 mmol) and N-ethyl-N,N-diisopropylamine (1.05 g, 8.13 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-galactopyranoside, 3, (2.15 g, 4.92 mmol) and 1H-tetrazole (0.45 M in MeCN, 3.8 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column as described above for the respective β-D-glucopyranoside analog 17c to give the title compound (4.05 g, 83.1%). $^{31}$P NMR (mixture of diastereomers, CD$_3$CN): δ 149.16, 148.66.

Example 28

N$^6$-Benzoyl-5'-O-(4,4'-dimethoxytrityl)-3'-O—[(N,N-diisopropylamino)[2-[[2-[(2,3,4,6-tetra-O-acetyl-β-D-galactopyranosyl)oxy]ethyl]oxy]ethoxy]phosphinyl]-2'-deoxyadenosine (22a)

Solution of bis(N,N-diisopropylamino) chlorophosphite (1.32 g, 4.94 mmol) in anhydrous dichloromethane (5 mL) was added dropwise to a stirred solution of N$^6$-benzoyl-5'-O-(4,4'-dimethoxytrityl)-2'-deoxyadenosine, 10a, (2.60 g, 3.95 mmol) and N-ethyl-N,N-diisopropylamine (0.97 g, 7.51 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-galactopyranoside, 3, (1.98 g, 4.54 mmol) and 1H-tetrazole (0.45 M in MeCN, 3.5 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column as described above for the respective β-D-glucopyranoside analog 18a give the title compound (3.65 g, 75.5%). $^{31}$P NMR (mixture of diastereomers, CD$_3$CN): δ 148.73, 148.18.

Example 29

N$^6$-Phenoxyacetyl-5'-O-(4,4'-dimethoxytrityl)-3'-O—[(N,N-diisopropylamino)[2-[[2-[(2,3,4,6-tetra-O-acetyl-β-D-galactopyranosyl)oxy]ethyl]oxy]ethoxy]phosphinyl]-2'-deoxyadenosine (22b)

Solution of bis(N,N-diisopropylamino) chlorophosphite (1.25 g, 4.68 mmol) in anhydrous dichloromethane (5 mL) was added dropwise to a stirred solution of N$^6$-phenoxyacetyl-5'-O-(4,4'-dimethoxytrityl)-2'-deoxyadenosine, 10b, (2.57 g, 3.74 mmol) and N-ethyl-N,N-diisopropylamine (0.92 g, 7.1 mmol) in anhydrous dichloromethane (15 mL) at −20° C. The solution was allowed to stir at room temperature for 2 h. To the obtained mixture, 2-[(2-hydroxyethyl)oxy]ethyl 2,3,4,6-tetra-O-acetyl-β-D-galactopyranoside, 3, (1.88 g, 4.30 mmol) and 1H-tetrazole (0.45 M in MeCN, 3.4 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column as described above for the respective β-D-glucopyranoside analog 18b to give the title compound (3.30 g, 70.4%). $^{31}$P NMR (mixture of diastereomers, CD$_3$CN): δ 148.80, 148.17.

Example 30

N$^2$-Isobutyryl-5'-O-(4,4'-dimethoxytrityl)-3'-O—[(N,N-diisopropylamino) [2-[[2-[(2,3,4,6-tetra-O-acetyl-β-D-galactopyranosyl)oxy]ethyl]oxy]ethoxy]phosphinyl]-2'-deoxyguanosine (23a)

Solution of bis(N,N-diisopropylamino) chlorophosphite (1.33 g, 5.0 mmol) in anhydrous dichloromethane (15 mL) was added dropwise to a stirred solution of N$^2$-isobutyryl-5'-O-(4,4'-dimethoxytrityl)-2'-deoxyguanosine, 11a, (2.56 g, 4.0 mmol, Rasayan, Inc., Encinitas, Calif.) and N-ethyl-N,N-diisopropylamine (098 g, 7.60 mmol) in anhydrous dichloromethane (30 mL) at −20° C. The solution was allowed to stir at room temperature for 2 h. To the obtained mixture, 2-[(2-hydroxyethyl)oxy]ethyl 2,3,4,6-tetra-O-acetyl-β-D-galactopyranoside, 3, (2.01 g, 4.60 mmol) and 1H-tetrazole (0.45 M in MeCN, 3.6 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column as described above for the respective β-D-glucopyranoside analog 19a to give the title compound as an off-white foam (3.56 g, 73.9%). $^{31}$P NMR (mixture of diastereomers, CD$_3$CN): δ 149.32, 148.66.

Example 31

N$^2$-Phenoxyacetyl-5'-O-(4,4'-dimethoxytrityl)-3'-O—[(N,N-diisopropylamino) [2-[[2-[(2,3,4,6-tetra-O-acetyl-β-D-galactopyranosyl)oxy]ethyl]oxy]ethoxy]phosphinyl]-2'-deoxyguanosine (23b)

Solution of bis(N,N-diisopropylamino) chlorophosphite (1.22 g, 4.59 mmol) in anhydrous dichloromethane (10 mL) was added dropwise to a stirred solution of N$^2$-phenoxyacetyl-5'-O-(4,4'-dimethoxytrityl)-2'-deoxyguanosine, 11b, (2.58 g, 3.67 mmol, Rasayan, Inc., Encinitas, Calif.) and N-ethyl-N,N-diisopropylamine (0.90 g, 6.97 mmol) in anhydrous dichloromethane (20 mL) at −20° C. The solution was allowed to stir at room temperature for 2 h. To the obtained mixture, 2-[(2-hydroxyethyl)oxy]ethyl 2,3,4,6-tetra-O-acetyl-β-D-galactopyranoside, 3, (1.84 g, 4.22 mmol) and 1H-tetrazole (0.45 M in MeCN, 3.3 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated chromatographically on a silica gel column as described above for the respective β-D-glucopyranoside analog 19b to give the title compound as an off-white foam (3.23 g, 69.3%). $^{31}$P NMR (mixture of diastereomers, CD$_3$CN): δ 149.33, 148.69.

Example 32

1-O-(3-Hydroxypropyl)-3,4,6-tri-O-acetyl-2-acetylamino-2-deoxy-β-D-glucopyranoside (6)

A mixture of compound 4 (8.80 g, 26.7 mmol, prepared as disclosed in Fukase, K.; Ueno, A.; Fukase, Y; et al., *Bull. Chem. Soc. Japan* 2003, 76, 485-500), 1,3-propanediol (30.5 g, 0.4 mol), and pyridinium p-toluenesulfonate (5.37 g, 21.4 mmol) was heated at 80° C. for 18 h, then distributed between DCM (50 mL) and a 1:1 mixture of brine and 5% aqueous NaHCO$_3$ (100 mL). The organic phase was separated, dried over Na$_2$SO$_4$, and evaporated in vacuo. The product was isolated by column chromatography on silica gel eluted with a step gradient from DCM to a mixture of MeOH and DCM (8:92). The solid obtained by evaporation of the relevant fractions was re-crystallized from a mixture of methyl t-butyl ether and DCM to give 2.91 g of pure ?? as an off-white solid. Found: C, 49.69; H, 6.77; N, 3.57. C$_{17}$H$_{27}$N$_{10}$.½H$_2$O. Calculated: C, 49.27; H, 6.81; N, 3.38. $^1$H NMR (CD$_3$CN): δ 6.395 (1H, br. d, J=9.5 Hz); 5.134 (1H, dd, J=10.5, 9.5 Hz); 4.932 (1H, t, J=9.7 Hz); 4.612 (1H, d, J=8.5 Hz); 4.215 (1H, dd, J=12.5, 5.0 Hz); 4.074 (1H, dd, J=12.5, 2.5 Hz); 3.876-3.835 (1H, m); 3.802-3.759 (2H, m); 3.625-3.560 (1H, m); 3.560-3.523 (2H, m); 2.554 (1H, t, J=5.2 Hz); 2.015 (3H, s); 1.965 (3H, s); 1.935 (3H, s); 1.820 (3H, s); 1.707 (2H, pent., J=6.2 Hz). The mother liquor was evaporated, and the residue was re-crystallized from the same mixture to give additional product (2.61 g) in a total yield of 51.3%.

Example 33

5'-O-(4,4'-Dimethoxytrityl)-3'-O—[(N,N-diisopropylamino)[3-[(3,4,6-tri-O-acetyl-2-acetylamino-2-deoxy-β-D-glucopyranosyl)oxy]propoxy]phosphinyl] thymidine (24)

To the magnetically stirred mixture of 5'-O-(4,4'-dimethoxytrityl)thymidine, 8, (5.99 g, 11.0 mmol), N-ethyl-N,N-diisopropylamine (2.70 g, 20.90 mmol), and anhydrous CH$_3$CN (30 mL) was added a solution of N,N,N',N'-tetraisopropyl chlorophosphite (3.67 g, 13.75 mmol) in anhydrous DCM (10 mL) at −20° C. The mixture was allowed to warm up to room temperature over 2 h. A solution of 1-O-(3-hydroxypropyl)-3,4,6-tri-O-acetyl-2-acetylamino-2-deoxy-β-D-glucopyranoside, 6, (0.405 g, 1 mmol) in anhydrous acetonitrile (5 mL) was added followed by the addition of a solution of 1H-tetrazole in acetonitrile (0.45 M, 9.8 mL). The reaction mixture was stirred for 18 h at room temperature and was quenched by adding 5% aqueous NaHCO$_3$. The product was extracted with ethyl acetate (3×100 mL). Combined extracts were washed with brine (50 mL), dried over anhydrous Na$_2$SO$_4$, and evaporated to dryness. The product was isolated by column chromatography on silica gel eluted with a step gradient starting from TEA—ethyl acetate—hexane (5:20:75) to a mixture of TEA in ethyl acetate (10:90). Evaporation of fractions gave compound 24 as white solid foam in a yield of 10.37 g (87.4%). $^{31}$P NMR (CD$_3$CN): δ 147.60, 147.57. $^1$H NMR (CD$_3$CN): δ 8.955 (1H, br. s); 7.45-7.41 (3H, m); 7.35-7.28 (6H, m); 7.28-7.21 (1H, m); 6.90-6.84 (4H, m); 6.590 (0.5H, d, J=9.0 Hz); 6.342 (0.5H, d, J=4.5 Hz); 6.230 (0.5H, t, J=9.0 Hz); 6.195 (0.5H, t, J=7.0 Hz); 5.184 (0.5H, dd, J=10.5, 9.5 Hz); 5.135 (0.5H, dd, J=10.5, 9.5 Hz); 4.920 (1H, q, J=9.7 Hz); 4.630-4.525 (2H, m); 4.188 (1H, ddd, J=12.5, 12.5, 5.0 Hz); 4.13-4.09 (0.5H, m); 4.09-3.95 (2H, m); 3.89-3.805 (0.5H, m); 3.771 (3H, s); 3.765 (3H, s); 3.805-3.62 (3H, m); 3.62-3.475 (4H, m); 3.39-3.23 (2H, m); 2.46-230 (2H, m); 1.982, 1.965, 1.962, 1.954, 1.940, 1.935 (total 9H, singlets); 1.789 (1.5H, s); 1.777 (1.5H, s); 1.691 (2H, pent., J=6.5 Hz); 1.553 (1.5H, d, J=1.0 Hz); 1.490 (1.5H, d, J=1.0 Hz); 1.18-1.11 (9H, m); 1.040 (3H, d, J=7.0 Hz).

Example 34

N$^4$-Benzoyl-5'-O-(4,4'-dimethoxytrityl)-3'-O—[(N,N-diisopropylamino)[3-[(3,4,6-tri-O-acetyl-2-acetylamino-2-deoxy-β-D-glucopyranosyl)oxy]propoxy] phosphinyl]-2'-deoxycytidine (25a)

Solution of bis(N,N-diisopropylamino) chlorophosphite (3.20 g, 12.0 mmol) in anhydrous dichloromethane (15 mL) was added dropwise to a stirred solution of N$^4$-benzoyl-5'-O-(4,4'-dimethoxytrityl)-2'-deoxycytidine, 9a, (6.08 g, 9.6 mmol) and N-ethyl-N,N-diisopropylamine (2.36 g, 18.2 mmol) in anhydrous dichloromethane (30 mL) at −20° C. The solution was allowed to stir at room temperature for 2 h. To the obtained mixture, 1-O-(3-hydroxypropyl)-3,4,6-tri-O-acetyl-2-acetylamino-2-deoxy-β-D-glucopyranoside, 6, (4.48 g, 11.0 mmol) and 1H-tetrazole (0.45 M in MeCN, 8.5 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (10:90). Evaporation of fractions gave the target compound as white solid foam in a yield of 9.10 g (81.1%). $^{31}$P NMR (mixture of diastereomers, CD$_3$CN): δ 147.63, 147.21.

Example 35

N$^4$-Acetyl-5'-O-(4,4'-dimethoxytrityl)-3'-O—[(N,N-diisopropylamino) [3-[(3,4,6-tri-O-acetyl-2-acetylamino-2-deoxy-β-D-glucopyranosyl)oxy]propoxy] phosphinyl]-2'-deoxycytidine (25c)

Solution of bis(N,N-diisopropylamino) chlorophosphite (1.67 g, 6.25 mmol) in anhydrous dichloromethane (5 mL) was added dropwise to a stirred solution of N$^4$-acetyl-5'-O-(4,4'-dimethoxytrityl)-2'-deoxycytidine, 9c, (2.86 g, 5.0 mmol) and N-ethyl-N,N-diisopropylamine (12.3 g, 9.5 mmol) in anhydrous dichloromethane (15 mL) at −20° C. The solution was allowed to stir at room temperature for 2 h. To the obtained mixture, 1-O-(3-hydroxypropyl)-3,4,6-tri-O-acetyl-2-acetylamino-2-deoxy-β-D-glucopyranoside, 6, (2.33 g, 5.75 mmol) and 1H-tetrazole (0.45 M in MeCN, 4.5 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (10:90). Evaporation of fractions gave the title compound as white solid foam in a yield of 4.14 g (74.9%). $^{31}$P NMR (mixture of diastereomers, CD$_3$CN): δ 149.43, 148.77.

Example 36

N$^6$-Benzoyl-5'-O-(4,4'-dimethoxytrityl)-3'-O—[(N, N-diisopropylamino)[3-[(3,4,6-tri-O-acetyl-2-acetylamino-2-deoxy-β-D-glucopyranosyl)oxy]propoxy] phosphinyl]-2'-deoxyadenosine (26a)

Solution of bis(N,N-diisopropylamino) chlorophosphite (1.77 g, 6.63 mmol) in anhydrous dichloromethane (5 mL) was added dropwise to a stirred solution of N$^6$-benzoyl-5'-O-(4,4'-dimethoxytrityl)-2'-deoxyadenosine, 10a, (3.49 g, 5.3 mmol) and N-ethyl-N,N-diisopropylamine (1.30 g, 10.1 mmol) in anhydrous dichloromethane (15 mL) at −20° C. The solution was allowed to stir at room temperature for 2 h. To the obtained mixture, 1-O-(3-hydroxypropyl)-3,4,6-tri-O-acetyl-2-acetylamino-2-deoxy-β-D-glucopyranoside, 6, (2.47 g, 6.10 mmol) and 1H-tetrazole (0.45 M in MeCN, 4.7 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. Evaporation of fractions gave the title compound as white solid foam in a yield of 4.47 g (70.7%). $^{31}$P NMR (mixture of diastereomers, CD$_3$CN): δ 148.58, 148.11.

Example 37

N$^6$-Phenoxyacetyl-5'-O-(4,4'-dimethoxytrityl)-3'-O—[(N,N-diisopropylamino)[3-[(3,4,6-tri-O-acetyl-2-acetylamino-2-deoxy-β-D-glucopyranosyl)oxy] propoxy]phosphinyl]-2'-deoxyadenosine (26b)

Solution of bis(N,N-diisopropylamino) chlorophosphite (1.57 g, 5.88 mmol) in anhydrous dichloromethane (5 mL) was added dropwise to a stirred solution of N$^6$-phenoxyacetyl-5'-O-(4,4'-dimethoxytrityl)-2'-deoxyadenosine, 10b, (3.23 g, 4.70 mmol) and N-ethyl-N,N-diisopropylamine (1.15 g, 8.9 mmol) in anhydrous dichloromethane (15 mL) at −20° C. The solution was allowed to stir at room temperature for 2 h. To the obtained mixture, 1-O-(3-hydroxypropyl)-3,4,6-tri-O-acetyl-2-acetylamino-2-deoxy-β-D-glucopyranoside, 6, (2.19 g, 5.41 mmol) and 1H-tetrazole (0.45 M in MeCN, 4.2 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. Evaporation of fractions gave the title compound as white solid foam in a yield of 3.92 g (68.2%). $^{31}$P NMR (mixture of diastereomers, CD$_3$CN): δ 148.98, 148.29.

Example 38

N$^2$-Isobutyryl-5'-O-(4,4'-dimethoxytrityl)-3'-O—[(N, N-diisopropylamino)[3-[(3,4,6-tri-O-acetyl-2-acetylamino-2-deoxy-β-D-glucopyranosyl)oxy]propoxy] phosphinyl]-2'-deoxyguanosine (27a)

Solution of bis(N,N-diisopropylamino) chlorophosphite (2.23 g, 8.38 mmol) in anhydrous dichloromethane (15 mL) was added dropwise to a stirred solution of N$^2$-isobutyryl-5'-O-(4,4'-dimethoxytrityl)-2'-deoxyguanosine, 11a, (4.29 g, 6.70 mmol) and N-ethyl-N,N-diisopropylamine (1.64 g, 12.73 mmol) in anhydrous dichloromethane (30 mL) at −20° C. The solution was allowed to stir at room temperature for 2 h. To the obtained mixture, 1-O-(3-hydroxypropyl)-3,4,6-tri-O-acetyl-2-acetylamino-2-deoxy-β-D-glucopyranoside, 6, (3.12 g, 7.71 mmol) and 1H-tetrazole (0.45 M in MeCN, 6.0 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×100 mL). Extracts were washed with brine, dried over anhydrous Na$_2$SO$_4$, and evaporated to oil. Evaporation of fractions gave the title compound as white solid foam in a yield of 5.68 g (72.2%). $^{31}$P NMR (mixture of diastereomers, CD$_3$CN): δ 148.91, 148.33.

Example 39

N$^2$-Phenoxyacetyl-5'-O-(4,4'-dimethoxytrityl)-3'-O—[(N,N-diisopropylamino)[3-[(3,4,6-tri-O-acetyl-2-acetylamino-2-deoxy-β-D-glucopyranosyl)oxy] propoxy]phosphinyl]-2'-deoxyguanosine (27b)

Solution of bis(N,N-diisopropylamino) chlorophosphite (1.50 g, 5.63 mmol) in anhydrous dichloromethane (10 mL) was added dropwise to a stirred solution of N$^2$-phenoxyacetyl-5'-O-(4,4'-dimethoxytrityl)-2'-deoxyguanosine, 11b, (3.17 g, 4.50 mmol) and N-ethyl-N,N-diisopropylamine (1.10 g, 8.55 mmol) in anhydrous dichloromethane (20 mL) at −20° C. The solution was allowed to stir at room temperature for 2 h. To the obtained mixture, 1-O-(3-hydroxypropyl)-3,4,6-tri-O-acetyl-2-acetylamino-2-deoxy-β-D-glucopyranoside, 6, (2.10 g, 5.18 mmol) and 1H-tetrazole (0.45 M in MeCN, 4.0 mL) were added followed by stirring at room temperature for 14 h. The reaction mixture was quenched by addition of excess 5% aqueous NaHCO$_3$. The emulsion was diluted with 5% aqueous NaHCO$_3$ (100 mL), and the product was extracted with ethyl acetate (3×70 mL). Extracts were washed with brine, dried over anhydrous Na$_2$SO$_4$, and evaporated to oil. Evaporation of fractions gave the title compound as white solid foam in a yield of 3.66 g (65.7%). $^{31}$P NMR (mixture of diastereomers, CD$_3$CN): δ 148.72, 148.27.

Example 40

1-O-(5-Hydroxy-3-oxapentyl)-3,4,6-tri-O-acetyl-2-acetylamino-2-deoxy-β-D-galactopyranoside (7b)

A mixture of compound 5 (13.17 g, 40.0 mmol, prepared as disclosed in Fukase, K.; Ueno, A.; Fukase, Y; et al., *Bull.*

Chem. Soc. Japan 2003, 76, 485-500), anhydrous diethyleneglycol (42.5 g, 0.4 mol), and pyridinium p-toluenesulfonate (9.05 g, 36.0 mmol) was heated at 80° C. for 18 h, then distributed between DCM (300 mL) and a 1:1 mixture of brine and 5% aqueous NaHCO$_3$ (100 mL). The organic phase was separated, dried over Na$_2$SO$_4$, and evaporated in vacuo. The product was isolated by column chromatography on silica gel eluted with a step gradient from DCM to a mixture of MeOH and DCM (8:92). Evaporation of the relevant fractions gave the title compound as an off-white solid (7.92 g, 45.4%). $^1$H NMR (CD$_3$CN): δ 6.572 (1H, d, J=9.5 Hz); 5.278 (1H, d, J=3 Hz); 5.010 (1H, dd, J=11.5 Hz, J=3 Hz); 4.673 (1H, d, J=8.5 Hz); 4.109 (1H, dd, J=9 Hz, J=7 Hz); 4.066 (1H, dd, J=9 Hz, J=6 Hz); 3.951 (2H, m); 3.828 (1H, m); 3.703 (1H, m); 3.64-3.54 (4H, m); 3.54-3.45 (2H, m); 3.053 (1H, br. s); 2.098 (3H, s) 1.988 (3H, s); 1.910 (3H, s), 1.845 (3H, s). ES MS: 436.1 (MH$^+$). Calculated for C$_{18}$H$_{29}$NO$_{11}$H$^+$: 436.2.

Example 41

5'-O-(4,4'-Dimethoxytrityl)-3'-O—[(N,N-diisopropylamino)[5-[(3,4,6-tri-O-acetyl-2-acetylamino-2-deoxy-β-D-galactopyranosyl)oxy]-3-oxapentyloxy]phosphinyl]thymidine (28)

To the magnetically stirred mixture of 5'-O-(4,4'-dimethoxytrityl)thymidine, 8, (1.142 g, 2.10 mmol), N-ethyl-N,N-diisopropylamine (0.515 g, 3.99 mmol), and anhydrous CH$_3$CN (10 mL) was added a solution of N,N',N'-tetraisopropyl chlorophosphite (0.700 g, 2.63 mmol) in anhydrous DCM (5 mL) at –20° C. The mixture was allowed to warm up to room temperature over 2 h. A solution of 1-O-(5-hydroxy-3-oxapentyl)-3,4,6-tri-O-acetyl-2-acetylamino-2-deoxy-β-D-galactopyranoside, 7b, (1.097 g, 2.52 mmol) in anhydrous acetonitrile (5 mL) was added followed by the addition of a solution of 1H-tetrazole in acetonitrile (0.45 M, 1.87 mL). The reaction mixture was stirred for 18 h at room temperature and was quenched by adding 5% aqueous NaHCO$_3$. The product was extracted with ethyl acetate (3×50 mL). Combined extracts were washed with brine (50 mL), dried over anhydrous Na$_2$SO$_4$, and evaporated to dryness. The product was isolated by column chromatography on silica gel eluted with a step gradient starting from TEA—ethyl acetate—hexane (5:20:75) to a mixture of TEA in ethyl acetate (10:90). Evaporation of fractions gave compound 24 as white solid foam in a yield of 1.760 g (75.6%).

Fast diastereomer: $^1$H NMR (CD$_3$CN): δ 9.09 (1H, br. s); 7.5-7.4 (3H, m); 7.375-7.30 (6H, m); 7.30-7.23 (1H, m); 6.9-6.8 (4H, m); 6.335 (1H, d, J=9 Hz); 6.248 (1H, t, J=7 Hz); 5.31-5.27 (1H, m); 5.025 (1H, dd, J=11.2 Hz, J=3.5 Hz); 4.66-4.59 (1H, m); 4.565 (1H, d, J=8.5 Hz); 4.15-4.11 (1H, m); 4.11-4.03 (2H, m); 3.99-3.89 (2H, m); 3.84-3.70 (2H, m); 3.783 and 3.766 (total 6H, s, s); 3.67-3.53 (5H, m); 3.53-3.43 (4H, m); 3.355 (1H, dd, J=10.5 Hz, J=3.0 Hz); (1H, dd, J=10.5 Hz, J=3.5 Hz); 2.41-2.33 (2H, m); 2.090 (3H, s); 1.968 (3H, s), 1.913 (3H, s); 1.820 (3H, s); 1.480 (3H, d, J=0.5 Hz); 1.149 (12H, t, J=6.5 Hz). $^{31}$P NMR (CD$_3$CN): δ 149.99.

Slow diastereomer: $^1$H NMR (CD$_3$CN): δ 8.976 (1H, br. s); 7.5-7.4 (3H, m); 7.375-7.30 (6H, m); 7.30-7.23 (1H, m); 6.9-6.8 (4H, m); 6.358 (1H, d, J=9.5 Hz); 6.242 (1H, t, J=7 Hz); 5.29-5.27 (1H, m); 5.030 (1H, dd, J=11.5 Hz, J=3.5 Hz); 4.64-4.54 (2H, m); 4.15-4.03 (1H, m); 3.99-3.89 (2H, m); 3.85-3.79 (1H, m); 3.814 and 3.764 (total 6H, s, s); 3.78-3.70 (1H, m); 3.70-3.61 (2H, m); 3.61-3.48 (5H, m); 3.35-3.255 (1H, m); 2.46-2.39 (1H, m); 2.37-2.29 (1H, m); 2.094 (3H, s); 1.974 (3H, s), 1.913 (3H, s); 1.832 (3H, s); 1.498 (3H, s); 1.143 (6H, d, J=6.5 Hz); 1.051 (6H, d, J=6.5 Hz). $^{31}$P NMR (CD$_3$CN): δ 149.67.

Example 42

N$^4$-Benzoyl-5'-O-(4,4'-dimethoxytrityl)-3'-O—[(N,N-diisopropylamino)[5-[(3,4,6-tri-O-acetyl-2-acetylamino-2-deoxy-β-D-galactopyranosyl)oxy]-3-oxapentyloxy]phosphinyl]-2'-deoxycytidine (29a)

Solution of bis(N,N-diisopropylamino) chlorophosphite (667 mg, 2.50 mmol) in anhydrous dichloromethane (5 mL) was added dropwise to a stirred solution of N$^4$-benzoyl-5'-O-(4,4'-dimethoxytrityl)-2'-deoxycytidine, 9a, (1267 mg, 2.0 mmol) and N-ethyl-N,N-diisopropylamine (491 mg, 3.80 mmol) in anhydrous dichloromethane (10 mL) at –20° C. The solution was allowed to stir at room temperature for 2 h. To the obtained mixture, compound 7b (1045 mg, 2.40 mmol) and 1H-tetrazole (0.45 M in MeCN, 1.8 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (10:90). Evaporation of fractions gave the target compound as white solid foam in a yield of 1769 mg (73.8%). $^{31}$P NMR (mixture of diastereomers, CD$_3$CN): δ 148.91, 148.37.

Example 43

N$^4$-Acetyl-5'-O-(4,4'-dimethoxytrityl)-3'-O—[(N,N-diisopropylamino) [5-[(3,4,6-tri-O-acetyl-2-acetylamino-2-deoxy-β-D-galactopyranosyl)oxy]-3-oxapentyloxy]phosphinyl]-2'-deoxycytidine (29c)

Solution of bis(N,N-diisopropylamino) chlorophosphite (767 mg, 2.88 mmol) in anhydrous dichloromethane (5 mL) was added dropwise to a stirred solution of N$^4$-acetyl-5'-O-(4,4'-dimethoxytrityl)-2'-deoxycytidine, 9c, (1315 mg, 2.30 mmol) and N-ethyl-N,N-diisopropylamine (564 mg, 4.37 mmol) in anhydrous dichloromethane (10 mL) at –20° C. The solution was allowed to stir at room temperature for 2 h. To the obtained mixture, compound 7b (1202 mg, 2.76 mmol) and 1H-tetrazole (0.45 M in MeCN, 2.1 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (10:90). Evaporation of fractions gave the title compound as white solid foam in a yield of 1835 mg (70.2%). $^{31}$P NMR (mixture of diastereomers, CD$_3$CN): δ 148.78, 148.11.

Example 44

N[6]-Benzoyl-5'-O-(4,4'-dimethoxytrityl)-3'-O—[(N,N-diisopropylamino)[5-[(3,4,6-tri-O-acetyl-2-acetylamino-2-deoxy-β-D-galactopyranosyl)oxy]-3-oxapentyloxy]phosphinyl]-2'-deoxyadenosine (30a)

Solution of bis(N,N-diisopropylamino) chlorophosphite (750 mg, 2.81 mmol) in anhydrous dichloromethane (5 mL) was added dropwise to a stirred solution of N[6]-benzoyl-5'-O-(4,4'-dimethoxytrityl)-2'-deoxyadenosine, 10a, (1480, 2.25 mmol) and N-ethyl-N,N-diisopropylamine (552 mg, 4.28 mmol) in anhydrous dichloromethane (10 mL) at −20° C. The solution was allowed to stir at room temperature for 2 h. To the obtained mixture, compound 7b (1176 mg, 2.70 mmol) and 1H-tetrazole (0.45 M in MeCN, 2.0 mL) were added followed by stirring at room temperature for 14 h. The reaction mixture was quenched by addition of excess 5% aqueous $NaHCO_3$. The emulsion was diluted with 5% aqueous $NaHCO_3$ (30 mL), and the product was extracted with ethyl acetate (3×50 mL). Extracts were washed with brine, dried over anhydrous $Na_2SO_4$, and evaporated to oil. Evaporation of fractions gave the title compound as white solid foam in a yield of 1851 mg (67.3%). $^{31}$P NMR (mixture of diastereomers, $CD_3CN$): δ 148.83, 148.23.

Example 45

N[6]-Phenoxyacetyl-5'-O-(4,4'-dimethoxytrityl)-3'-O—[(N,N-diisopropylamino)[5-[(3,4,6-tri-O-acetyl-2-acetylamino-2-deoxy-β-D-galactopyranosyl)oxy]-3-oxapentyloxy]phosphinyl]-2'-deoxyadenosine (30b)

Solution of bis(N,N-diisopropylamino) chlorophosphite (700, 2.63 mmol) in anhydrous dichloromethane (5 mL) was added dropwise to a stirred solution of N[6]-phenoxyacetyl-5'-O-(4,4'-dimethoxytrityl)-2'-deoxyadenosine, 10b, (1444 mg, 2.10 mmol) and N-ethyl-N,N-diisopropylamine (515 mg, 3.99 mmol) in anhydrous dichloromethane (10 mL) at −20° C. The solution was allowed to stir at room temperature for 2 h. To the obtained mixture, compound 7b (1097 mg, 2.52 mmol) and 1H-tetrazole (0.45 M in MeCN, 1.9 mL) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×50 mL). Extracts were washed with brine, dried over anhydrous $Na_2SO_4$, and evaporated to oil. Evaporation of fractions gave the title compound as white solid foam in a yield of 1681 mg (63.9%). $^{31}$P NMR (mixture of diastereomers, $CD_3CN$): δ 147.94, 147.52.

Example 46

N[2]-Isobutyryl-5'-O-(4,4'-dimethoxytrityl)-3'-O—[(N,N-diisopropylamino)[5-[(3,4,6-tri-O-acetyl-2-acetylamino-2-deoxy-β-D-galactopyranosyl)oxy]-3-oxapentyloxy]phosphinyl]-2'-deoxyguanosine (31a)

Solution of bis(N,N-diisopropylamino) chlorophosphite (734 mg, 2.75 mmol) in anhydrous dichloromethane (5 mL) was added dropwise to a stirred solution of N[2]-isobutyryl-5'-O-(4,4'-dimethoxytrityl)-2'-deoxyguanosine, 11a, (1407 mg, 2.20 mmol) and N-ethyl-N,N-diisopropylamine (540 mg, 4.18 mmol) in anhydrous dichloromethane (10 mL) at −20° C. The solution was allowed to stir at room temperature for 2 h. To the obtained mixture, compound 7b (1149 mg, 2.64 mmol) and 1H-tetrazole (0.45 M in MeCN, 2.0 mL) were added followed by stirring at room temperature for 14 h. The reaction mixture was quenched by addition of excess 5% aqueous $NaHCO_3$. The emulsion was diluted with 5% aqueous $NaHCO_3$ (30 mL), and the product was extracted with ethyl acetate (3×50 mL). Extracts were washed with brine, dried over anhydrous $Na_2SO_4$, and evaporated to oil. Evaporation of fractions gave the title compound as white solid foam in a yield of 1706 mg (64.4%). $^{31}$P NMR (mixture of diastereomers, $CD_3CN$): δ 147.88, 147.43.

Example 47

N[2]-Phenoxyacetyl-5'-O-(4,4'-dimethoxytrityl)-3'-O—[(N,N-diisopropylamino)[5-[(3,4,6-tri-O-acetyl-2-acetylamino-2-deoxy-β-D-galactopyranosyl)oxy]-3-oxapentyloxy]phosphinyl]-2'-deoxyguanosine (31b)

Solution of bis(N,N-diisopropylamino) chlorophosphite (750 mg, 2.81 mmol) in anhydrous dichloromethane (5 mL) was added dropwise to a stirred solution of N[2]-phenoxyacetyl-5'-O-(4,4'-dimethoxytrityl)-2'-deoxyguanosine, 11b, (1583 mg, 2.25 mmol) and N-ethyl-N,N-diisopropylamine (552 mg, 4.28 mmol) in anhydrous dichloromethane (10 mL) at −20° C. The solution was allowed to stir at room temperature for 2 h. To the obtained mixture, compound 7b (1176 mg, 2.70 mmol) and 1H-tetrazole (0.45 M in MeCN, 2.0 mL) were added followed by stirring at room temperature for 14 h. The reaction mixture was quenched by addition of excess 5% aqueous $NaHCO_3$. The emulsion was diluted with 5% aqueous $NaHCO_3$ (50 mL), and the product was extracted with ethyl acetate (3×50 mL). Extracts were washed with brine, dried over anhydrous $Na_2SO_4$, and evaporated to oil. Evaporation of fractions gave the title compound as white solid foam in a yield of 1758 mg (61.6%). $^{31}$P NMR (mixture of diastereomers, $CD_3CN$): δ 147.80, 147.39.

Example 48

1-O-(8-Hydroxy-3,6-dioxaoctyl)-3,4,6-tri-O-acetyl-2-acetylamino-2-deoxy-β-D-galactopyranoside (7c)

A mixture of compound 5 (3.29 g, 10.0 mmol), anhydrous triethyleneglycol (12.0 g, 80 mmol), and pyridinium p-toluenesulfonate (2.26 g, 9.0 mmol) was heated at 80° C. for 18 h, then distributed between DCM (70 mL) and a 1:1 mixture of brine and 5% aqueous $NaHCO_3$ (100 mL). The organic phase was separated, dried over $Na_2SO_4$, and evaporated in vacuo. The product was isolated by column chromatography on silica gel eluted with a step gradient from DCM to a mixture of MeOH and DCM (8:92). Evaporation of the relevant fractions gave the title compound as an off-white solid (2.32 g, 48.4%). ES MS: 480.2 (MH[+]). Calculated for $C_{18}H_{29}NO_{11}$.H[+]: 480.2.

Example 49

5'-O-(4,4'-Dimethoxytrityl)-3'-O—[(N,N-diisopropylamino)[8-[(3,4,6-tri-O-acetyl-2-acetylamino-2-deoxy-β-D-galactopyranosyl)oxy]-3,6-dioxaoctyloxy]phosphinyl]thymidine (32)

Solution of bis(N,N-diisopropylamino) chlorophosphite (347 mg, 1.30 mmol) in anhydrous dichloromethane (5 mL)

was added dropwise to a stirred solution of 5'-O-(4,4'-dimethoxytrityl)thymidine, 8, (566 mg, 1.04 mmol) and N-ethyl-N,N-diisopropylamine (255 mg, 1.98 mmol) in anhydrous dichloromethane (5 mL) at −20° C. The solution was allowed to stir at room temperature for 2 h. To the obtained mixture, 1-O-(8-hydroxy-3,6-dioxaoctyl)-3,4,6-tri-O-acetyl-2-acetylamino-2-deoxy-β-D-galactopyranoside, 7c, (598 mg, 1.25 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as white solid foam in a yield of 920 mg (76.7%). $^{31}$P NMR (mixture of diastereomers, CD$_3$CN): δ 147.95, 147.41.

Example 50

N$^4$-Benzoyl-5'-O-(4,4'-dimethoxytrityl)-3'-O—[(N,N-diisopropylamino)[8-[(3,4,6-tri-O-acetyl-2-acetylamino-2-deoxy-β-D-galactopyranosyl)oxy]-3,6-dioxaoctyloxy]phosphinyl]-2'-deoxycytidine (33a)

Solution of bis(N,N-diisopropylamino) chlorophosphite (357 mg, 1.34 mmol) in anhydrous dichloromethane (5 mL) was added dropwise to a stirred solution of N$^4$-benzoyl-5'-O-(4,4'-dimethoxytrityl)-2'-deoxycytidine, 9a, (678 mg, 1.7 mmol) and N-ethyl-N,N-diisopropylamine (263 mg, 2.03 mmol) in anhydrous dichloromethane (5 mL) at −20° C. The solution was allowed to stir at room temperature for 2 h. To the obtained mixture, compound 7c (616 mg, 1.28 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as white solid foam in a yield of 980 mg (73.7%). $^{31}$P NMR (mixture of diastereomers, CD$_3$CN): δ 148.22, 147.62.

Example 51

N$^4$-Acetyl-5'-O-(4,4'-dimethoxytrityl)-3'-O—[(N,N-diisopropylamino) [8-[(3,4,6-tri-O-acetyl-2-acetylamino-2-deoxy-β-D-galactopyranosyl)oxy]-3,6-dioxaoctyloxy]phosphinyl]-2'-deoxycytidine (33c)

Solution of bis(N,N-diisopropylamino) chlorophosphite (333 mg, 1.25 mmol) in anhydrous dichloromethane (5 mL) was added dropwise to a stirred solution of N$^4$-acetyl-5'-O-(4,4'-dimethoxytrityl)-2'-deoxycytidine, 9c, (572 mg, 1.0 mmol) and N-ethyl-N,N-diisopropylamine (245 mg, 1.90 mmol) in anhydrous dichloromethane (5 mL) at −20° C. The solution was allowed to stir at room temperature for 2 h. To the obtained mixture, compound 7c (575 mg, 1.20 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as white solid foam in a yield of 829 mg (70.2%). $^{31}$P NMR (mixture of diastereomers, CD$_3$CN): δ 148.08, 147.72.

Example 52

N$^6$-Benzoyl-5'-O-(4,4'-dimethoxytrityl)-3'-O—[(N,N-diisopropylamino)[8-[(3,4,6-tri-O-acetyl-2-acetylamino-2-deoxy-β-D-galactopyranosyl)oxy]-3,6-dioxaoctyloxy]phosphinyl]-2'-deoxyadenosine (34a)

Solution of bis(N,N-diisopropylamino) chlorophosphite (340 mg, 1.28 mmol) in anhydrous dichloromethane (5 mL) was added dropwise to a stirred solution of N$^6$-benzoyl-5'-O-(4,4'-dimethoxytrityl)-2'-deoxyadenosine, 10a, (671, 1.02 mmol) and N-ethyl-N,N-diisopropylamine (250 mg, 1.94 mmol) in anhydrous dichloromethane (5 mL) at −20° C. The solution was allowed to stir at room temperature for 2 h. To the obtained mixture, compound 7c (587 mg, 1.22 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×50 mL). Extracts were washed with brine, dried over anhydrous Na$_2$SO$_4$, and evaporated to oil. Evaporation of fractions gave the title compound as white solid foam in a yield of 831 mg (64.3%). $^{31}$P NMR (mixture of diastereomers, CD$_3$CN): δ 148.19, 147.47.

Example 53

N$^6$-Phenoxyacetyl-5'-O-(4,4'-dimethoxytrityl)-3'-O—[(N,N-diisopropylamino)[8-[(3,4,6-tri-O-acetyl-2-acetylamino-2-deoxy-β-D-galactopyranosyl)oxy]-3,6-dioxaoctyloxy]phosphinyl]-2'-deoxyadenosine (34b)

Solution of bis(N,N-diisopropylamino) chlorophosphite (370, 1.39 mmol) in anhydrous dichloromethane (5 mL) was added dropwise to a stirred solution of N$^6$-phenoxyacetyl-5'-O-(4,4'-dimethoxytrityl)-2'-deoxyadenosine, 10b, (763 mg, 1.11 mmol) and N-ethyl-N,N-diisopropylamine (272 mg, 2.11 mmol) in anhydrous dichloromethane (5 mL) at −20° C. The solution was allowed to stir at room temperature for 2 h. To the obtained mixture, compound 7c (639 mg, 1.33 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (40 mL), and the product was extracted with ethyl acetate (3×50 mL). Extracts were washed with brine, dried over anhydrous Na$_2$SO$_4$, and evaporated to oil. Evaporation of fractions gave the title compound as white solid foam in a yield of 872 mg (60.6%). $^{31}$P NMR (mixture of diastereomers, CD$_3$CN): δ 148.51, 147.90.

Example 54

N$^2$-Isobutyryl-5'-O-(4,4'-dimethoxytrityl)-3'-O—[(N,N-diisopropylamino)[8-[(3,4,6-tri-O-acetyl-2-acetylamino-2-deoxy-β-D-galactopyranosyl)oxy]-3,6-dioxaoctyloxy]phosphinyl]-2'-deoxyguanosine (35a)

Solution of bis(N,N-diisopropylamino) chlorophosphite (320 mg, 1.20 mmol) in anhydrous dichloromethane (5 mL) was added dropwise to a stirred solution of N$^2$-isobutyryl-5'-O-(4,4'-dimethoxytrityl)-2'-deoxyguanosine, 11a, (614 mg, 0.96 mmol) and N-ethyl-N,N-diisopropylamine (236 mg, 1.82 mmol) in anhydrous dichloromethane (5 mL) at −20° C. The solution was allowed to stir at room temperature for 2 h. To the obtained mixture, compound 7c (552 mg, 1.15 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (40 mL), and the product was extracted with ethyl acetate (3×50 mL). Extracts were washed with brine, dried over anhydrous Na$_2$SO$_4$, and evaporated to oil. Evaporation of fractions gave the title compound as white solid foam in a yield of 784 mg (65.4%). $^{31}$P NMR (mixture of diastereomers, CD$_3$CN): δ 147.60, 147.11.

Example 55

N$^2$-Phenoxyacetyl-5'-O-(4,4'-dimethoxytrityl)-3'-O—[(N,N-diisopropylamino)[8-[(3,4,6-tri-O-acetyl-2-acetylamino-2-deoxy-β-D-galactopyranosyl)oxy]-3,6-dioxaoctyloxy]phosphinyl]-2'-deoxyguanosine (35b)

Solution of bis(N,N-diisopropylamino) chlorophosphite (330 mg, 1.24 mmol) in anhydrous dichloromethane (5 mL) was added dropwise to a stirred solution of N$^2$-phenoxyacetyl-5'-O-(4,4'-dimethoxytrityl)-2'-deoxyguanosine, 11b, (697 mg, 0.99 mmol) and N-ethyl-N,N-diisopropylamine (243 mg, 1.88 mmol) in anhydrous dichloromethane (10 mL) at −20° C. The solution was allowed to stir at room temperature for 2 h. To the obtained mixture, compound 7c (570 mg, 1.19 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. Evaporation of fractions gave the title compound as white solid foam in a yield of 803 mg (61.8%). $^{31}$P NMR (mixture of diastereomers, CD$_3$CN): δ 148.55, 147.73.

Example 56

1-O-(11-Hydroxy-3,6,9-trioxaundecyl)-3,4,6-tri-O-acetyl-2-acetylamino-2-deoxy-β-D-galactopyranoside (7d)

A mixture of compound 5 (7.25 g, 22.0 mmol), anhydrous tetraethyleneglycol (34.2 g, 176 mmol), and pyridinium p-toluenesulfonate (4.98 g, 19.8 mmol) was heated at 80° C. for 18 h, then distributed between DCM (50 mL) and a 1:1 mixture of brine and 5% aqueous NaHCO$_3$ (100 mL). The organic phase was separated, dried over Na$_2$SO$_4$, and evaporated in vacuo. The product was isolated by column chromatography on silica gel eluted with a step gradient from DCM to a mixture of MeOH and DCM (8:92). Evaporation of the relevant fractions gave the title compound as an off-white solid (4.92 g, 42.7%). ES MS: 524.4 (MH$^+$). Calculated for C$_{18}$H$_{29}$NO$_{11}$.H$^+$: 524.2.

Example 57

5'-O-(4,4'-Dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]thymidine (36)

Figure 10:
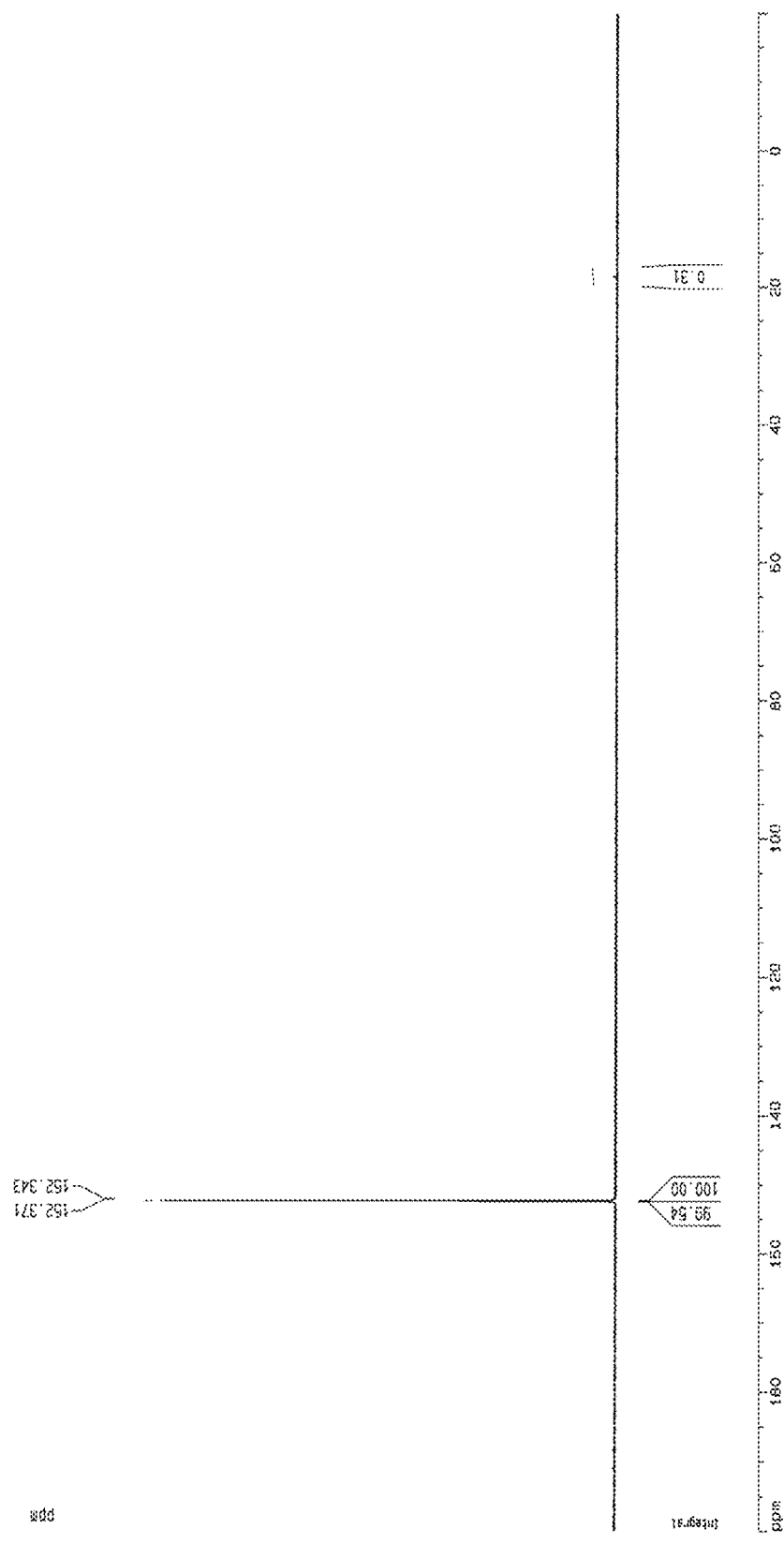
FIG. 10 shows an exemplary $^{31}P$ NMR spectrum of 5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]thymidine (36, Example 57).

Solution of bis(N,N-diisopropylamino) chlorophosphite (370 mg, 1.39 mmol) in anhydrous dichloromethane (5 mL) was added dropwise to a stirred solution of 5'-O-(4,4'-dimethoxytrityl)thymidine, 8, (604 mg, 1.11 mmol) and N-ethyl-N,N-diisopropylamine (272 mg, 2.11 mmol) in anhydrous dichloromethane (5 mL) at −20° C. The solution was allowed to stir at room temperature for 2 h. To the obtained mixture, 1-O-(11-hydroxy-3,6,9-trioxaundecyl)-3,4,6-tri-O-acetyl-2-acetylamino-2-deoxy-β-D-galactopyranoside, 7d, (697 mg, 1.33 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 1099 mg (82.7%). $^{31}$P NMR (mixture of diastereomers, CD$_3$CN; see FIG. 10): δ 152.37, 152.3.

Example 58

N$^4$-Benzoyl-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]-2'-deoxycytidine (37a)

Solution of bis(N,N-diisopropylamino) chlorophosphite (313 mg, 1.18 mmol) in anhydrous dichloromethane (5 mL) was added dropwise to a stirred solution of N$^4$-benzoyl-5'-O-(4,4'-dimethoxytrityl)-2'-deoxycytidine, 9a, (596 mg, 0.94 mmol) and N-ethyl-N,N-diisopropylamine (231 mg, 1.79 mmol) in anhydrous dichloromethane (5 mL) at −20° C. The solution was allowed to stir at room temperature for 2 h. To the obtained mixture, compound 7d (590 mg, 1.13 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 940 mg (77.7%). $^{31}$P NMR (mixture of diastereomers, CD$_3$CN): δ 150.06, 149.74.

Example 59

N$^4$-Phenoxyacetyl-5'-O-(4,4'-dimethoxytrityl)-3'-O—[(N,N-diisopropylamino) [11-[(3,4,6-tri-O-acetyl-2-acetylamino-2-deoxy-β-D-galactopyranosyl)oxy]-3,6,9-trioxaundecyloxy]phosphinyl]-2'-deoxycytidine (37b)

Solution of bis(N,N-diisopropylamino) chlorophosphite (323 mg, 1.21 mmol) in anhydrous dichloromethane (5 mL) was added dropwise to a stirred solution of N$^4$-phenoxyacetyl-5'-O-(4,4'-dimethoxytrityl)-2'-deoxycytidine, 9b, (644 mg, 0.97 mmol) and N-ethyl-N,N-diisopropylamine (238 mg, 1.84 mmol) in anhydrous dichloromethane (5 mL) at −20° C. The solution was allowed to stir at room temperature for 2 h. To the obtained mixture, compound 7d (609 mg, 1.16 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate-hexane (5:20:75) to a mixture of TEA in ethyl acetate (5:95). Evaporation of fractions gave the title compound as a viscous oil in a yield of 1014 mg (79.4%). $^{31}$P NMR (mixture of diastereomers, CD$_3$CN): δ 151.67, 151.24.

Example 60

N$^4$-Acetyl-5'-O-(4,4'-dimethoxytrityl)-3'-O—[(N,N-diisopropylamino) [11-[(3,4,6-tri-O-acetyl-2-acetylamino-2-deoxy-β-D-galactopyranosyl)oxy]-3,6,9-trioxaundecyloxy]phosphinyl]-2'-deoxycytidine (37c)

Solution of bis(N,N-diisopropylamino) chlorophosphite (340 mg, 1.28 mmol) in anhydrous dichloromethane (5 mL) was added dropwise to a stirred solution of N$^4$-acetyl-5'-O-(4,4'-dimethoxytrityl)-2'-deoxycytidine, 9c, (583 mg, 1.02 mmol) and N-ethyl-N,N-diisopropylamine (250 mg, 1.94 mmol) in anhydrous dichloromethane (5 mL) at −20° C. The solution was allowed to stir at room temperature for 2 h. To the obtained mixture, compound 7d (641 mg, 1.22 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as viscous oil in a yield of 998 mg (79.9%). $^{31}$P NMR (mixture of diastereomers, CD$_3$CN): δ 149.82, 149.19.

Example 61

N$^6$-Benzoyl-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]-2'-deoxyadenosine (38a)

Solution of bis(N,N-diisopropylamino) chlorophosphite (327 mg, 1.23 mmol) in anhydrous dichloromethane (5 mL) was added dropwise to a stirred solution of N$^6$-benzoyl-5'-O-(4,4'-dimethoxytrityl)-2'-deoxyadenosine, 10a, (645, 0.98 mmol) and N-ethyl-N,N-diisopropylamine (240 mg, 1.86 mmol) in anhydrous dichloromethane (5 mL) at −20° C. The solution was allowed to stir at room temperature for 2 h. To the obtained mixture, compound 7d (616 mg, 1.18 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (50 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 944 mg (73.5%). $^{31}$P NMR (mixture of diastereomers, CD$_3$CN): δ 150.09, 149.36.

Example 62

N$^6$-Phenoxyacetyl-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]-2'-deoxyadenosine (38b)

Solution of bis(N,N-diisopropylamino) chlorophosphite (333, 1.25 mmol) in anhydrous dichloromethane (5 mL) was added dropwise to a stirred solution of N$^6$-phenoxyacetyl-5'-O-(4,4'-dimethoxytrityl)-2'-deoxyadenosine, 10b, (688 mg, 1.0 mmol) and N-ethyl-N,N-diisopropylamine (245 mg, 1.90 mmol) in anhydrous dichloromethane (5 mL) at −20° C. The solution was allowed to stir at room temperature for 2 h. To the obtained mixture, compound 7d (628 mg, 1.20 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (40 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 913 mg (68.1%). $^{31}$P NMR (mixture of diastereomers, CD$_3$CN): δ 149.84, 149.23.

Example 63

N$^6$-(4-i-Propylphenoxyacetyl)-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]-2'-deoxyadenosine (38c)

Solution of bis(N,N-diisopropylamino) chlorophosphite (340, 1.28 mmol) in anhydrous dichloromethane (5 mL) was added dropwise to a stirred solution of N$^6$-(4-i-propylphenoxy acetyl)-5'-O-(4,4'-dimethoxytrityl)-2'-deoxyadenosine, 10c, (744 mg, 1.02 mmol) and N-ethyl-N,N-diisopropylamine (250 mg, 1.94 mmol) in anhydrous dichloromethane (5 mL) at −20° C. The solution was allowed to stir at room temperature for 2 h. To the obtained mixture, compound 7d (641 mg, 1.22 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (40 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 982 mg (69.6%). $^{31}$P NMR (mixture of diastereomers, CD$_3$CN): δ 149.91, 149.42.

Example 64

N$^6$—(N,N-dimethylformamidino)-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]-2'-deoxyadenosine (38d)

Solution of bis(N,N-diisopropylamino) chlorophosphite (320, 1.20 mmol) in anhydrous dichloromethane (5 mL) was added dropwise to a stirred solution of N$^6$—(N,N-dimethylformamidino)-5'-O-(4,4'-dimethoxytrityl)-2'-deoxyadenosine, 10d, (584 mg, 0.96 mmol) and N-ethyl-N,N-diisopropylamine (236 mg, 1.82 mmol) in anhydrous dichloromethane (5 mL) at −20° C. The solution was allowed to stir at room temperature for 2 h. To the obtained mixture, compound 7d (603 mg, 1.15 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (40 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 798 mg (65.9%). $^{31}$P NMR (mixture of diastereomers, CD$_3$CN): δ 151.19, 150.55.

Example 65

N$^2$-Isobutyryl-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]-2'-deoxyguanosine (39a)

Solution of bis(N,N-diisopropylamino) chlorophosphite (343 mg, 1.29 mmol) in anhydrous dichloromethane (5 mL) was added dropwise to a stirred solution of N$^2$-isobutyryl-5'-O-(4,4'-dimethoxytrityl)-2'-deoxyguanosine, 11a, (659 mg, 1.03 mmol) and N-ethyl-N,N-diisopropylamine (253 mg, 1.96 mmol) in anhydrous dichloromethane (5 mL) at −20° C. The solution was allowed to stir at room temperature for 2 h. To the obtained mixture, compound 7d (647 mg, 1.24 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (40 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 900 mg (67.6%). $^{31}$P NMR (mixture of diastereomers, CD$_3$CN): δ 152.01, 151.92.

Example 66

N$^2$-Phenoxyacetyl-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]-2'-deoxyguanosine (39b)

Solution of bis(N,N-diisopropylamino) chlorophosphite (340 mg, 1.28 mmol) in anhydrous dichloromethane (5 mL) was added dropwise to a stirred solution of N$^2$-phenoxyacetyl-5'-O-(4,4'-dimethoxytrityl)-2'-deoxyguanosine, 11b, (718 mg, 1.02 mmol) and N-ethyl-N,N-diisopropylamine (250 mg, 1.94 mmol) in anhydrous dichloromethane (10 mL) at −20° C. The solution was allowed to stir at room temperature for 2 h. To the obtained mixture, compound 7d (641 mg, 1.22 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 944 mg (68.2%). $^{31}$P NMR (mixture of diastereomers, CD$_3$CN): δ 151.95, 151.36.

Example 67

N$^2$-(4-i-Propylphenoxyacetyl)-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyl]-3-oxapentyloxy]phosphinyl]-2'-deoxyguanosine (39c)

Solution of bis(N,N-diisopropylamino) chlorophosphite (333 mg, 1.25 mmol) in anhydrous dichloromethane (5 mL) was added dropwise to a stirred solution of N$^2$-(4-i-propylphenoxy acetyl)-5'-O-(4,4'-dimethoxytrityl)-2'-deoxyguanosine, 11c, (746 mg, 1.0 mmol) and N-ethyl-N,N-diisopropylamine (245 mg, 1.90 mmol) in anhydrous dichloromethane (10 mL) at −20° C. The solution was allowed to stir at room temperature for 2 h. To the obtained mixture, compound 7d (628 mg, 1.20 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 860 mg (61.5%). $^{31}$P NMR (mixture of diastereomers, CD$_3$CN): δ 150.29, 149.95.

Example 68

N$^2$—(N,N-Dimethylformamidino)-5'-O-(4,4'-dimethoxytrityl)-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl]-2'-deoxyguanosine (39d)

Solution of bis(N,N-diisopropylamino) chlorophosphite (317 mg, 1.19 mmol) in anhydrous dichloromethane (5 mL)

was added dropwise to a stirred solution of N²—(N,N-dimethylformamidino)-5'-O-(4,4'-dimethoxytrityl)-2'-deoxyguanosine, 11d, (594 mg, 0.95 mmol) and N-ethyl-N,N-diisopropylamine (233 mg, 1.81 mmol) in anhydrous dichloromethane (10 mL) at −20° C. The solution was allowed to stir at room temperature for 2 h. To the obtained mixture, compound 7d (597 mg, 1.14 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (30 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 808 mg (66.6%). $^{31}$P NMR (mixture of diastereomers, CD$_3$CN): δ 150.03, 149.72.

Example 69

1-O-(14-Hydroxy-3,6,9,12-tetraoxatetradecyl)-3,4,6-tri-O-acetyl-2-acetylamino-2-deoxy-β-D-galactopyranoside (7e)

A mixture of compound 5 (1.64 g, 5.0 mmol), anhydrous pentaethyleneglycol (7.15 g, 30.0 mol), and pyridinium p-toluenesulfonate (1.13 g, 4.5 mmol) was heated at 80° C. for 18 h, then distributed between DCM (50 mL) and a 1:1 mixture of brine and 5% aqueous NaHCO$_3$ (25 mL). The organic phase was separated, dried over Na$_2$SO$_4$, and evaporated in vacuo. The product was isolated by column chromatography on silica gel eluted with a step gradient from DCM to a mixture of MeOH and DCM (8:92). Evaporation of the relevant fractions gave the title compound as an off-white solid (1.08 g, 38.1%). ES MS: 568.0 (MH$^+$). Calculated for C$_{18}$H$_{29}$NO$_{11}$.H$^+$: 568.2.

Example 70

5'-O-(4,4'-Dimethoxytrityl)-3'-O—[(N,N-diisopropylamino)[14-[(3,4,6-tri-O-acetyl-2-acetylamino-2-deoxy-β-D-galactopyranosyl)oxy]-3,6,9,12-tetraoxatetradecyloxy]phosphinyl]thymidine (40)

Solution of bis(N,N-diisopropylamino) chlorophosphite (213 mg, 0.8 mmol) in anhydrous dichloromethane (3 mL) was added dropwise to a stirred solution of 5'-O-(4,4'-dimethoxytrityl)thymidine, 8, (348 mg, 0.64 mmol) and N-ethyl-N,N-diisopropylamine (157 mg, 1.22 mmol) in anhydrous dichloromethane (4 mL) at −20° C. The solution was allowed to stir at room temperature for 2 h. To the obtained mixture, 1-O-(14-hydroxy-3,6,9,12-tetraoxatetradecyl)-3,4,6-tri-O-acetyl-2-acetylamino-2-deoxy-β-D-galactopyranoside, 7e, (436 mg, 0.77 mmol) and 1H-tetrazole (0.45 M in MeCN, 0.6 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 617 mg (77.7%). $^{31}$P NMR (mixture of diastereomers, CD$_3$CN): δ 149.99, 149.66.

Example 71

N⁴-Benzoyl-5'-O-(4,4'-dimethoxytrityl)-3'-O—[(N,N-diisopropylamino)[14-[(3,4,6-tri-O-acetyl-2-acetylamino-2-deoxy-β-D-galactopyranosyl)oxy]-3,6,9,12-tetraoxatetradecyloxy]phosphinyl]-2'-deoxycytidine (41a)

Solution of bis(N,N-diisopropylamino) chlorophosphite (240 mg, 0.90 mmol) in anhydrous dichloromethane (3 mL) was added dropwise to a stirred solution of N⁴-benzoyl-5'-O-(4,4'-dimethoxytrityl)-2'-deoxycytidine, 9a, (456 mg, 0.72 mmol) and N-ethyl-N,N-diisopropylamine (177 mg, 1.37 mmol) in anhydrous dichloromethane (4 mL) at −20° C. The solution was allowed to stir at room temperature for 2 h. To the obtained mixture, compound 7e (490 mg, 0.86 mmol) and 1H-tetrazole (0.45 M in MeCN, 0.7 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 692 mg (72.2%). $^{31}$P NMR (mixture of diastereomers, CD$_3$CN): δ 148.17, 147.63.

Example 72

N⁴-Acetyl-5'-O-(4,4'-dimethoxytrityl)-3'-O—[(N,N-diisopropylamino)[14-[(3,4,6-tri-O-acetyl-2-acetylamino-2-deoxy-β-D-galactopyranosyl)oxy]-3,6,9,12-tetraoxatetradecyloxy]phosphinyl]-2'-deoxycytidine (41c)

Solution of bis(N,N-diisopropylamino) chlorophosphite (220 mg, 0.83 mmol) in anhydrous dichloromethane (3 mL) was added dropwise to a stirred solution of N⁴-acetyl-5'-O-(4,4'-dimethoxytrityl)-2'-deoxycytidine, 9c, (377 mg, 0.66 mmol) and N-ethyl-N,N-diisopropylamine (157 mg, 1.22 mmol) in anhydrous dichloromethane (4 mL) at −20° C. The solution was allowed to stir at room temperature for 2 h. To the obtained mixture, compound 7e (450 mg, 0.79 mmol) and 1H-tetrazole (0.45 M in MeCN, 0.6 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 590 mg (70.5%). $^{31}$P NMR (mixture of diastereomers, CD$_3$CN): δ 147.88, 147.21.

Example 73

N[6]-Benzoyl-5'-O-(4,4'-dimethoxytrityl)-3'-O—[(N, N-diisopropylamino)[14-[(3,4,6-tri-O-acetyl-2-acetylamino-2-deoxy-β-D-galactopyranosyl)oxy]-3, 6,9,12-tetraoxatetradecyloxy]phosphinyl]-2'-deoxyadenosine (42a)

Solution of bis(N,N-diisopropylamino) chlorophosphite (200 mg, 0.75 mmol) in anhydrous dichloromethane (3 mL) was added dropwise to a stirred solution of N[6]-benzoyl-5'-O-(4,4'-dimethoxytrityl)-2'-deoxyadenosine, 10a, (395, 0.60 mmol) and N-ethyl-N,N-diisopropylamine (147 mg, 1.14 mmol) in anhydrous dichloromethane (4 mL) at −20° C. The solution was allowed to stir at room temperature for 2 h. To the obtained mixture, compound 7e (409 mg, 0.72 mmol) and 1H-tetrazole (0.45 M in MeCN, 0.6 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 563 mg (69.3%). $^{31}$P NMR (mixture of diastereomers, CD$_3$CN): δ 147.82, 147.28.

Example 74

N[6]-Phenoxyacetyl-5'-O-(4,4'-dimethoxytrityl)-3'-O—[(N,N-diisopropylamino)[14-[(3,4,6-tri-O-acetyl-2-acetylamino-2-deoxy-β-D-galactopyranosyl)oxy]-3,6,9,12-tetraoxatetradecyloxy]phosphinyl]-2'-deoxyadenosine (42b)

Solution of bis(N,N-diisopropylamino) chlorophosphite (230, 0.86 mmol) in anhydrous dichloromethane (3 mL) was added dropwise to a stirred solution of N[6]-phenoxyacetyl-5'-O-(4,4'-dimethoxytrityl)-2'-deoxyadenosine, 10b, (475 mg, 0.69 mmol) and N-ethyl-N,N-diisopropylamine (169 mg, 1.31 mmol) in anhydrous dichloromethane (4 mL) at −20° C. The solution was allowed to stir at room temperature for 2 h. To the obtained mixture, compound 7e (470 mg, 0.83 mmol) and 1H-tetrazole (0.45 M in MeCN, 0.7 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 610 mg (63.9%). $^{31}$P NMR (mixture of diastereomers, CD$_3$CN): δ 148.17, 147.52.

Example 75

N[2]-Isobutyryl-5'-O-(4,4'-dimethoxytrityl)-3'-O—[(N, N-diisopropylamino)[14-[(3,4,6-tri-O-acetyl-2-acetylamino-2-deoxy-β-D-galactopyranosyl)oxy]-3, 6,9,12-tetraoxatetradecyloxy]phosphinyl]-2'-deoxyguanosine (43a)

Solution of bis(N,N-diisopropylamino) chlorophosphite (203 mg, 0.76 mmol) in anhydrous dichloromethane (3 mL) was added dropwise to a stirred solution of N[2]-isobutyryl-5'-O-(4,4'-dimethoxytrityl)-2'-deoxyguanosine, 11a, (390 mg, 0.61 mmol) and N-ethyl-N,N-diisopropylamine (150 mg, 1.16 mmol) in anhydrous dichloromethane (4 mL) at −20° C. The solution was allowed to stir at room temperature for 2 h. To the obtained mixture, compound 7e (415 mg, 0.73 mmol) and 1H-tetrazole (0.45 M in MeCN, 0.6 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 543 mg (66.6%). $^{31}$P NMR (mixture of diastereomers, CD$_3$CN): δ 147.83, 147.24.

Example 76

N[2]-Phenoxyacetyl-5'-O-(4,4'-dimethoxytrityl)-3'-O—[(N,N-diisopropylamino)[14-[(3,4,6-tri-O-acetyl-2-acetylamino-2-deoxy-β-D-galactopyranosyl)oxy]-3,6,9,12-tetraoxatetradecyl]phosphino]-2'-deoxyguanosine (43b)

Solution of bis(N,N-diisopropylamino) chlorophosphite (217 mg, 0.81 mmol) in anhydrous dichloromethane (3 mL) was added dropwise to a stirred solution of N[2]-phenoxyacetyl-5'-O-(4,4'-dimethoxytrityl)-2'-deoxyguanosine, 11b, (457 mg, 0.65 mmol) and N-ethyl-N,N-diisopropylamine (160 mg, 1.24 mmol) in anhydrous dichloromethane (4 mL) at −20° C. The solution was allowed to stir at room temperature for 2 h. To the obtained mixture, compound 7e (443 mg, 0.78 mmol) and 1H-tetrazole (0.45 M in MeCN, 0.6 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 565 mg (62.1%). $^{31}$P NMR (mixture of diastereomers, CD$_3$CN): δ 148.29, 147.47.

Example 77

5'-O-(4,4'-Dimethoxytrityl)-2'-O-methyl-3'-O—[(N, N-diisopropylamino) [11-[(3,4,6-tri-O-acetyl-2-acetylamino-2-deoxy-β-D-galactopyranosyl)oxy]-3, 6,9-trioxaundecyloxy]phosphinyl]-5-methyluridine (52)

Solution of bis(N,N-diisopropylamino) chlorophosphite (313 mg, 1.18 mmol) in anhydrous dichloromethane (3 mL) was added dropwise to a stirred solution of 5'-O-(4,4'-dimethoxytrityl)-3'-O-methyl-5-methyluridine, 44, (540 mg, 0.94 mmol) and N-ethyl-N,N-diisopropylamine (231 mg, 1.79 mmol) in anhydrous dichloromethane (4 mL) at −20° C. The solution was allowed to stir at room temperature for 2 h. To the obtained mixture, 1-O-(11-hydroxy-3,6,9-trioxaundecyl)-3,4,6-tri-O-acetyl-2-acetylamino-2-deoxy-β-D-galactopyranoside, 7d, (591 mg, 1.13 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 977 mg (84.7%). $^{31}$P NMR (mixture of diastereomers, CD$_3$CN): δ 149.43, 148.62.

Example 78

N$^4$-Benzoyl-5'-O-(4,4'-dimethoxytrityl)-2'-O-methyl-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl] cytidine (53a)

Solution of bis(N,N-diisopropylamino) chlorophosphite (323 mg, 1.21 mmol) in anhydrous dichloromethane (3 mL) was added dropwise to a stirred solution of N$^4$-benzoyl-5'-O-(4,4'-dimethoxytrityl)-2'-O-methylcytidine, 45a, (646 mg, 0.97 mmol) and N-ethyl-N,N-diisopropylamine (238 mg, 1.84 mmol) in anhydrous dichloromethane (4 mL) at −20° C. The solution was allowed to stir at room temperature for 2 h. To the obtained mixture, compound 7d (609 mg, 1.16 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 1038 mg (81.2%). $^{31}$P NMR (mixture of diastereomers, CD$_3$CN): δ 149.17, 148.75.

Example 79

N$^4$-Acetyl-5'-O-(4,4'-dimethoxytrityl)-2'-O-methyl-3'-O—[(N,N-diisopropylamino)[11-[(3,4,6-tri-O-acetyl-2-acetylamino-2-deoxy-β-D-galactopyranosyl)oxy]-3,6,9-trioxaundecyl]cytidine (53c)

Solution of bis(N,N-diisopropylamino) chlorophosphite (340 mg, 1.28 mmol) in anhydrous dichloromethane (3 mL) was added dropwise to a stirred solution of N$^4$-acetyl-5'-O-(4,4'-dimethoxytrityl)-2'-O-methylcytidine, 45c, (616 mg, 1.02 mmol) and N-ethyl-N,N-diisopropylamine (250 mg, 1.94 mmol) in anhydrous dichloromethane (4 mL) at −20° C. The solution was allowed to stir at room temperature for 2 h. To the obtained mixture, compound 7d (641 mg, 1.22 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 1061 mg (82.8%). $^{31}$P NMR (mixture of diastereomers, CD$_3$CN): δ 148.98, 148.43.

Example 80

N$^6$-Benzoyl-5'-O-(4,4'-dimethoxytrityl)-2'-O-methyl-3'-O—[(N,N-diisopropylamino)[11-[(3,4,6-tri-O-acetyl-2-acetylamino-2-deoxy-β-D-galactopyranosyl)oxy]-3,6,9-trioxaundecyl]adenosine (54a)

Solution of bis(N,N-diisopropylamino) chlorophosphite (330 mg, 1.24 mmol) in anhydrous dichloromethane (3 mL) was added dropwise to a stirred solution of N$^6$-benzoyl-5'-O-(4,4'-dimethoxytrityl)-2'-O-methyladenosine, 46a, (681 mg, 0.99 mmol) and N-ethyl-N,N-diisopropylamine (243 mg, 1.88 mmol) in anhydrous dichloromethane (4 mL) at −20° C. The solution was allowed to stir at room temperature for 2 h. To the obtained mixture, compound 7d (622 mg, 1.19 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 1039 mg (78.3%). $^{31}$P NMR (mixture of diastereomers, CD$_3$CN): δ 148.92, 148.37.

Example 81

N$^6$-Phenoxyacetyl-5'-O-(4,4'-dimethoxytrityl)-2'-O-methyl-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl] adenosine (54b)

Solution of bis(N,N-diisopropylamino) chlorophosphite (343, 1.29 mmol) in anhydrous dichloromethane (3 mL) was added dropwise to a stirred solution of N$^6$-phenoxyacetyl-5'-O-(4,4'-dimethoxytrityl)-2'-O-methyladenosine, 46b, (739 mg, 1.03 mmol) and N-ethyl-N,N-diisopropylamine (253 mg, 1.96 mmol) in anhydrous dichloromethane (4 mL) at −20° C. The solution was allowed to stir at room temperature for 2 h. To the obtained mixture, compound 7d (647 mg, 1.24 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 1011 mg (71.6%). $^{31}$P NMR (mixture of diastereomers, CD$_3$CN): δ 147.92, 147.47.

Example 82

N$^2$-Isobutyryl-5'-O-(4,4'-dimethoxytrityl)-2'-O-methyl-3'-O—[(N,N-diisopropylamino)[11-[(3,4,6-tri-O-acetyl-2-acetylamino-2-deoxy-β-D-galactopyranosyl)oxy]-3,6,9-trioxaundecyloxy]phosphinyl] guanosine (55a)

Solution of bis(N,N-diisopropylamino) chlorophosphite (317 mg, 1.19 mmol) in anhydrous dichloromethane (3 mL) was added dropwise to a stirred solution of N$^2$-isobutyryl-5'-O-(4,4'-dimethoxytrityl)-2'-O-methylguanosine, 47a, (636 mg, 0.95 mmol) and N-ethyl-N,N-diisopropylamine (233 mg, 1.81 mmol) in anhydrous dichloromethane (4 mL) at −20° C. The solution was allowed to stir at room temperature for 2 h. To the obtained mixture, compound 7d (597 mg, 1.14 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 966 mg (76.9%). $^{31}$P NMR (mixture of diastereomers, CD$_3$CN): δ 147.90, 147.32.

Example 83

N$^2$-Phenoxyacetyl-5'-O-(4,4'-dimethoxytrityl)-2'-O-methyl-3'-O—[(N,N-diisopropylamino)[11-[(3,4,6-tri-O-acetyl-2-acetylamino-2-deoxy-β-D-galactopyranosyl)oxy]-3,6,9-trioxaundecyl]phosphino] guanosine (55b)

Solution of bis(N,N-diisopropylamino) chlorophosphite (337 mg, 1.26 mmol) in anhydrous dichloromethane (3 mL) was added dropwise to a stirred solution of N$^2$-phenoxyacetyl-5'-O-(4,4'-dimethoxytrityl)-2'-O-methylguanosine, 47b, (741 mg, 1.01 mmol) and N-ethyl-N,N-diisopropylamine (248 mg, 1.92 mmol) in anhydrous dichloromethane (4 mL) at −20° C. The solution was allowed to stir at room temperature for 2 h. To the obtained mixture, compound 7d (635 mg, 1.21 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 1011 mg (72.2%). $^{31}$P NMR (mixture of diastereomers, CD$_3$CN): δ 147.51, 146.96.

Example 84

5'-O-(4,4'-Dimethoxytrityl)-2'-fluoro-3'-O—[(N,N-diisopropylamino)[11-[(3,4,6-tri-O-acetyl-2-acetylamino-2-deoxy-β-D-galactopyranosyl)oxy]-3,6,9-trioxaundecyl]phosphino]-2'-deoxy-5-methyluridine (56)

Solution of bis(N,N-diisopropylamino) chlorophosphite (350 mg, 1.31 mmol) in anhydrous dichloromethane (3 mL) was added dropwise to a stirred solution of 5'-O-(4,4'-dimethoxytrityl)-2'-fluoro-2'-deoxy-5-methyluridine, 48, (591 mg, 1.05 mmol) and N-ethyl-N,N-diisopropylamine (258 mg, 2.00 mmol) in anhydrous dichloromethane (4 mL) at −20° C. The solution was allowed to stir at room temperature for 2 h. To the obtained mixture, 1-O-(11-hydroxy-3,6,9-trioxaundecyl)-3,4,6-tri-O-acetyl-2-acetylamino-2-deoxy-β-D-galactopyranoside, 7d, (660 mg, 1.26 mmol) and 1H-tetrazole (0.45 M in MeCN, 1.0 mL) were followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 1060 mg (83.1%). $^{31}$P NMR (mixture of diastereomers, CD$_3$CN): δ 148.38, 147.87.

Example 85

N$^4$-Benzoyl-5'-O-(4,4'-dimethoxytrityl)-2'-fluoro-3'-O—[(N,N-diisopropylamino)[11-[(3,4,6-tri-O-acetyl-2-acetylamino-2-deoxy-β-D-galactopyranosyl)oxy]-3,6,9-trioxaundecyl]phosphino]-2'-deoxycytidine (57a)

Solution of bis(N,N-diisopropylamino) chlorophosphite (343 mg, 1.31 mmol) in anhydrous dichloromethane (3 mL) was added dropwise to a stirred solution of N$^4$-benzoyl-5'-O-(4,4'-dimethoxytrityl)-2'-fluoro-2'-deoxycytidine, 49a, (673 mg, 1.03 mmol) and N-ethyl-N,N-diisopropylamine (253 mg, 1.96 mmol) in anhydrous dichloromethane (4 mL) at −20° C. The solution was allowed to stir at room temperature for 2 h. To the obtained mixture, compound 7d (647 mg, 1.24 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 1075 mg (79.9%). $^{31}$P NMR (mixture of diastereomers, CD$_3$CN): δ 148.52, 147.81.

Example 86

N$^4$-Acetyl-5'-O-(4,4'-dimethoxytrityl)-2'-fluoro-3'-O—[(N,N-diisopropylamino)[11-[(3,4,6-tri-O-acetyl-2-acetylamino-2-deoxy-β-D-galactopyranosyl)oxy]-3,6,9-trioxaundecyl]phosphino]-2'-deoxycytidine (57c)

Solution of bis(N,N-diisopropylamino) chlorophosphite (337 mg, 1.26 mmol) in anhydrous dichloromethane (3 mL) was added dropwise to a stirred solution of N$^4$-acetyl-5'-O-(4,4'-dimethoxytrityl)-2'-fluoro-2'-deoxycytidine, 49c, (598 mg, 1.01 mmol) and N-ethyl-N,N-diisopropylamine (248 mg, 1.92 mmol) in anhydrous dichloromethane (4 mL) at −20° C. The solution was allowed to stir at room temperature for 2 h. To the obtained mixture, compound 7d (635 mg, 1.21 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. The product was isolated by column chromatography on silica gel eluted with a step gradient starting from TEA—ethyl acetate—hexane (5:20:75) to a mixture of TEA in ethyl acetate (5:95). Evaporation of fractions gave the title compound as a viscous oil in a yield of 985 mg (78.4%). $^{31}$P NMR (mixture of diastereomers, CD$_3$CN): δ 148.23, 147.69.

Example 87

N$^6$-Benzoyl-5'-O-(4,4'-dimethoxytrityl)-2'-fluoro-3'-O—[(N,N-diisopropylamino)[11-[(3,4,6-tri-O-acetyl-2-acetylamino-2-deoxy-β-D-galactopyranosyl)oxy]-3,6,9-trioxaundecyl]phosphino]-2'-deoxyadenosine (58a)

Solution of bis(N,N-diisopropylamino) chlorophosphite (347 mg, 1.30 mmol) in anhydrous dichloromethane (3 mL) was added dropwise to a stirred solution of N$^6$-benzoyl-5'-O-(4,4'-dimethoxytrityl)-2'-fluoro-2'-deoxyadenosine, 50a, (703 mg, 1.4 mmol) and N-ethyl-N,N-diisopropylamine (255 mg, 1.98 mmol) in anhydrous dichloromethane (4 mL) at −20° C. The solution was allowed to stir at room temperature for 2 h. To the obtained mixture, compound 7d (653 mg, 1.25 mmol) and 1H-tetrazole (0.45 M in MeCN, 1.0 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 995 mg (72.0%). $^{31}$P NMR (mixture of diastereomers, CD$_3$CN): δ 148.23, 147.53.

Example 88

N$^6$-Phenoxyacetyl-5'-O-(4,4'-dimethoxytrityl)-2'-fluoro-3'-O—[(N,N-diisopropylamino)[11-[(3,4,6-tri-O-acetyl-2-acetylamino-2-deoxy-β-D-galactopyranosyl)oxy]-3,6,9-trioxaundecyl]phosphino]-2'-deoxyadenosine (58b)

Solution of bis(N,N-diisopropylamino) chlorophosphite (327, 1.23 mmol) in anhydrous dichloromethane (3 mL) was added dropwise to a stirred solution of N$^6$-phenoxyacetyl-5'-O-(4,4'-dimethoxytrityl)-2'-fluoro-2'-deoxyadenosine, 50b, (692 mg, 0.98 mmol) and N-ethyl-N,N-diisopropylamine (240 mg, 1.86 mmol) in anhydrous dichloromethane (4 mL) at −20° C. The solution was allowed to stir at room temperature for 2 h. To the obtained mixture, compound 7d (616 mg, 1.18 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 917 mg (68.9%). $^{31}$P NMR (mixture of diastereomers, CD$_3$CN): δ 148.47, 147.88.

Example 89

N$^2$-Isobutyryl-5'-O-(4,4'-dimethoxytrityl)-2'-fluoro-3'-O—[(N,N-diisopropylamino)[11-[(3,4,6-tri-O-acetyl-2-acetylamino-2-deoxy-β-D-galactopyranosyl)oxy]-3,6,9-trioxaundecyl]phosphino]-2'-deoxyguanosine (59a)

Solution of bis(N,N-diisopropylamino) chlorophosphite (320 mg, 1.20 mmol) in anhydrous dichloromethane (3 mL) was added dropwise to a stirred solution of N$^2$-isobutyryl-5'-O-(4,4'-dimethoxytrityl)-2'-fluoro-2'-deoxyguanosine, 51a, (631 mg, 0.96 mmol) and N-ethyl-N,N-diisopropylamine (236 mg, 1.82 mmol) in anhydrous dichloromethane (4 mL) at −20° C. The solution was allowed to stir at room temperature for 2 h. To the obtained mixture, compound 7d (603 mg, 1.15 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 850 mg (67.6%). $^{31}$P NMR (mixture of diastereomers, CD$_3$CN): δ 148.34, 147.71.

Example 90

N$^2$-Phenoxyacetyl-5'-O-(4,4'-dimethoxytrityl)-2'-fluoro-3'-O—[(N,N-diisopropylamino)[11-[(3,4,6-tri-O-acetyl-2-acetylamino-2-deoxy-β-D-galactopyranosyl)oxy]-3,6,9-trioxaundecyl]phosphino]-2'-deoxyguanosine (59b)

Solution of bis(N,N-diisopropylamino) chlorophosphite (330 mg, 1.24 mmol) in anhydrous dichloromethane (3 mL) was added dropwise to a stirred solution of N$^2$-phenoxyacetyl-5'-O-(4,4'-dimethoxytrityl)-2'-fluoro-2'-deoxyguanosine, 51b, (715 mg, 0.99 mmol) and N-ethyl-N,N-diisopropylamine (243 mg, 1.88 mmol) in anhydrous dichloromethane (4 mL) at −20° C. The solution was allowed to stir at room temperature for 2 h. To the obtained mixture, compound 7d (622 mg, 1.19 mmol) and 1H-tetrazole (0.45 M in MeCN, 0.9 mL) were added followed by stirring at room temperature for 14 h. The reaction mixture was quenched by addition of excess 5% aqueous NaHCO$_3$. The emulsion was diluted with 5% aqueous NaHCO$_3$ (10 mL), and the product was extracted with ethyl acetate (3×50 mL). Extracts were washed with brine, dried over anhydrous Na$_2$SO$_4$, and evaporated to oil. Evaporation of fractions gave the title compound as a viscous oil in a yield of 840 mg (61.7%). $^{31}$P NMR (mixture of diastereomers, CD$_3$CN): δ 148.59, 147.90.

Example 91

5'-O-(4,4'-Dimethoxytrityl)-3'-O—[(N,N-diisopropylamino)[5-[(3,4,6-tri-O-acetyl-2-acetylamino-2-deoxy-β-D-galactopyranosyl)oxy]-3-oxapentyloxy]phosphinyl]thymidine (28)

To the magnetically stirred mixture of 1-O-(5-hydroxy-3-oxapentyl)-3,4,6-tri-O-acetyl-2-acetylamino-2-deoxy-β-D-galactopyranoside, 7b, (501 g, 1.15 mmol) N-ethyl-N,N-diisopropylamine (282 mg, 2.19 mmol), and anhydrous CH$_3$CN (10 mL) was added a solution of N,N,N',N'-tetraisopropyl chlorophosphite (364 mg, 1.44 mmol) in anhydrous DCM (5 mL) at −20° C. The mixture was allowed to warm up to room temperature over 2 h. A solution of 5'-O-(4,4'-dimethoxytrityl)thymidine, 8, (565 mg, 1.09 mmol), in anhydrous DCM (5 mL) was added followed by the addition of a solution of 1H-tetrazole in acetonitrile (0.45 M, 1.1 mL). The reaction mixture was stirred for 18 h at room temperature and was quenched by adding 5% aqueous NaHCO$_3$. The product was extracted with ethyl acetate (3×50 mL). Combined extracts were washed with brine (50 mL), dried over anhydrous Na$_2$SO$_4$, and evaporated to dryness. The product was isolated by column chromatography on silica gel eluted with a step gradient starting from TEA—ethyl acetate—hexane (5:20:75) to a mixture of TEA in ethyl acetate (10:90). Evaporation of fractions gave compound 24 as white solid foam in a yield of 941 mg (77.7%). $^{31}$P NMR (mixture of diastereomers, CD$_3$CN): δ 148.12, 147.63.

Example 92

Oligonucleotides 61-64, 67-72, and 81-84 were synthesized by the phosphoramidite method on an Applied Biosystems DNA/RNA synthesizer 394 on 1 μmol scale starting with a commercial DMT-nucleoside-succinyl-CPG (1000 Å, Glen Research, Sterling, Va.). The standard synthetic cycle useful in assemblying oligonucleotides with phosphate backbone comprised the following steps:
  (a) detritylation of the solid phase-bound material with 3% dichloroacetic acid in dichloromethane followed by washing with acetonitrile;
  (b) coupling of nucleoside phosphoramidite building block (0.1 M in acetonitrile) required by the sequence to the solid support-bound material in the presence of 1H-tetrazole (0.45 M in acetonitrile);
  (c) capping of unreacted solid support-bound hydroxy groups with a mixture of acetic anhydride and N-methyl imidazole and
  (d) oxidation of the solid support-bound phosphite triester groups with iodine (0.05 M in a mixture of pyridine, tetrahydrofurane, water).

Preparation of oligonucleotide phosphorothioates was conducted as disclosed in U.S. Pat. No. 7,723,528. Accordingly, steps (a) and (b) remained as disclosed above. The iodine solution was replaced with a solution of N'-(3-thioxo-3H-1,2,4-dithiazol-5-yl)-N,N-dimethylmethanimidamide (0.025 M in pyridine). Upon the completion of the coupling step (b) and washing the solid phase with acetonitrile, the sulfurization step was conducted. The capping step followed the sulfurization. The cycle appropriate for the assembly of the desired oligonucleotide was repeated as required by the sequence in preparation.

The synthetic cycle for incorporation of the protected ribonucleoside phosphoramidite building blocks was different from that disclosed above in that the coupling time was extended to 10 min.

The synthetic cycle for incorporation of the phosphoramidite building blocks disclosed in the present invention was different from that disclosed above in that the coupling time was extended to 1 min.

The final release of oligonucleotides 61-64 from the solid support, deprotection of internucleosidic phosphates, and monosaccharide residues was carried out by treatment under the following conditions:

A. Concentrated ammonium hydroxide, room temperature, 18 h;
  B. Concentrated aqueous ammonium hydroxide, 65° C., 8 h;
  C. 0.05 M K$_2$CO$_3$ in anhydrous MeOH, room temperature, 4 h;
  D. 0.5 M Piperidine in anhydrous acetonitrile, room temperature, 15 min, followed by a mixture of 1,2-diaminoethane and toluene (50:50 v/v), room temperature, 4 h;
  E. 25% Aqueous t-butylamine, 65° C., 4 h;
  F. Mixture of concentrated aqueous ammonium hydroxide and 40% aqueous methylamine (50:50 v/v), room temperature, 120 min.

Upon completion of the deprotection under the conditions A, B, E, and F, the liquid phase was collected and evaporated in vacuo to dryness. The residue was dissolved in water (1 mL) and analyzed by reverse-phase HPLC and by ES MS.

Upon completion of the deprotection under the condition C, the reaction mixtures were neutralized by addition of 0.25 M aqueous NaH$_2$PO$_4$ (250 μL per 1 mL of deprotection solution). The solid phase was spun down; the liquid phase was collected and analyzed as described above.

Upon completion of the deprotection under the condition D, the solid phase was spun down, and the liquid phase was discarded. The solid phase was washed with toluene (2×1 mL) and with acetonitrile (2×1 mL). The solid phase was suspended in water (1 mL) and the suspension was centrifugated. The liquid phase was collected and analyzed as described above.

The final release of oligonucleotides 67-72 and 81-84 from the solid support, deprotection of internucleosidic phosphates, monosaccharide residues, and nucleic bases was carried out by treatment with concentrated aqueous ammonium hydroxide (2 mL) at room temperature for 18 h. The removal of 2'-O-tBDMS groups from oligonucleotide 84 (SEQ. ID 15) was additionally carried out as disclosed in Song, Q. and Jones, R. A. Tetrahedron Lett. 1999, 40, 4653-4654, which is incorporated by reference herein in its entirety. Upon evaporation in vacuo, the crude deprotection mixtures were dissolved in water and analyzed by ES MS and reverse-phase HPLC. HPLC analysis was carried out on Phenomenex Gemini C18 column (4.6×150 mm) using 0.05 M Tris-HCl as Buffer A, acetonitrile as Buffer B, and a linear gradient from 0 to 100% B in 45 min at a flow rate of 1 mL/min. Peaks were detected by a UV-VIS detector at 264 nm.

Skilled artisans will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method of preparing a synthetic oligonucleotide, the method comprising reacting a compound of Formula I:

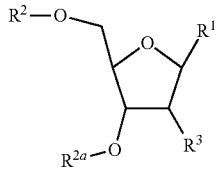

Formula I wherein:
R$^1$ is an optionally protected nucleic base selected from 9-adeninyl, 1-cytosinyl, 9-guaninyl, 1-thyminyl, 1-uracilyl, 2-amino-9-adeninyl, N$^6$-methyl-9-adeninyl, 7-deaza-9-adeninyl, 7-deaza-8-aza-9-adeninyl, 8-amino-9-adeninyl, 5-methyl-1-cytosinyl, N$^4$-ethyl-1-cytosinyl, 7-deaza-9-guaninyl, 7-deaza-8-aza-9-guaninyl, 8-amino-9-guaninyl, 7-deaza-9-xanthinyl, 9-hypoxanthinyl, N$^6$-benzoyl-9-adeninyl, N$^6$-phenoxyacetyl-9-adeninyl, N$^6$-(4-isopropylphenoxy)acetyl-9-adeninyl, N$^4$-benzoyl-1-cytosinyl, N$^4$-acetyl-1-cytosinyl, N$^4$-phenoxyacetyl-1-cytosinyl, N$^4$-(4-isopropylphenoxy)acetyl-1-cytosinyl, N$^4$-benzoyl-5-methyl-1-cytosinyl, N$^4$-acetyl-5-methyl-1-cytosinyl, N$^4$-phenoxyacetyl-5-methyl-1-cytosinyl, N$^4$-(4-isopropylphenoxy)acetyl-5-methyl-1-cytosinyl, N$^2$-isobutyryl-9-guaninyl, N$^2$-phenoxyacetyl-9-guaninyl, N$^2$-(4-isopropylphenoxy)acetyl-9-guaninyl, and N$^2$—(N,N-dimethylformamidino)-9-guaninyl;

one of R$^2$ and R$^{2a}$ is a protecting group of the trityl type selected from (4-methoxyphenyl)diphenylmethyl, bis-(4-methoxyphenyl)phenylmethyl, tris-(methoxyphenyl)methyl, 9-phenylxanthen-9-yl, and 9-(p-methoxyphenyl)xanthen-9-yl, and the other is a phosphoramidite moiety:

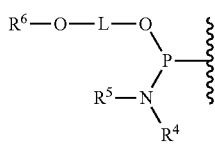

wherein:
each R$^4$ and R$^5$ is, independently, C$_1$ to C$_6$ alkyl, or R$^4$ and R$^5$ together with the nitrogen atom they are attached to form a cycle, wherein R$^4$+R$^5$=(CH$_2$)$_n$X (CH$_2$)$_m$, wherein:
X is an atom of oxygen or CH$_2$ group;
each n and m is, independently, an integer from 2 to about 5;
L is a linking moiety [(CH$_2$)$_p$Y(CH$_2$)$_q$]$_r$— wherein:
each p, q, and r is, independently, an integer from 1 to 18;
Y is a chemical bond, oxygen atom, sulfur atom, Q$^1$, —N(Q$^1$)C(=O)N(Q$^2$)-, —C(=O)N(Q$^1$)-, or —N(Q$^1$)C(=O)—, wherein:
each Q$^1$ and Q$^2$ is hydrogen atom, a methyl group, an ethyl group, a propyl group, an isopropyl group, an acetyl group, a trifluoroacetyl group, a phenoxyacetyl group, a benzoyl group, or a 9-fluorenylmethyloxycarbonyl group;
R$^6$ is a substituted monosaccharide residue of Formula II

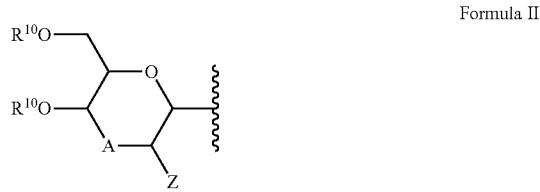

Formula II wherein:
each R$^{10}$ is, independently, an acyl protecting group, a trityl-type protecting group, a silyl protecting group, an alkyl group containing from 1 to 18 atoms of carbon, a benzyl group, a 4-methoxybenzyl group, a propargyl group, or one of R$^{10}$ is a protected monosaccharide residue of Formula II, and the other R$^{10}$ is an acetyl group;
A is a chemical bond or CHOR$^{10}$;
Z is a hydrogen, OR$^{10}$, or N(Q$^{2a}$)Q$^3$ wherein:
each Q$^{2a}$ and Q$^3$ is, independently, a hydrogen atom, a methyl group, an ethyl group, a propyl group, an isopropyl group, an acetyl group, a trifluoroacetyl group, a phenoxyacetyl group, a benzoyl group, or a 9-fluorenylmethyloxycarbonyl group;

$R^3$ is a hydrogen atom, a fluorine atom, a substituted hydroxy group $OR^7$, or a substituted amino group $NR^8R^9$ wherein:

each $R^7$ is, independently, a $C_1$ to $C_6$ alkyl, 2-alkoxyethyl group, or an N-methylcarboxamidomethyl group; and each $R^8$ and $R^9$ is, independently, a hydrogen atom, a methyl group, an ethyl group, a propyl group, an isopropyl group, an acetyl group, a trifluoroacetyl group, a phenoxyacetyl group, a benzoyl group, or a 9-fluorenylmethyloxycarbonyl group;

with a compound of Formula IV:

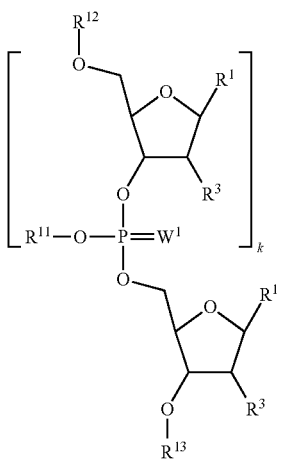

Formula IV wherein:

one of $R^{12}$ and $R^{13}$ is a hydrogen atom, and the other is a protecting group or a linker connected to a solid support;

k is an integer selected from 0 to about 100; and $R^1$, $R^3$, $R^{11}$, and $W^1$ have the same values as set forth above for Formula I.

2. The method of claim 1, wherein $R^1$ is a nucleic base selected from the group consisting of $N^6$-benzoyl-9-adeninyl, $N^6$-phenoxyacetyl-9-adeninyl, $N^6$-(4-isopropylphenoxy)acetyl-9-adeninyl, 9-adeninyl, $N^4$-benzoyl-1-cytosinyl, $N^4$-acetyl-1-cytosinyl, $N^4$-phenoxyacetyl-1-cytosinyl, $N^4$-(4-isopropylphenoxy)acetyl-1-cytosinyl, $N^4$-benzoyl-5-methyl-1-cytosinyl, $N^4$-acetyl-5-methyl-1-cytosinyl, 1-cytosinyl, $N^4$-phenoxyacetyl-5-methyl-1-cytosinyl, $N^4$-(4-isopropylphenoxy)acetyl-5-methyl-1-cytosinyl, 5-methyl-1-cytosinyl, $N^2$-isobutyryl-9-guaninyl, $N^2$-phenoxyacetyl-9-guaninyl, $N^2$-(4-isopropylphenoxy)acetyl-9-guaninyl, $N^2$—(N,N-dimethylformamidino)-9-guaninyl, 9-guaninyl, 1-thyminyl, and 1-uracilyl.

3. The method of claim 1, wherein $R^2$ is a 4,4'-dimethoxytrityl group and $R^{2a}$ is

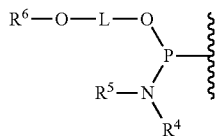

4. The method of claim 1, wherein $R^{2a}$ is a 4,4'-dimethoxytrityl group and $R^2$ is

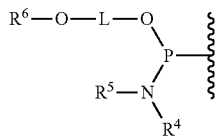

5. The method of claim 1, wherein $R^3$ is a hydrogen atom.
6. The method of claim 1, wherein $R^3$ is $OCH_3$.
7. The method of claim 1, wherein $R^3$ is a fluorine atom.
8. The method of claim 1, wherein each $R^4$ and $R^5$ is an isopropyl group.
9. The method of claim 1, wherein L is —$(CH_2)_3$—.
10. The method of claim 1, wherein L is —$(CH_2)_4$—.
11. The method of claim 1, wherein L is —$[(CH_2)_2$—$O]_2$—.
12. The method of claim 1, wherein L is —$[(CH_2)_2$—$O]_3$—.
13. The method of claim 1, wherein L is —$[(CH_2)_2$—$O]_4$—.
14. The method of claim 1, wherein L is —$[(CH_2)_2$—$O]_5$—.
15. The method of claim 1, wherein $R^6$ is a protected β-D-glucopyranosidyl group.
16. The method of claim 1, wherein $R^6$ is a protected β-D-galactopyranosidyl group.
17. The method of claim 1, wherein $R^6$ is a protected 2-amino-2-deoxy-β-D-glucopyranosidyl group.
18. The method of claim 17, wherein one of $Q^{2a}$ and $Q^3$ is a hydrogen atom, and the other is an acetyl group.
19. The method of claim 1, wherein $R^6$ is a protected 2-amino-2-deoxy-β-D-galactopyranosidyl group.
20. The method of claim 19, wherein one of $Q^{2a}$ and $Q^3$ is a hydrogen atom, and the other is an acetyl group.
21. The method of claim 1, wherein each of $R^{10}$ is an acetyl group.
22. The method of claim 1, wherein each of $R^{10}$ is a benzoyl group.
23. The method of claim 1, wherein each of $R^{10}$ is a butyryl group.
24. The method of claim 1, wherein each of $R^{10}$ is an isobutyryl group.
25. The compound of claim 1, wherein each of $R^{10}$ is a propionyl group.
26. The method of claim 1, wherein each of $R^{10}$ is a 4-methylbenzoyl group.
27. The method of claim 1, wherein one of $R^{10}$ is a protected monosaccharide residue of Formula II, and the other $R^{10}$ is an acetyl group.

* * * * *

SEQUENCE LISTING

<160> NUMBER OF SEQ ID NOS: 15

<210> SEQ ID NO 1
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 1
tttttttttt                                                              10

<210> SEQ ID NO 2
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified to
      thymidine-3'-[[(beta-D-glucopyranosyl)oxy]propyl]phosphate

<400> SEQUENCE: 2
tttttttttt                                                              10

<210> SEQ ID NO 3
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified to
      thymidine-3'-[[(beta-D-glucopyranosyl)oxy]propyl]phosphate
<220> FEATURE:
<221> NAME/KEY: modified_base
<222> LOCATION: (2)..(2)
<223> OTHER INFORMATION: Residue modified to
      thymidine-3'-[[(beta-D-glucopyranosyl)oxy]propyl]phosphate

<400> SEQUENCE: 3
tttttttttt                                                              10

<210> SEQ ID NO 4
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified to
      thymidine-3'-[[(beta-D-glucopyranosyl)oxy]propyl]phosphate
<220> FEATURE:
<221> NAME/KEY: modified_base
<222> LOCATION: (2)..(2)
<223> OTHER INFORMATION: Residue modified to
      thymidine-3'-[[(beta-D-glucopyranosyl)oxy]propyl]phosphate
<220> FEATURE:
<221> NAME/KEY: modified_base
<222> LOCATION: (3)..(3)
<223> OTHER INFORMATION: Residue modified to
      thymidine-3'-[[(beta-D-glucopyranosyl)oxy]propyl]phosphate

<400> SEQUENCE: 4
tttttttttt                                                              10

<210> SEQ ID NO 5
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base

```
<222> LOCATION: (1)..(1)
<223> OTHER INFORMATION: Residue modified to
      thymidine-3'-[[(beta-D-glucopyranosyl)oxy]propyl]phosphate
<220> FEATURE:
<221> NAME/KEY: modified_base
<222> LOCATION: (2)..(2)
<223> OTHER INFORMATION: Residue modified to
      thymidine-3'-[[(beta-D-glucopyranosyl)oxy]propyl]phosphate
<220> FEATURE:
<221> NAME/KEY: modified_base
<222> LOCATION: (3)..(3)
<223> OTHER INFORMATION: Residue modified to
      thymidine-3'-[[(beta-D-glucopyranosyl)oxy]propyl]phosphate
<220> FEATURE:
<221> NAME/KEY: modified_base
<222> LOCATION: (4)..(4)
<223> OTHER INFORMATION: Residue modified to
      thymidine-3'-[[(beta-D-glucopyranosyl)oxy]propyl]phosphate

<400> SEQUENCE: 5
tttttttttt                                                                10

<210> SEQ ID NO 6
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (2)..(2)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (3)..(3)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (4)..(4)
<223> OTHER INFORMATION: Residue modified at phosphate moiety to
      phosphotriester with 1-[2-[[2-(beta-D-
      glucopyranosyloxy)ethyl]oxy]ethyl] modification

<400> SEQUENCE: 6
tttttttttt                                                                10

<210> SEQ ID NO 7
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (2)..(2)
<223> OTHER INFORMATION: Residue modified at phosphate moiety to
      phosphotriester with 1-[3-(beta-D-glucopyranosyloxy)propyl]
      modification
<220> FEATURE:
```

```
<221> NAME/KEY: modified_base
<222> LOCATION: (3)..(3)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (4)..(4)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (6)..(6)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (7)..(7)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (8)..(8)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (9)..(9)
<223> OTHER INFORMATION: Residue modified at phosphate moiety to
      phosphotriester with 1-[3-(beta-D-glucopyranosyloxy)propyl]
      modification

<400> SEQUENCE: 7
tttttttttt                                                          10

<210> SEQ ID NO 8
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (2)..(2)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (3)..(3)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (4)..(4)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (5)..(5)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
```

-continued

<222> LOCATION: (6)..(6)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (7)..(7)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (8)..(8)
<223> OTHER INFORMATION: Residue modified at phosphate moiety to
      phosphotriester with 1-[3-(beta-D-glucopyranosyloxy)propyl]
      modification
<220> FEATURE:
<221> NAME/KEY: modified_base
<222> LOCATION: (9)..(9)
<223> OTHER INFORMATION: Residue modified at phosphate moiety to
      phosphotriester with 1-[3-(beta-D-glucopyranosyloxy)propyl]
      modification

<400> SEQUENCE: 8
tttttttttt                                                          10

<210> SEQ ID NO 9
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (2)..(2)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (3)..(3)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (4)..(4)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (5)..(5)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (6)..(6)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (7)..(7)
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (8)..(8)

```
<223> OTHER INFORMATION: Residue modified at phosphate moiety to
      phosphotriester with 1-[2-[[2-(beta-D-
      glucopyranosyloxy)ethyl]oxy]ethyl] modification
<220> FEATURE:
<221> NAME/KEY: modified_base
<222> LOCATION: (9)..(9)
<223> OTHER INFORMATION: Residue modified at phosphate moiety to
      phosphotriester with 1-[2-[[2-(beta-D-
      glucopyranosyloxy)ethyl]oxy]ethyl] modification

<400> SEQUENCE: 9
tttttttttt                                                          10

<210> SEQ ID NO 10
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified at phosphate moiety to
      phosphotriester with 1-[2-[[2-(N-acetyl-2-deoxy-2-amino-beta-D-
      galactopyranosyloxy)ethyl]oxy]ethyl] modification
<220> FEATURE:
<221> NAME/KEY: modified_base
<222> LOCATION: (2)..(2)
<223> OTHER INFORMATION: Residue modified at phosphate moiety to
      phosphotriester with 1-[2-[[2-(N-acetyl-2-deoxy-2-amino-beta-D-
      galactopyranosyloxy)ethyl]oxy]ethyl] modification
<220> FEATURE:
<221> NAME/KEY: modified_base
<222> LOCATION: (3)..(3)
<223> OTHER INFORMATION: Residue modified at phosphate moiety to
      phosphotriester with 1-[2-[[2-(N-acetyl-2-deoxy-2-amino-beta-D-
      galactopyranosyloxy)ethyl]oxy]ethyl] modification
<220> FEATURE:
<221> NAME/KEY: modified_base
<222> LOCATION: (4)..(4)
<223> OTHER INFORMATION: Residue modified at phosphate moiety to
      phosphotriester with 1-[2-[[2-(N-acetyl-2-deoxy-2-amino-beta-D-
      galactopyranosyloxy)ethyl]oxy]ethyl] modification

<400> SEQUENCE: 10
tttttttttt                                                          10

<210> SEQ ID NO 11
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified at phosphate moiety to
      phosphotriester with 1-[2-[[2-(N-acetyl-2-deoxy-2-amino-beta-D-
      galactopyranosyloxy)ethyl]oxy]ethyl] modification
<220> FEATURE:
<221> NAME/KEY: modified_base
<222> LOCATION: (2)..(2)
<223> OTHER INFORMATION: Residue modified at phosphate moiety to
      phosphotriester with 1-[2-[[2-(N-acetyl-2-deoxy-2-amino-beta-D-
      galactopyranosyloxy)ethyl]oxy]ethyl] modification
<220> FEATURE:
<221> NAME/KEY: modified_base
<222> LOCATION: (3)..(3)
<223> OTHER INFORMATION: Residue modified at phosphate moiety to
      phosphotriester with 1-[2-[[2-(N-acetyl-2-deoxy-2-amino-beta-D-
      galactopyranosyloxy)ethyl]oxy]ethyl] modification
<220> FEATURE:
<221> NAME/KEY: modified_base
<222> LOCATION: (4)..(4)
<223> OTHER INFORMATION: Residue modified at phosphate moiety to
```

```
        phosphotriester with 1-[2-[[2-(N-acetyl-2-deoxy-2-amino-beta-D-
        galactopyranosyloxy)ethyl]oxy]ethyl] modification
<220> FEATURE:
<221> NAME/KEY: modified_base
<222> LOCATION: (6)..(6)
<223> OTHER INFORMATION: Residue modified at phosphate moiety to
        phosphotriester with 1-[2-[[2-(N-acetyl-2-deoxy-2-amino-beta-D-
        galactopyranosyloxy)ethyl]oxy]ethyl] modification
<220> FEATURE:
<221> NAME/KEY: modified_base
<222> LOCATION: (7)..(7)
<223> OTHER INFORMATION: Residue modified at phosphate moiety to
        phosphotriester with 1-[2-[[2-(N-acetyl-2-deoxy-2-amino-beta-D-
        galactopyranosyloxy)ethyl]oxy]ethyl] modification
<220> FEATURE:
<221> NAME/KEY: modified_base
<222> LOCATION: (8)..(8)
<223> OTHER INFORMATION: Residue modified at phosphate moiety to
        phosphotriester with 1-[2-[[2-(N-acetyl-2-deoxy-2-amino-beta-D-
        galactopyranosyloxy)ethyl]oxy]ethyl] modification
<220> FEATURE:
<221> NAME/KEY: modified_base
<222> LOCATION: (9)..(9)
<223> OTHER INFORMATION: Residue modified at phosphate moiety to
        phosphotriester with 1-[2-[[2-(N-acetyl-2-deoxy-2-amino-beta-D-
        galactopyranosyloxy)ethyl]oxy]ethyl] modification

<400> SEQUENCE: 11
tttttttttt                                                                  10

<210> SEQ ID NO 12
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified with phosphorothioate further
        modified with 1-[3-(beta-D-glucopyranosyloxy)propyl] modification
<220> FEATURE:
<221> NAME/KEY: modified_base
<222> LOCATION: (2)..(2)
<223> OTHER INFORMATION: Residue modified with phosphorothioate further
        modified with 1-[3-(beta-D-glucopyranosyloxy)propyl] modification
<220> FEATURE:
<221> NAME/KEY: modified_base
<222> LOCATION: (3)..(3)
<223> OTHER INFORMATION: Residue modified with phosphorothioate further
        modified with 1-[3-(beta-D-glucopyranosyloxy)propyl] modification
<220> FEATURE:
<221> NAME/KEY: modified_base
<222> LOCATION: (4)..(4)
<223> OTHER INFORMATION: Residue modified with phosphorothioate further
        modified with 1-[3-(beta-D-glucopyranosyloxy)propyl] modification
<220> FEATURE:
<221> NAME/KEY: modified_base
<222> LOCATION: (5)..(5)
<223> OTHER INFORMATION: Residue modified with phosphorothioate further
        modified with 1-[3-(beta-D-glucopyranosyloxy)propyl] modification
<220> FEATURE:
<221> NAME/KEY: modified_base
<222> LOCATION: (6)..(6)
<223> OTHER INFORMATION: Residue modified with phosphorothioate further
        modified with 1-[3-(beta-D-glucopyranosyloxy)propyl] modification
<220> FEATURE:
<221> NAME/KEY: modified_base
<222> LOCATION: (7)..(7)
<223> OTHER INFORMATION: Residue modified with phosphorothioate further
        modified with 1-[3-(beta-D-glucopyranosyloxy)propyl] modification
<220> FEATURE:
<221> NAME/KEY: modified_base
<222> LOCATION: (8)..(8)
<223> OTHER INFORMATION: Residue modified with phosphorothioate further
        modified with 1-[3-(beta-D-glucopyranosyloxy)propyl] modification
<220> FEATURE:
```

<221> NAME/KEY: modified_base
<222> LOCATION: (9)..(9)
<223> OTHER INFORMATION: Residue modified with phosphorothioate further
      modified with 1-[3-(beta-D-glucopyranosyloxy)propyl] modification
<220> FEATURE:
<221> NAME/KEY: modified_base
<222> LOCATION: (10)..(10)
<223> OTHER INFORMATION: Residue modified with phosphorothioate further
      modified with 1-[3-(beta-D-glucopyranosyloxy)propyl] modification
<220> FEATURE:
<221> NAME/KEY: modified_base
<222> LOCATION: (11)..(11)
<223> OTHER INFORMATION: Residue modified with phosphorothioate further
      modified with 1-[3-(beta-D-glucopyranosyloxy)propyl] modification
<220> FEATURE:
<221> NAME/KEY: modified_base
<222> LOCATION: (12)..(12)
<223> OTHER INFORMATION: Residue modified with phosphorothioate further
      modified with 1-[3-(beta-D-glucopyranosyloxy)propyl] modification
<220> FEATURE:
<221> NAME/KEY: modified_base
<222> LOCATION: (13)..(13)
<223> OTHER INFORMATION: Residue modified with phosphorothioate further
      modified with 1-[3-(beta-D-glucopyranosyloxy)propyl] modification
<220> FEATURE:
<221> NAME/KEY: modified_base
<222> LOCATION: (14)..(14)
<223> OTHER INFORMATION: Residue modified with phosphorothioate further
      modified with 1-[3-(beta-D-glucopyranosyloxy)propyl] modification
<220> FEATURE:
<221> NAME/KEY: modified_base
<222> LOCATION: (15)..(15)
<223> OTHER INFORMATION: Residue modified with phosphorothioate further
      modified with 1-[3-(beta-D-glucopyranosyloxy)propyl] modification
<220> FEATURE:
<221> NAME/KEY: modified_base
<222> LOCATION: (16)..(16)
<223> OTHER INFORMATION: Residue modified with phosphorothioate further
      modified with 1-[3-(beta-D-glucopyranosyloxy)propyl] modification
<220> FEATURE:
<221> NAME/KEY: modified_base
<222> LOCATION: (17)..(17)
<223> OTHER INFORMATION: Residue modified with phosphorothioate further
      modified with 1-[3-(beta-D-glucopyranosyloxy)propyl] modification

<400> SEQUENCE: 12
tgtgagtacc actgattc                                                   18

<210> SEQ ID NO 13
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified with phosphorothioate further
      modified with 1-[3-(N-acetyl-2-deoxy-2-amino-beta-D-
      glucopyranosyloxy)propyl] modification
<220> FEATURE:
<221> NAME/KEY: modified_base
<222> LOCATION: (2)..(2)
<223> OTHER INFORMATION: Residue modified with phosphorothioate further
      modified with 1-[3-(N-acetyl-2-deoxy-2-amino-beta-D-
      glucopyranosyloxy)propyl] modification
<220> FEATURE:
<221> NAME/KEY: modified_base
<222> LOCATION: (3)..(3)
<223> OTHER INFORMATION: Residue modified with phosphorothioate further
      modified with 1-[3-(N-acetyl-2-deoxy-2-amino-beta-D-
      glucopyranosyloxy)propyl] modification
<220> FEATURE:
<221> NAME/KEY: modified_base
<222> LOCATION: (4)..(4)
<223> OTHER INFORMATION: Residue modified with phosphorothioate
<220> FEATURE:

```
<221> NAME/KEY: modified_base
<222> LOCATION: (5)..(5)
<223> OTHER INFORMATION: Residue modified with phosphorothioate
<220> FEATURE:
<221> NAME/KEY: modified_base
<222> LOCATION: (6)..(6)
<223> OTHER INFORMATION: Residue modified with phosphorothioate
<220> FEATURE:
<221> NAME/KEY: modified_base
<222> LOCATION: (7)..(7)
<223> OTHER INFORMATION: Residue modified with phosphorothioate
<220> FEATURE:
<221> NAME/KEY: modified_base
<222> LOCATION: (8)..(8)
<223> OTHER INFORMATION: Residue modified with phosphorothioate
<220> FEATURE:
<221> NAME/KEY: modified_base
<222> LOCATION: (9)..(9)
<223> OTHER INFORMATION: Residue modified with phosphorothioate
<220> FEATURE:
<221> NAME/KEY: modified_base
<222> LOCATION: (10)..(10)
<223> OTHER INFORMATION: Residue modified with phosphorothioate
<220> FEATURE:
<221> NAME/KEY: modified_base
<222> LOCATION: (11)..(11)
<223> OTHER INFORMATION: Residue modified with phosphorothioate
<220> FEATURE:
<221> NAME/KEY: modified_base
<222> LOCATION: (12)..(12)
<223> OTHER INFORMATION: Residue modified with phosphorothioate
<220> FEATURE:
<221> NAME/KEY: modified_base
<222> LOCATION: (13)..(13)
<223> OTHER INFORMATION: Residue modified with phosphorothioate
<220> FEATURE:
<221> NAME/KEY: modified_base
<222> LOCATION: (14)..(14)
<223> OTHER INFORMATION: Residue modified with phosphorothioate
<220> FEATURE:
<221> NAME/KEY: modified_base
<222> LOCATION: (15)..(15)
<223> OTHER INFORMATION: Residue modified with phosphorothioate further
      modified with 1-[3-(N-acetyl-2-deoxy-2-amino-beta-D-
      glucopyranosyloxy)propyl] modification
<220> FEATURE:
<221> NAME/KEY: modified_base
<222> LOCATION: (16)..(16)
<223> OTHER INFORMATION: Residue modified with phosphorothioate further
      modified with 1-[3-(N-acetyl-2-deoxy-2-amino-beta-D-
      glucopyranosyloxy)propyl] modification
<220> FEATURE:
<221> NAME/KEY: modified_base
<222> LOCATION: (17)..(17)
<223> OTHER INFORMATION: Residue modified with phosphorothioate further
      modified with 1-[3-(N-acetyl-2-deoxy-2-amino-beta-D-
      glucopyranosyloxy)propyl] modification

<400> SEQUENCE: 13
tgtgagtacc actgatta                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue modified with phosphorothioate further
      modified with 1-[2-[[2-(N-acetyl-2-deoxy-2-amino-beta-D-
      galactopyranosyloxy)ethyl]oxy]ethyl] modification
<220> FEATURE:
<221> NAME/KEY: modified_base
<222> LOCATION: (2)..(2)
<223> OTHER INFORMATION: Residue modified with phosphorothioate further
```

-continued

```
          modified with 1-[2-[[2-(N-acetyl-2-deoxy-2-amino-beta-D-
          galactopyranosyloxy)ethyl]oxy]ethyl] modification
<220> FEATURE:
<221> NAME/KEY: modified_base
<222> LOCATION: (3)..(3)
<223> OTHER INFORMATION: Residue modified with phosphorothioate further
          modified with 1-[2-[[2-(N-acetyl-2-deoxy-2-amino-beta-D-
          galactopyranosyloxy)ethyl]oxy]ethyl] modification
<220> FEATURE:
<221> NAME/KEY: modified_base
<222> LOCATION: (4)..(4)
<223> OTHER INFORMATION: Residue modified with phosphorothioate
<220> FEATURE:
<221> NAME/KEY: modified_base
<222> LOCATION: (5)..(5)
<223> OTHER INFORMATION: Residue modified with phosphorothioate
<220> FEATURE:
<221> NAME/KEY: modified_base
<222> LOCATION: (6)..(6)
<223> OTHER INFORMATION: Residue modified with phosphorothioate
<220> FEATURE:
<221> NAME/KEY: modified_base
<222> LOCATION: (7)..(7)
<223> OTHER INFORMATION: Residue modified with phosphorothioate
<220> FEATURE:
<221> NAME/KEY: modified_base
<222> LOCATION: (8)..(8)
<223> OTHER INFORMATION: Residue modified with phosphorothioate
<220> FEATURE:
<221> NAME/KEY: modified_base
<222> LOCATION: (9)..(9)
<223> OTHER INFORMATION: Residue modified with phosphorothioate
<220> FEATURE:
<221> NAME/KEY: modified_base
<222> LOCATION: (10)..(10)
<223> OTHER INFORMATION: Residue modified with phosphorothioate
<220> FEATURE:
<221> NAME/KEY: modified_base
<222> LOCATION: (11)..(11)
<223> OTHER INFORMATION: Residue modified with phosphorothioate
<220> FEATURE:
<221> NAME/KEY: modified_base
<222> LOCATION: (12)..(12)
<223> OTHER INFORMATION: Residue modified with phosphorothioate
<220> FEATURE:
<221> NAME/KEY: modified_base
<222> LOCATION: (13)..(13)
<223> OTHER INFORMATION: Residue modified with phosphorothioate
<220> FEATURE:
<221> NAME/KEY: modified_base
<222> LOCATION: (14)..(14)
<223> OTHER INFORMATION: Residue modified with phosphorothioate
<220> FEATURE:
<221> NAME/KEY: modified_base
<222> LOCATION: (15)..(15)
<223> OTHER INFORMATION: Residue modified with phosphorothioate further
          modified with 1-[2-[[2-(N-acetyl-2-deoxy-2-amino-beta-D-
          galactopyranosyloxy)ethyl]oxy]ethyl] modification
<220> FEATURE:
<221> NAME/KEY: modified_base
<222> LOCATION: (16)..(16)
<223> OTHER INFORMATION: Residue modified with phosphorothioate further
          modified with 1-[2-[[2-(N-acetyl-2-deoxy-2-amino-beta-D-
          galactopyranosyloxy)ethyl]oxy]ethyl] modification
<220> FEATURE:
<221> NAME/KEY: modified_base
<222> LOCATION: (17)..(17)
<223> OTHER INFORMATION: Residue modified with phosphorothioate further
          modified with 1-[2-[[2-(N-acetyl-2-deoxy-2-amino-beta-D-
          galactopyranosyloxy)ethyl]oxy]ethyl] modification

<400> SEQUENCE: 14
tgtgagtacc actgatta                                                        18

<210> SEQ ID NO 15
<211> LENGTH: 18
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue is deoxy residue modified with
      phosphorothioate further modified with 1-[2-[[2-(N-acetyl-2-deoxy-
      2-amino-beta-D-galactopyranosyloxy)ethyl]oxy]ethyl] modification
<220> FEATURE:
<221> NAME/KEY: modified_base
<222> LOCATION: (2)..(2)
<223> OTHER INFORMATION: Residue is deoxy residue modified with
      phosphorothioate further modified with 1-[2-[[2-(N-acetyl-2-deoxy-
      2-amino-beta-D-galactopyranosyloxy)ethyl]oxy]ethyl] modification
<220> FEATURE:
<221> NAME/KEY: modified_base
<222> LOCATION: (3)..(3)
<223> OTHER INFORMATION: Residue is deoxy residue modified with
      phosphorothioate further modified with 1-[2-[[2-(N-acetyl-2-deoxy-
      2-amino-beta-D-galactopyranosyloxy)ethyl]oxy]ethyl] modification
<220> FEATURE:
<221> NAME/KEY: modified_base
<222> LOCATION: (4)..(4)
<223> OTHER INFORMATION: Residue is ribonucleic acid moiety modified
      with phosphorothioate
<220> FEATURE:
<221> NAME/KEY: modified_base
<222> LOCATION: (5)..(5)
<223> OTHER INFORMATION: Residue is ribonucleic acid moiety modified
      with phosphorothioate
<220> FEATURE:
<221> NAME/KEY: modified_base
<222> LOCATION: (6)..(6)
<223> OTHER INFORMATION: Residue is ribonucleic acid moiety modified
      with phosphorothioate
<220> FEATURE:
<221> NAME/KEY: modified_base
<222> LOCATION: (7)..(7)
<223> OTHER INFORMATION: Residue is ribonucleic acid moiety modified
      with phosphorothioate
<220> FEATURE:
<221> NAME/KEY: modified_base
<222> LOCATION: (8)..(8)
<223> OTHER INFORMATION: Residue is ribonucleic acid moiety modified
      with phosphorothioate
<220> FEATURE:
<221> NAME/KEY: modified_base
<222> LOCATION: (9)..(9)
<223> OTHER INFORMATION: Residue is ribonucleic acid moiety modified
      with phosphorothioate
<220> FEATURE:
<221> NAME/KEY: modified_base
<222> LOCATION: (10)..(10)
<223> OTHER INFORMATION: Residue is ribonucleic acid moiety modified
      with phosphorothioate
<220> FEATURE:
<221> NAME/KEY: modified_base
<222> LOCATION: (11)..(11)
<223> OTHER INFORMATION: Residue is ribonucleic acid moiety modified
      with phosphorothioate
<220> FEATURE:
<221> NAME/KEY: modified_base
<222> LOCATION: (12)..(12)
<223> OTHER INFORMATION: Residue is ribonucleic acid moiety modified
      with phosphorothioate
<220> FEATURE:
<221> NAME/KEY: modified_base
<222> LOCATION: (13)..(13)
<223> OTHER INFORMATION: Residue is ribonucleic acid moiety modified
      with phosphorothioate
<220> FEATURE:
<221> NAME/KEY: modified_base
<222> LOCATION: (14)..(14)
<223> OTHER INFORMATION: Residue is ribonucleic acid moiety modified
      with phosphorothioate
<220> FEATURE:
<221> NAME/KEY: modified_base
<222> LOCATION: (15)..(15)
```

```
<223> OTHER INFORMATION: Residue is deoxy residue modified with
      phosphorothioate further modified with 1-[2-[[2-(N-acetyl-2-deoxy-
      2-amino-beta-D-galactopyranosyloxy)ethyl]oxy]ethyl] modification
<220> FEATURE:
<221> NAME/KEY: modified_base
<222> LOCATION: (16)..(16)
<223> OTHER INFORMATION: Residue is deoxy residue modified with
      phosphorothioate further modified with 1-[2-[[2-(N-acetyl-2-deoxy-
      2-amino-beta-D-galactopyranosyloxy)ethyl]oxy]ethyl] modification
<220> FEATURE:
<221> NAME/KEY: modified_base
<222> LOCATION: (17)..(17)
<223> OTHER INFORMATION: Residue is deoxy residue modified with
      phosphorothioate further modified with 1-[2-[[2-(N-acetyl-2-deoxy-
      2-amino-beta-D-galactopyranosyloxy)ethyl]oxy]ethyl] modification

<400> SEQUENCE: 15
tgtgaguacc acugatta                                                      18
```